US008923349B2

(12) United States Patent
Huber et al.

(10) Patent No.: US 8,923,349 B2
(45) Date of Patent: Dec. 30, 2014

(54) FOURIER DOMAIN MODE LOCKING: METHOD AND APPARATUS FOR CONTROL AND IMPROVED PERFORMANCE

(71) Applicant: Massachuetts Institute of Technology, Cambridge, MA (US)

(72) Inventors: Robert A. Huber, Schnaitsee (DE); James G. Fujimoto, Medford, MA (US); Desmond C. Adler, Melrose, MA (US)

(73) Assignee: Massachusettes Institute of Technology, Cambridge, MA (US)

( * ) Notice: Subject to any disclaimer, the term of this patent is extended or adjusted under 35 U.S.C. 154(b) by 0 days.

(21) Appl. No.: 13/860,995

(22) Filed: Apr. 11, 2013

(65) Prior Publication Data
US 2013/0329757 A1   Dec. 12, 2013

Related U.S. Application Data

(60) Continuation of application No. 13/654,878, filed on Oct. 18, 2012, now abandoned, which is a division of
(Continued)

(51) Int. Cl.
*H01S 3/10* (2006.01)
*H01S 3/098* (2006.01)
(Continued)

(52) U.S. Cl.
CPC .............. *H01S 3/1106* (2013.01); *H01S 3/137* (2013.01); *H01S 3/08027* (2013.01); *H01S 3/06725* (2013.01); *H01S 3/06791* (2013.01); *H01S 3/106* (2013.01); *G01N 2021/653* (2013.01); *G01N 2021/1787* (2013.01); *H01S 3/1305* (2013.01); *H01S 3/0675* (2013.01); *H01S 3/1109* (2013.01); *H01S 3/06712* (2013.01); *H01S 2301/04* (2013.01); *H01S 3/07* (2013.01); *H01S 3/1062* (2013.01)
USPC .............................................. 372/20; 372/18

(58) Field of Classification Search
USPC .................................. 372/18, 19, 20, 29.011
See application file for complete search history.

(56) References Cited

U.S. PATENT DOCUMENTS

| 5,263,037 A | 11/1993 | Trutna, Jr. et al. |
| 5,574,739 A | 11/1996 | Carrunthers et al. |

(Continued)

FOREIGN PATENT DOCUMENTS

| EP | 0 524 382 A2 | 1/1993 |
| JP | 2970780 | 8/1999 |

(Continued)

OTHER PUBLICATIONS

Takesuc, H., and Horiguchi, T., "Broad-Band Lightwave Synthesized Frequency Sweeper Using Synchronous Filtering," *J. of Lightwave Technology*, 22(3): 755-762 (2004).

(Continued)

*Primary Examiner* — Armando Rodriguez
(74) *Attorney, Agent, or Firm* — Hamilton, Brook, Smith & Reynolds, P.C.

(57) ABSTRACT

A control system for improving and stabilizing Fourier domain mode locking (FDML) operation. The control system may also provide regulation of FDML operational parameters such as filter tuning, laser gain, polarization, polarization chromaticity, elliptical polarization retardance, and/or dispersion. The control system may be located internal to or external from the FDML laser cavity.

18 Claims, 33 Drawing Sheets

Related U.S. Application Data application No. 12/288,715, filed on Oct. 22, 2008, now Pat. No. 8,315,282, which is a continuation-in-part of application No. 12/220,898, filed on Jul. 28, 2008, now abandoned, which is a continuation of application No. 11/337,105, filed on Jan. 20, 2006, now Pat. No. 7,414,779.

(60) Provisional application No. 60/645,359, filed on Jan. 20, 2005.

(51) Int. Cl.
| | |
|---|---|
| H01S 3/11 | (2006.01) |
| H01S 3/137 | (2006.01) |
| H01S 3/13 | (2006.01) |
| H01S 3/08 | (2006.01) |
| H01S 3/067 | (2006.01) |
| H01S 3/106 | (2006.01) |
| G01N 21/65 | (2006.01) |
| G01N 21/17 | (2006.01) |
| H01S 3/07 | (2006.01) |

(56) References Cited

U.S. PATENT DOCUMENTS

| | | | |
|---|---|---|---|
| 5,590,142 | A | 12/1996 | Shan |
| 5,786,930 | A | 7/1998 | Takatsu et al. |
| 5,910,839 | A | 6/1999 | Erskine |
| 5,956,355 | A | 9/1999 | Swanson et al. |
| 6,282,215 | B1 | 8/2001 | Zorabedian et al. |
| 6,449,047 | B1 * | 9/2002 | Bao et al. ............ 356/478 |
| 6,559,946 | B2 | 5/2003 | Davidson et al. |
| 6,816,515 | B1 | 11/2004 | Yun et al. |
| 8,315,282 | B2 | 11/2012 | Huber et al. |
| 2002/0154316 | A1 | 10/2002 | Davidson et al. |
| 2002/0176457 | A1* | 11/2002 | DeCusatis et al. ........... 372/26 |
| 2002/0191190 | A1 | 12/2002 | Cierullies et al. |
| 2004/0004768 | A1 | 1/2004 | Friessnegg et al. |
| 2004/0130724 | A1 | 7/2004 | Maestle |
| 2006/0131488 | A1* | 6/2006 | Thingbo et al. ........ 250/227.23 |
| 2006/0187537 | A1 | 8/2006 | Huber et al. |
| 2008/0165366 | A1 | 7/2008 | Schmitt |
| 2011/0216325 | A1 | 9/2011 | Schmitt |
| 2013/0058364 | A1 | 3/2013 | Huber et al. |

FOREIGN PATENT DOCUMENTS

| | | |
|---|---|---|
| JP | 2002-523905 | 7/2002 |
| JP | 2006-309187 | 11/2006 |
| JP | 2008-281869 | 11/2008 |
| WO | WO 02/01282 A1 | 1/2002 |
| WO | WO 03/096106 A1 | 11/2003 |
| WO | WO 2008/086017 A1 | 7/2008 |
| WO | WO 2010/047936 A2 | 4/2010 |

OTHER PUBLICATIONS

Yun, S.H. et al., "Wavelength-Swept Fiber Laser with Frequency Shifted Feedback and REsonantly Swept Intra-Cavity Acoustooptic Tunable Filter," *IEEE Journal of Selected Topics in Quantum Electronics*, 3(4): 1087-1096 (1997).

Yun, S.H., et al., "High-speed wavelength-swept semiconductor laser with a polygon-scanner-based wavelength filter," *Optics Letters*, 28(20): 1981-1983 (2003).

Yun, S.H., et al., "Interrogation of fiber grating sensor arrays with a wavelength-swept fiber laser," *Optics Letters*, 23(11): 843-845 (1998).

Huber, R., et al., "Fourier Domain Mode Locked Lasers for OCT imaging at up to 290 kHz sweep rates," *Proc. of SPIE-OSA Biomedical Optics, SPIE* vol. 5861: (2005).

Shimizu, K., et al., "Measurement of Rayleigh Backscattering in Single-Mode Fibers Based on Coherent OFDR Employing a DFB Laser Diode," *IEEE Photonics Technology Letters*, 3(11): 1039-1041 (1991).

Telle, J.M. and Tang, C.L., "Very rapid tuning of cw dye laser," *Applied Physics Letters*, 26(10): 572-574 (1975).

Crozatier, V., et al., "Photon Echo Chirp Transform Using a Stabilized Frequency Agile Laser," *Journal of Luminescence*, 127, pp. 104-109 (2007).

Gorju, G., et al., "Active Stabilization of a rapidly Chirped Laser by an Optoelectronic Digital Servo-Loop Control," *Optics Letters*, 32(5), pp. 484-486 (2007).

Eigenwillig, Christoph M. et al., "K-Space Linear Fourier Domain Mode Locked Laser and Applications for Optical Coherence Tomography," *Opt. Express* 16:8916-8937 (2008).

Huber, R., et al., "Fourier Domain Mode Locked Lasers for OCT Imaging at up to 290 kHz Sweep Rates," *Proceedings of SPIE, OSA Biomedical Optics, SPIE, U.S.* 5861:1-6 (Jan. 2005).

Adler, D.C., et al., "Photothermal Detection of Gold Nanoparticles Using Phase-Sensitive Optical Coherence Tomography," *Optics Express* 16(7):4376-4835 (Mar. 2008).

Set, S. et al., "Intra-Cavity-Modulated Swept-Lasers for "Real-Time" Dispersion Measurement," in *Optical Fiber Communications Conference*, A. Sawchuk, ed., vol. 70 of OSA Trends in Optics and Photonics, paper WK4, pp. 256-257 (2002).

Huber, R., et al., "Fourier Domain Mode Locking (FDML): A New Laser for Operating Regime and Applications for Optical Coherence Tomography," *Optics Express*, 14(8): 3225-3237 (Apr. 17, 2006).

Office Action, U.S. Appl. No. 13/654,878, Date of mailing: Feb. 15, 2013.

EPO Communication and extended European Search Report and Annex to the European Search Report on European Application No. 10 17 9871, 7 pages, mailed Feb. 14, 2013.

Huber, R., et al., "Buffered Fourier Domain Mode Locking: Undirectional Swept Laser Sources for Optical Coherence Tomography Imaging at 370,000 lines/s," *Optics Letters*, 31(20): 2975-2977 (Oct. 2006).

Huber, R., et al., "Fournier Domain Mode Locking at 1050 nm for Ultra-High-Speed Optical Coherence Tomography of the Human Retina at 236,000 Axial Scans per Second," *Optics Letters*, 32(14): 2049-2051 (Jul. 2007).

\* cited by examiner

Figure 14A-C

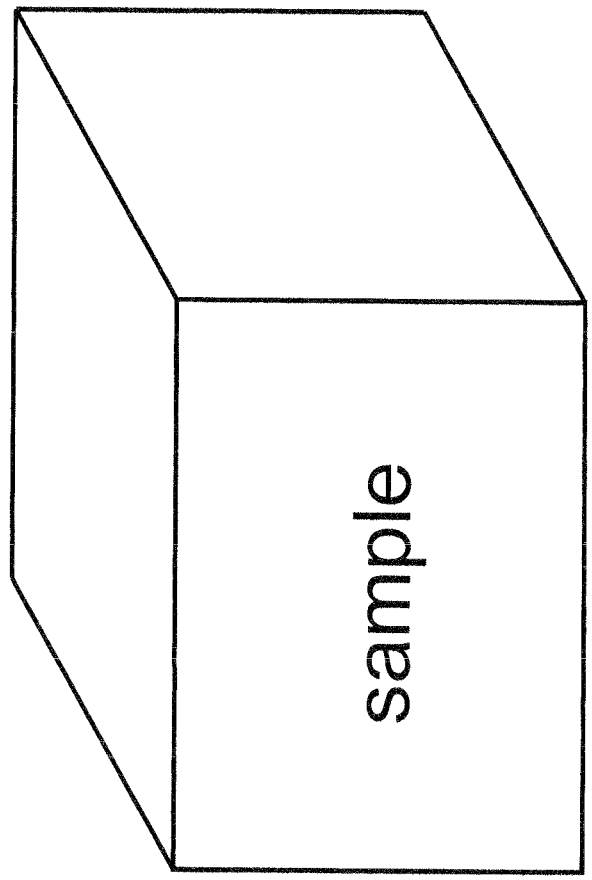
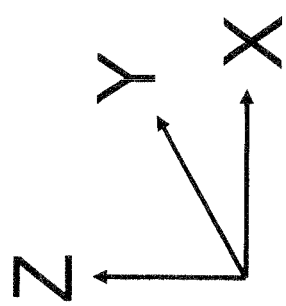
Figure 30

… (1)

FOURIER DOMAIN MODE LOCKING: METHOD AND APPARATUS FOR CONTROL AND IMPROVED PERFORMANCE

RELATED APPLICATIONS

This application is a continuation of U.S. patent application Ser. No. 13/654,878, filed Oct. 18, 2012, which is a divisional of U.S. patent application Ser. No. 12/288,715, filed Oct. 22, 2008, which is a continuation-in-part of U.S. patent application Ser. No. 12/220,898, filed Jul. 28, 2008, which is a continuation application of U.S. application Ser. No. 11/337,105, filed Jan. 20, 2006, now U.S. Pat. No. 7,414,779, which claims the benefit of U.S. provisional patent application 60/645,359, filed Jan. 20, 2005. The entire teachings of the above applications are incorporated herein by reference.

GOVERNMENT SUPPORT

This invention was made with government support under Grant No. BES0522845 awarded by the National Science Foundation and under Grant Nos. R01 EY011289 and R01 CA075289 awarded by the National Institutes of Health and under Contract Nos. FA9550-07-1-0014 and FA9550-07-1-0101 awarded by the Air Force Office of Scientific Research. The government has certain rights in the invention.

BACKGROUND

In many industries and technical areas of research, various systems and devices are used to obtain precise measurements or imaging. In conjunction with the need for precision, there is also a demand for high speed data collection. To satisfy these two criteria, many wave-based technologies are used. Specifically, electromagnetic radiation, in general, often in the form of light, is used in different applications to obtain measurement data. Typical applications include optical coherence tomography (OCT) and other interferometric based approaches.

However, different measurement applications often require additional conditions for satisfactory results. The source of the electromagnetic radiation and the resultant output wave characteristics are often deficient with respect to a set of parameters. For example, some sources produce waves that are low power or only use a portion of the available spectral intensity. Linewidth limitations plague other wave sources. As a result, many industrial and technical applications are limited by the wave generating component of the system.

SUMMARY

Accordingly, a need exists for wave sources with improved power delivery and enhanced utilization of available spectra. Furthermore, a need exists for devices, systems, and methods that allow precise measurements or imaging to be conducted at high speeds and that provide stability of various system parameters.

In example embodiments a control system, and corresponding method, to stabilize operation of a Fourier Domain Mode Locking (FDML) laser by controlling FDML parameters is presented. The system may include a light measurement device that may be configured to receive a periodically wavelength swept light-field from a laser output from the FDML laser. The light measurement device may also be configured to determine a measured parameter. The system may further include a comparator device that may be in communication with the light measurement device. The comparator device may be configured to compare the measured parameter with a comparison parameter. The comparator device may further be configured to generate an error signal as a function of a result of the comparison. The system may also include a laser control device that may be in communication with the comparator to generate a control signal to adjust control parameters of operation of the FDML laser as a function of the error signal.

Example embodiments may also include a system, and corresponding method, to regeneratively generate control signals for FDML operation in a FDML laser. The system may include the light measurement device. The system may also include an electronic processing device in communication with the light measurement device. The electronic processing device may be configured to generate a control signal directly as a function of the measured parameter. The system may also include a laser control device in communication with the electronic processing device to adjust control parameters of operation of the FDML laser as a function of the control signal.

In example embodiments a system to generate control signals for FDML operation in a FDML laser may also include the light measurement device. The system may further include an electronic processing device that may be configured to generate non-sinusoidal output control signals, based on the measured parameter, to adjust a time versus wavelength tuning characteristic of a tunable wavelength selective filter of the FDML laser.

In an example embodiment the electronic processing device may be configured to generate time dependent gain control signals, based on the measured parameter, to adjust a laser gain element of the FDML laser and control an intensity versus wavelength output of the laser.

Example embodiments may also include a control system, and corresponding method, to manage polarization chromaticity and an elliptical polarization retardance of delay fiber in an FDML laser. The control system may include a polarization state analyzing device that may be configured to receive an output from the FDML laser and determine a measured polarization state based on the laser output. The system may also include a processing device that may be configured to receive the measured polarization state and generate a polarization control signal based on the measured polarization state. The system may further include an active polarization controller that may be configured to change the polarization state of light as a function of the polarization control signal.

Example embodiments may also include a control system, and corresponding method, to manage passively polarization chromaticity and elliptical polarization retardance of delay fiber in an FDML laser. The system may include a first dispersive element that may be configured to receive a laser output from the laser. The dispersive element may further be configured to provide a respective polarization rotation for respective wavelengths resulting in spatially dispersed light. The system may also include a wedge of birefringent material that may receive the spatially dispersed light, and may be configured to provide respective differential phase retardation of orthogonal polarization states to respective wavelength components.

In example embodiments the control system to manage passively polarization chromaticity and elliptical polarization retardance, may include a coupling device that may be configured to receive a laser output from the FDML laser. The system may also include a plurality of birefringent units, each birefringent unit may further include a plurality of fiber loops. Each birefringent unit may be configured to provide a respective polarization rotation for respective wavelengths of the laser output. The system may also include a plurality of reflectors, each reflector may be positioned between a pair of birefringent units. The reflectors may be configured to reflect back respective portions of the laser output at respective positions, where different wavelength components experience different birefringence.

Example embodiments may further include a FDML laser for generating light with reduced sensitivity to polarization chromaticity and elliptical polarization retardance of delay fiber in an FDML laser. The FDML laser may include a gain element that may be configured to amplify a wave having a wavelength. The laser may also include a time varying tunable wavelength selective filter that may be in communication with the gain element, the tunable filter element may be configured to selectively filter waves. The laser may further include a feedback element in that may be communication with the tunable filter element and the gain element. The laser may further include at least one optical element that may be configured to direct a wavelength swept optical waveform inside a cavity of the FDML laser to propagate through the delay fiber in two different directions.

Other example embodiments may include a system to modify a wavelength swept waveform of an FDML laser. The system may include a separating optical element that may separate the wavelength swept waveform of the FDML laser into at least two portions. The system may also include a delay element that may introduce a time delay between the at least two portions. The system may further include a recombination element that may recombine the at least two portions upon introduction of the time delay.

Example embodiments may further comprise a control system, and corresponding method, to synchronize a sweep frequency of an adjustably tunable optical filter in a FDML laser with an optical roundtrip time of a cavity of the FDML laser. The system may include a photodetector that may to detect a measured transient output intensity of the FDML laser. The system may also include a comparator device in communication with the photodetector that may compare the measured transient output intensity with a comparison parameter. The comparator device may further be configured to generate an error signal as a function of the comparison to adjust the sweep frequency of a synchronous waveform driver of the FDML laser.

Example embodiments also include a control system, and corresponding method, to adjust a DC voltage of a Fabry Perot filter inside a cavity of a FDML. The system may include at least one photodetector in communication with a wavelength selective filter. The system may also include a comparator device in communication with the at least one photodetector that may compare a timing of the signal from the photodetector with a timing of a fixed clock with a known phase relationship to a FDML output sweep. The comparator device may be further configured to generate an error signal as a function of the comparison, the error signal adjusting the DC offset voltage of the Fabry Perot filter.

Other Example embodiments include a FDML laser, and corresponding method, for generating light that is swept in a stepwise manner over a discrete series of optical frequencies. The laser may include a gain element that may be configured to amplify a wave having a wavelength. The laser may also a time varying adjustably tunable wavelength selective filter element in communication with the gain element. The tunable filter element may be configured to selectively filter waves, where the filter element may be tuned in a time-varying, repetitive, periodic manner with a period T. The tunable filter element may also be configured to filter the waves in a selectable manner within discrete narrow wavelength bands that can be arbitrarily selected. The laser may also include an auxiliary wavelength selective filter element in communication with the tunable wavelength selective filter element. The auxiliary filter element may be configured to filter waves in a selectable manner, where the auxiliary filter element may have a plurality of transmission maxima within a gain bandwidth of the gain element. The laser may further include a feedback element in communication with the auxiliary filter element and the gain element, and a circuit including the time varying adjustably tunable wavelength selective filter element. The auxiliary wavelength selective filter element, the gain element, and the feedback element may be in a configuration in which the roundtrip time for the wave to propagate through the circuit is substantially equal to a non-zero integer multiple of the period T.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 30 is an illustrative example of data acquisition and data display according to example embodiments.

DETAILED DESCRIPTION

A description of example embodiments of the invention follows. The teachings of all patents, published applications and references cited herein are incorporated by reference in their entirety.

The term "Fourier Domain Mode Locked laser" or "FDML laser" in the following refers to the apparatus described in U.S. application Ser. No. 11/337,105, "Fourier Domain Mode Locking Method and Apparatus for the Generation of Fast Frequency Swept Waveforms and Chirped Pulses by Resonant Frequency Tuning," filed on Jan. 20, 2006, now U.S. Pat. No. 7,414,779.

The terms "sweep" or "tune" in the following as relating to FDML operation or the output of an FDML laser should be understood to refer to a controlled variation in optical frequency over time or, equivalently, optical wavelength over time. "Sweep" or "tune" can refer to the case where the optical frequency varies continuously in time or to the case where the optical frequency varies discontinuously in time in a stepwise manner.

Figure 1:
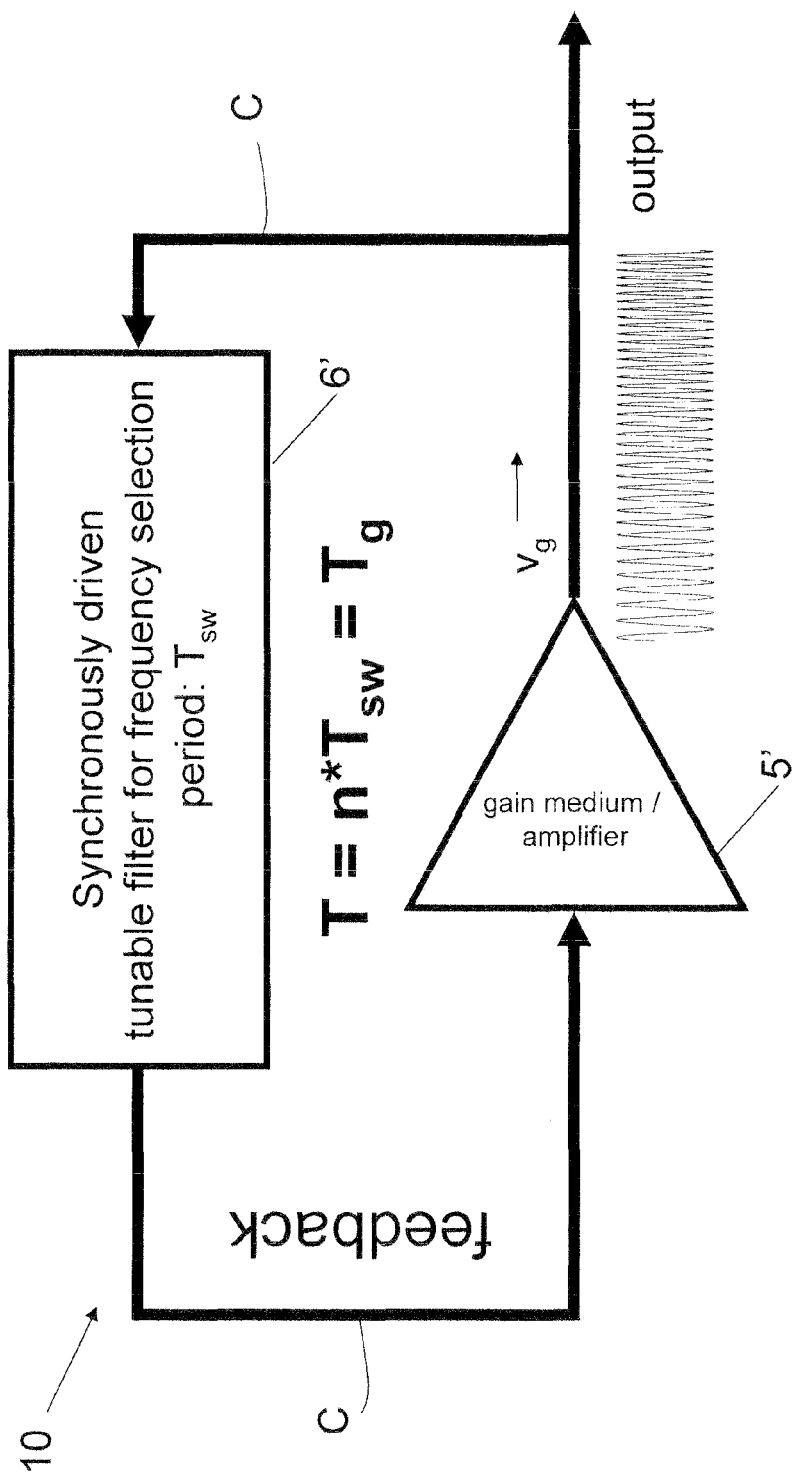
FIG. 1 is a schematic diagram depicting a system for matching tuning period and round trip time in a wavelength swept laser, such as a Fourier domain mode locked laser.

An example FDML system is shown in FIG. 1. The system 10 is suitable for Fourier Domain Mode Locking (FDML) using resonant frequency tuning. As shown, a circuit C connects an amplifier/gain medium (5') with a tunable filter (6') to facilitate feedback within the amplifier. The roundtrip time $T_g$ of a wave is measured relative to the filter location in the circuit C. The tuning or sweep period $T_{sw}$ is the periodic time over which the filter element is tuned to selectively pass waves of varying frequency. $T_g$ and $T_{sw}$ are either substantially the same, or $T_{sw}$ is a higher harmonic of $T_g$. This relation can be expressed by:

$$n \cdot T_{sw} = T_g$$

where n is a positive non-zero integer, $T_{sw}$ is the sweep period or tuning time and $T_g$ is the group roundtrip time of the wave. The period of the filter sweep or variation and the group roundtrip time are synchronized. The group roundtrip time $T_g$ is determined by:

$$T_g = \frac{L}{v_g}$$

wherein $v_g$ is the group velocity and the length of the feedback line or cavity is L. As a result, the feedback is not within one sweep with itself, but within two sweeps. The feedback delay line in the cavity "stores" all frequencies of a complete sweep, in contrast to standard frequency swept sources.

The frequency transmitted through the filter makes one roundtrip and is fed back at the time when the filter is at the same frequency position. The wave does not have to build up again every time the filter is tuned. Using this method, cavities can be swept in frequency rapidly, independently of the cavity life time. This results in a narrow instantaneous linewidth. The fixed phase relation between sequential sweeps makes it possible to observe interference signals between two sweeps. This is usually not possible in standard tunable frequency sources since these two sweeps have no defined phase relation between each other.

If the filter element is continuously tuned and driven synchronously with the roundtrip time, the output is a sequence of long sweeps in frequency over time. Since the instantaneous spectrum within each sweep is narrow, the instantaneous coherence length is very long. In combination with the repetitive feedback, this leads to a fixed phase relation between the modes which span the range of the frequency sweep or frequency variation. Thus, the modes are phase locked.

In general, a locking of all modes over the whole spectral range of the sweep may be expected in the case of a very narrow and repetitive filtering. For more typical cases, a jitter of the phase of modes within the bandwidth of the filter-function typically occurs. However, a phase correlation between modes which are spectrally separated more than the width of the filter function is provided by the filtering. The average phase of all modes within the filter function is stabilized and locked for different spectral positions of the filter.

The example embodiments described in the following paragraphs helps to improve and stabilize the Fourier domain mode locking operation by controlling or regulating the FDML parameters. FDML lasers employ unique control systems not found in other types of lasers. By applying these unique control systems, the properties of the output light generated by FDML lasers can also be modified and optimized in ways that are not possible with other types of lasers. For example, the drive or control signal of the intra-cavity tunable filter can be managed in an appropriate way to stabilize FDML operation. Additionally, the gain properties of the laser medium can be controlled to optimize the enhanced coherence properties typical for FDML lasers. Furthermore, unique to FDML lasers, the overall dispersion and elliptical polarization retardance can be balanced using methods and apparatus in the described example embodiments. Example embodiments may employ special control systems and methods for the parameters of FDML lasers, and may use unique output properties of FDML lasers to generate error signals for control or to generate seed signals for regenerative drive signal generators.

Experimental results have shown that FDML operation may be sensitive to some of the operational parameters. Compared to other types of frequency swept laser or other types of laser in general, FDML lasers may often be much more sensitive to some of the operation parameters. Example embodiments involve methods and apparatuses to stabilize the parameters for FDML operation, including but not limited to: the filter sweep waveform, the tuning or stepping frequency and speed, the corresponding central wavelength of the sweep, and the total tuning range or amplitude. By modulating the laser gain medium, the spectral output shape can be controlled. This is only possible in FDML operation and not in other types of mode locked lasers, because in FDML operation, the entire wavelength sweep is stored inside the cavity. Therefore, light with different wavelengths passes through the laser gain medium at different times, providing an ability to modify or shape the output spectral shape by applying a time-varying modulation signal to the laser gain medium.

Another unique feature of FDML operation is that it typically incorporates a long optical fiber of several kilometers length. This fiber acts as an elliptical polarization retarder, where one set of wavelengths in the cavity experiences a different amount of polarization rotation than another set of wavelengths in the cavity. Since the laser gain medium typically produces different amounts of gain depending on the polarization of the input light, the elliptical polarization retardance unique to FDML lasers results in unwanted variations in output spectrum shape.

Special methods and apparatus for control and new FDML laser cavity designs are described in the example embodiments to address these problems with FDML operation. Because FDML lasers exhibit low repetition rates, typically less than several megahertz, electronic processing and scaling techniques can be applied to generate the desired control signals. Because different wavelength components are coupled out of an FDML laser at different times, indirect spectral detection by simple light measurement devices may be employed without the requirement for wavelength selective elements. Additionally, if a wavelength selective device such as an optical bandpass filter is used to characterize the FDML output, measurement of time jitter with a simple light measurement device is enough to give access to wavelength jitter and wavelength drift.

Dynamic Optimization of Tunable Filter Control Signals

To ensure consistent and optimal operation of a Fourier Domain Mode Locking (FDML) laser over time, it may be necessary to make periodic or continuous adjustments to the electronic signals controlling operation of the tunable filter element. These control signal adjustments may compensate for environmental changes and drift in component characteristics, which may occur over a wide range of time scales. When a Fabry-Perot filter is used as the tunable filter element, for example, the control signal requiring adjustment may include an AC drive voltage and a DC voltage offset. FIG. 1 illustrates a system 10 that is suitable for FDML operation using resonant frequency tuning.

There are two classes of techniques that can be used to dynamically optimize the tunable filter control signals. In both classes of techniques, one or more measurements may be made on a portion of light that is coupled out of the laser cavity in order to characterize the laser performance. The measured parameter can be a time-averaged intensity measured at one wavelength or a number of wavelengths, a time-averaged intensity averaged over a number of wavelengths, a spectral center wavelength or other spectral property, a phase measurement, or any other suitable characteristic of the light.

a) Feedback Optimization Techniques

Figure 2:
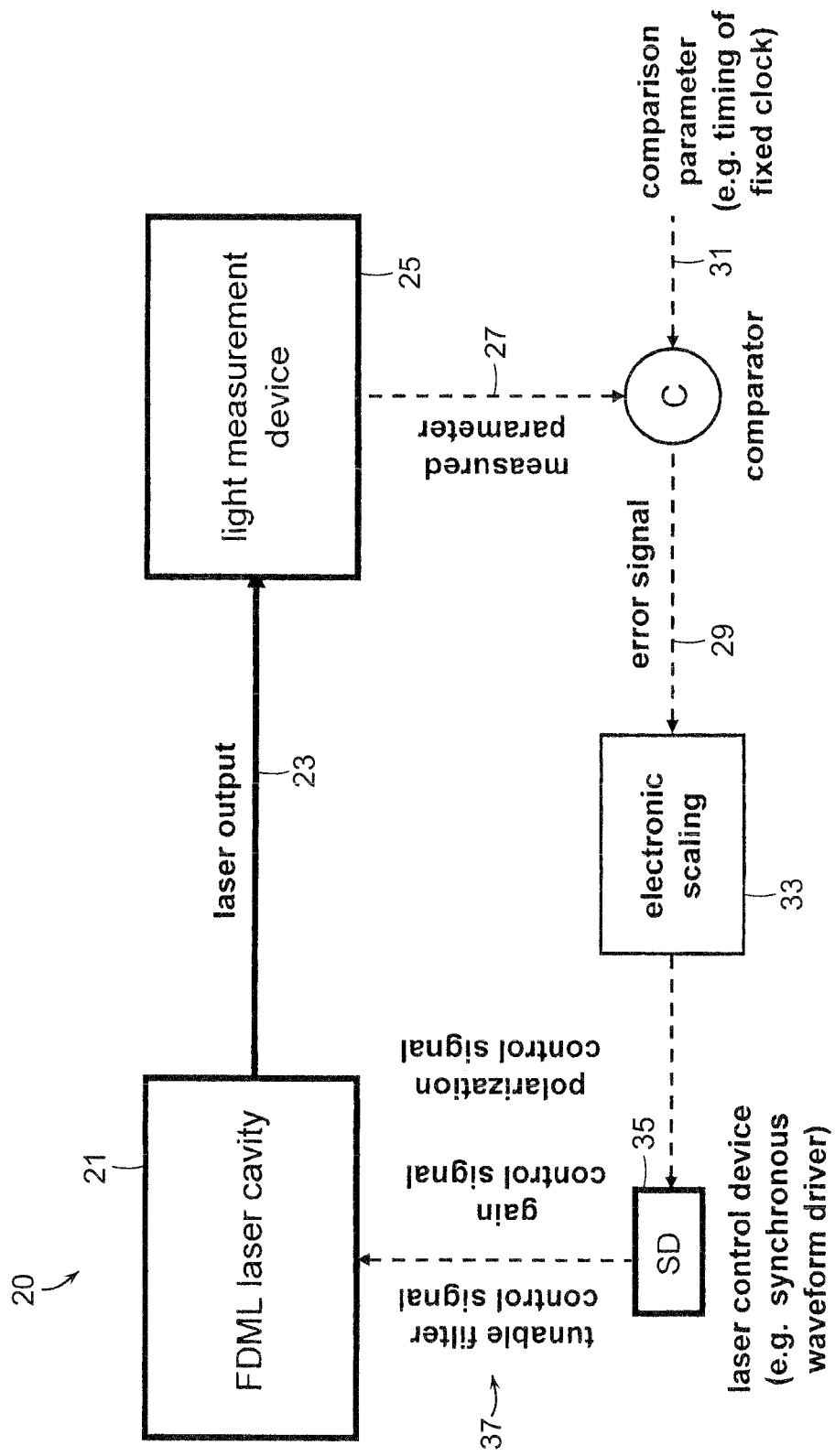
FIG. 2 is a schematic diagram of a control system employing dynamic feedback optimization according to an example embodiment.

FIG. 2 illustrates a control system 20 utilizing the first class of optimization techniques, which can be called "feedback techniques." The control system 20 may include a FDML laser cavity 21 similar to the FDML cavity described in U.S. patent application Ser. No. 11/337,105, filed on Jan. 20, 2006, now U.S. Pat. No. 7,414,779, and U.S. patent application Ser. No. 12/220,898, filed on Jul. 28, 2008, to which this application is a continuation-in-part. A laser output 23 may be coupled from the laser cavity 21 in order to characterize the laser performance. The laser output may be in the form of a periodically wavelength swept light-field. The laser output 23 may be directed to a light measurement device 25. The light measurement device 25 may be a photodiode or any other apparatus known in the art for light detection. The light measurement device 25 may be configured to analyze the laser output 23 in order to determine a measured parameter 27.

In feedback techniques, the measured parameter 27 may be used to generate an error signal 29 by comparing the measured parameter 27 to an operator or predefined comparison parameter 31 via a comparator element C. The comparator element C may be an operational amplifier or any other device known in the art for signal comparison. The comparator element C may perform an electronic arithmetic operation, electronic logic operations, or a combination of both. The comparison parameter C can be a known desired parameter or a previously measured parameter.

Upon comparison, the error signal 29 may be scaled via an electronic scaling unit 33 in order to adjust the error signal 29 to an appropriate power level for inputting into a laser control device (e.g., synchronous waveform driver) 35. The laser control device 35 may be configured to define new settings for control signals 37 that may be used for adjusting the operation of the FDML laser cavity 21. The control signals 37 may be in the form of tunable filter control signals, gain control signals, or polarization control signals, as well as any other FDML parameter that may be adjusted. By repeatedly performing this operation the error signal is decreased to a minimum and the FDML laser will consistently operate in an optimal fashion.

In one illustrative example, the measured parameter could be the time-averaged intensity averaged over a number of wavelengths approximately corresponding to the tuning range of the FDML laser ("output power") or the phase correlation of the FDML laser averaged over a number of sweeps ("phase correlation"). The tunable filter element can be a Fabry Perot, fiber Fabry Perot, or any other filter known in the art. In this case, the error signal could be generated by comparing the current output power or phase correlation to a previously-measured output power or phase correlation. In the event of a decrease in average output power or phase correlation, the magnitude of the error signal would increase. The frequency of the AC drive voltage component of the Fabry Perot filter control signal would then be adjusted so as to minimize the magnitude of the error signal. All specific implementations of a feedback technique could be enhanced by using well-known control system architectures, such as Proportional-Integral-Derivative (PID) feedback loops, to provide stable and rapid responses.

In addition to controlling the frequency of the AC drive voltage component of the tunable filter control signal, it may also be beneficial to control the DC offset component of the tunable filter control signal. The DC offset component adjusts the center wavelength of the range of wavelengths that the tunable filter is tuned over. Therefore control of the DC offset component may be used to ensure that the laser tunes over a desired wavelength range repeatedly over time. Factors such as changing thermal conditions, aging of the tunable filter, changes in the laser gain medium gain spectrum and other effects can all contribute to variations in the center wavelength of the FDML output spectrum. Appropriate control of the DC offset component of the tunable filter control signal can counteract these undesirable effects and stabilize the center wavelength of the output spectrum.

To control the DC offset component of the tunable filter control signal using feedback techniques, the measured parameter or comparison parameter can be one or more wavelengths, one or more times, or some other parameter.

In one illustrative example of a DC offset control technique where the measured parameter is a wavelength, the measured parameter could be the spectral center wavelength of the laser output and the tunable filter element could be a Fabry Perot filter. The light measurement device could be a spectrometer that analyzes a portion of the laser output and determines the center wavelength of the detected spectrum. The comparison parameter could be a known, desired center wavelength. The error signal could be generated by comparing the current center wavelength to the desired center wavelength. In the event of a deviation in measured center wavelength away from the desired value, the magnitude of the error signal would increase. The DC offset component of the tunable filter control signal would then be adjusted, according to the sign of the error signal, so as to minimize the error signal. Variations of this method are possible, such as measuring multiple wavelengths at various positions in the detected spectrum and comparing these to multiple desired wavelengths to form an error signal.

In one illustrative example of a DC offset control technique where the measured parameter is a time, the measured parameter could be the time of arrival of a fixed wavelength or group of wavelengths within the FDML laser output. The light measurement device could include one or more narrowband wavelength selective elements, such as Bragg gratings or other optical bandpass filters, and one or more photodetectors to detect the filtered light. In this way the light measurement device could produce one or more electronic signals that indicate the point or points in time when the fixed wavelength, or group of wavelengths, is produced in the FDML laser output. More specifically, the fixed wavelength could be the desired center wavelength of the FDML laser output and the measured time could correspond to the time at which the center wavelength is produced. Thus, the light measurement device may be configured to detect a transent signal indicating a time when the laser output has a certain wavelength.

The comparison parameter could be a timing signal generated by a fixed clock with a known phase relationship to the tunable filter drive signal. For example, the fixed clock could include electronic pulses generated at the start of each period of the tunable filter drive signal. The comparator could generate the error signal by comparing the time of arrival of the center wavelength to the time corresponding to the start of the tunable filter drive period. For a given tunable filter drive frequency, the difference between the measured parameter and comparison parameter should remain fixed. In the event of a deviation in the measured arrival time relative to the fixed clock, the magnitude of the error signal would increase. The DC offset component of the tunable filter control signal would then be adjusted, according to the sign of the error signal, so as to minimize the error signal.

In a second illustrative example of a DC offset control technique where the measured parameter is a time, the measured parameter could be a difference in the time of arrival of a fixed wavelength within the FDML laser output between a forward and a backward sweep direction. In some embodiments of FDML lasers, the periodic drive waveform applied to the tunable filter produces a forward sweep (shorter to longer wavelengths) and a backward sweep (longer to shorter wavelengths) during each period of the drive waveform. In this case the light measurement device could include a narrowband wavelength selective element, such as Bragg grating or other optical bandpass filter, and a photodetectors to detect the filtered light. The wavelength selective element could be configured to select the desired center wavelength of the FDML output such that the photodiode produces an electrical signal when the desired center wavelength occurs in the forward and backward sweep directions.

Figure 3A:
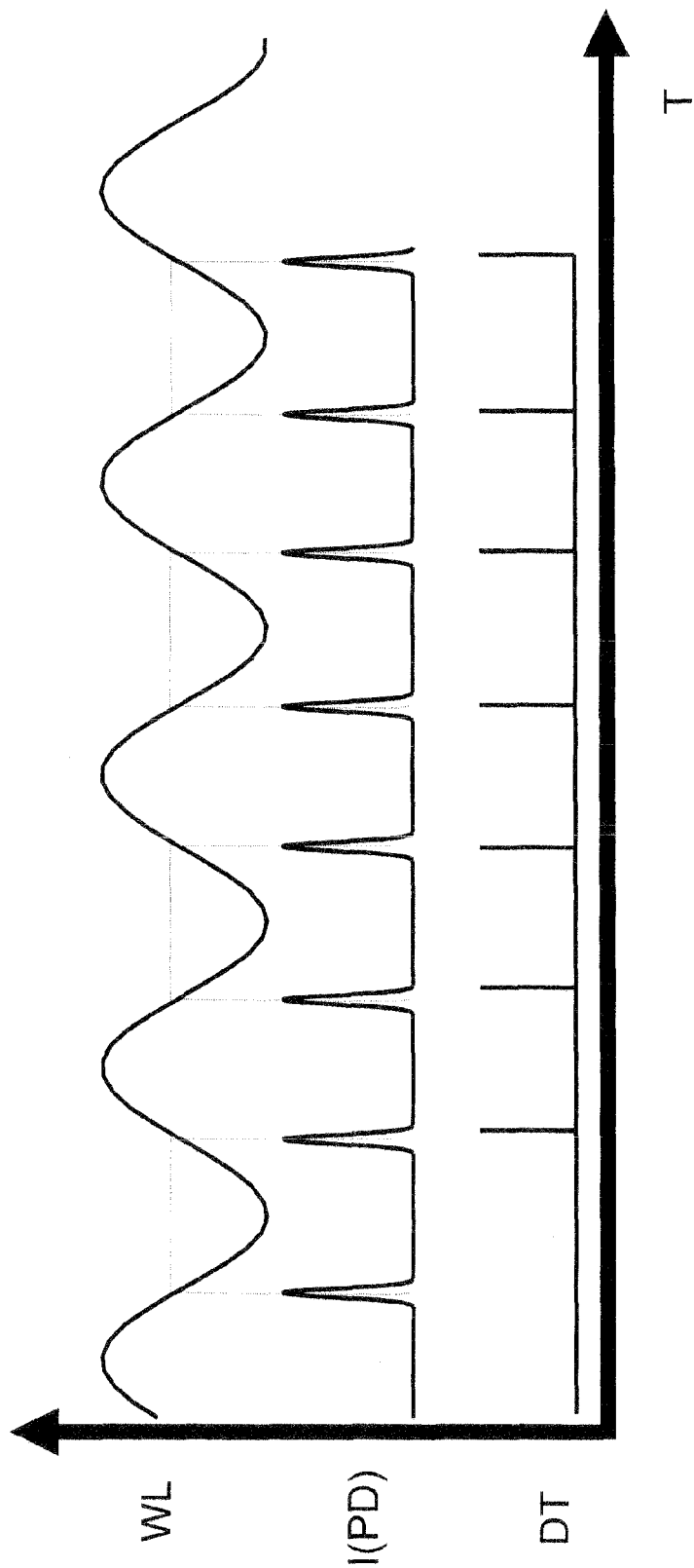
FIGS. 3A and 3B are graphs depicting a measurement of a reference wavelength arrival time.
Figure 3B:
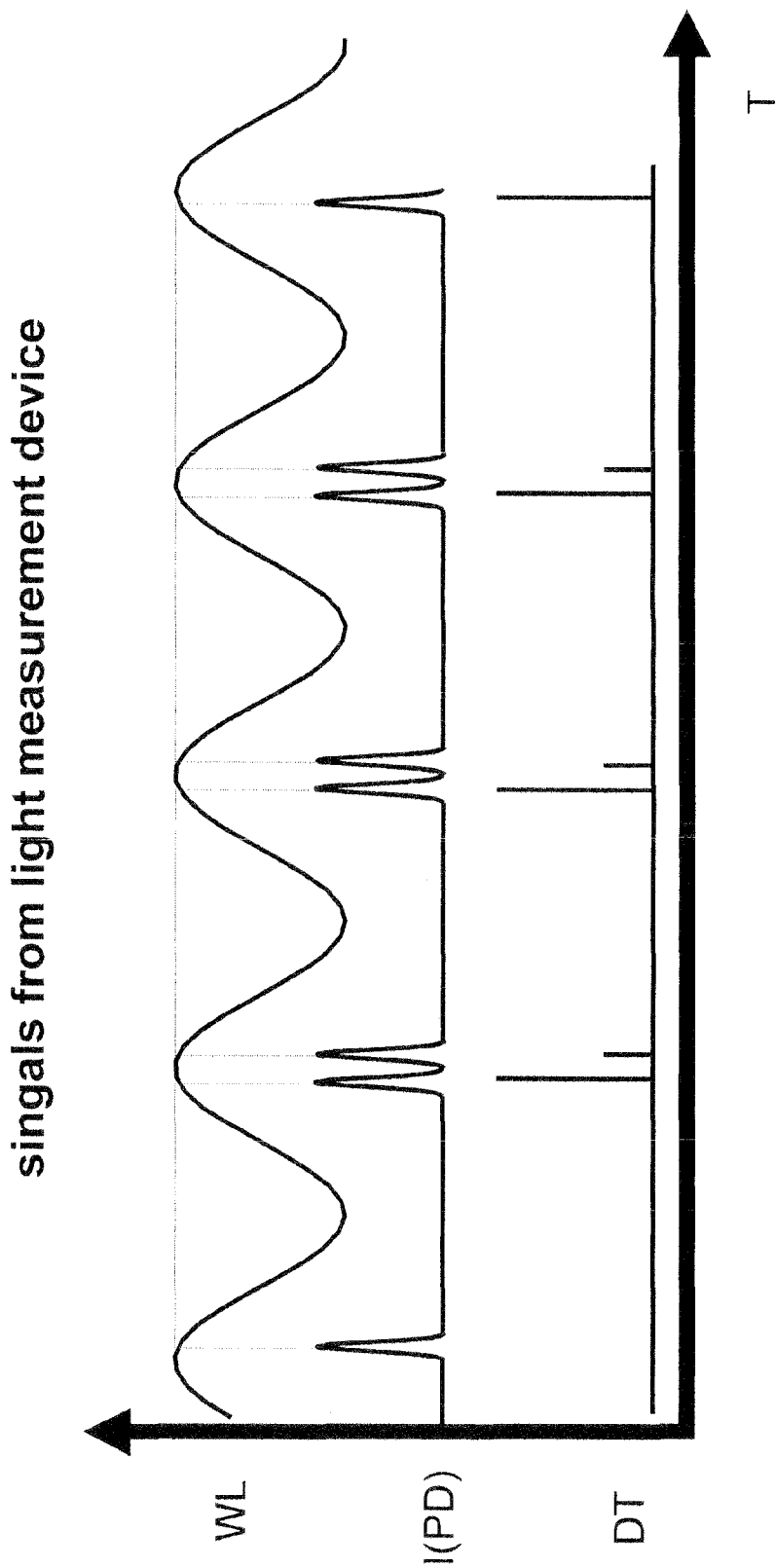

FIGS. 3A-B illustrate the generation of the measured parameter DT for this specific example. The wavelength WL of the FDML laser output varies as a function of time T. The photodetector in the light measurement device produces an electronic signal I(PD) that pulses when the desired center wavelength is produced during the forward and backward sweeps. The measured parameter DT is the difference in the arrival time of one I(PD) pulse and the previous I(PD) pulse. The comparison parameter could be the previous value of the measured parameter, and the error signal could be the difference between the measured parameter and the comparison parameter. FIG. 3A illustrates the case when the laser is operating as desired and the actual center wavelength of the FDML output is equal to the desired center wavelength. The spacing of the I(PD) pulses are equal since the desired center wavelength occurs in the middle of the forward and backward sweeps. Since the I(PD) pulse spacing is equal, each value of DT is substantially the same, each value of the comparison parameter is equal to each value of the measured parameter, and the error signal is zero.

FIG. 3B illustrates the case when the laser is not operating as desired and the actual center wavelength of the FDML output is not equal to the desired center wavelength. The I(PD) pulse spacing is not equal, and consecutive values of DT are therefore not equal. The error signal will be non-zero in this case. The DC offset component of the tunable filter control signal would then be adjusted, according to the sign of the error signal, so as to minimize the error signal.

b) Regenerative Optimization Techniques

Figure 4:
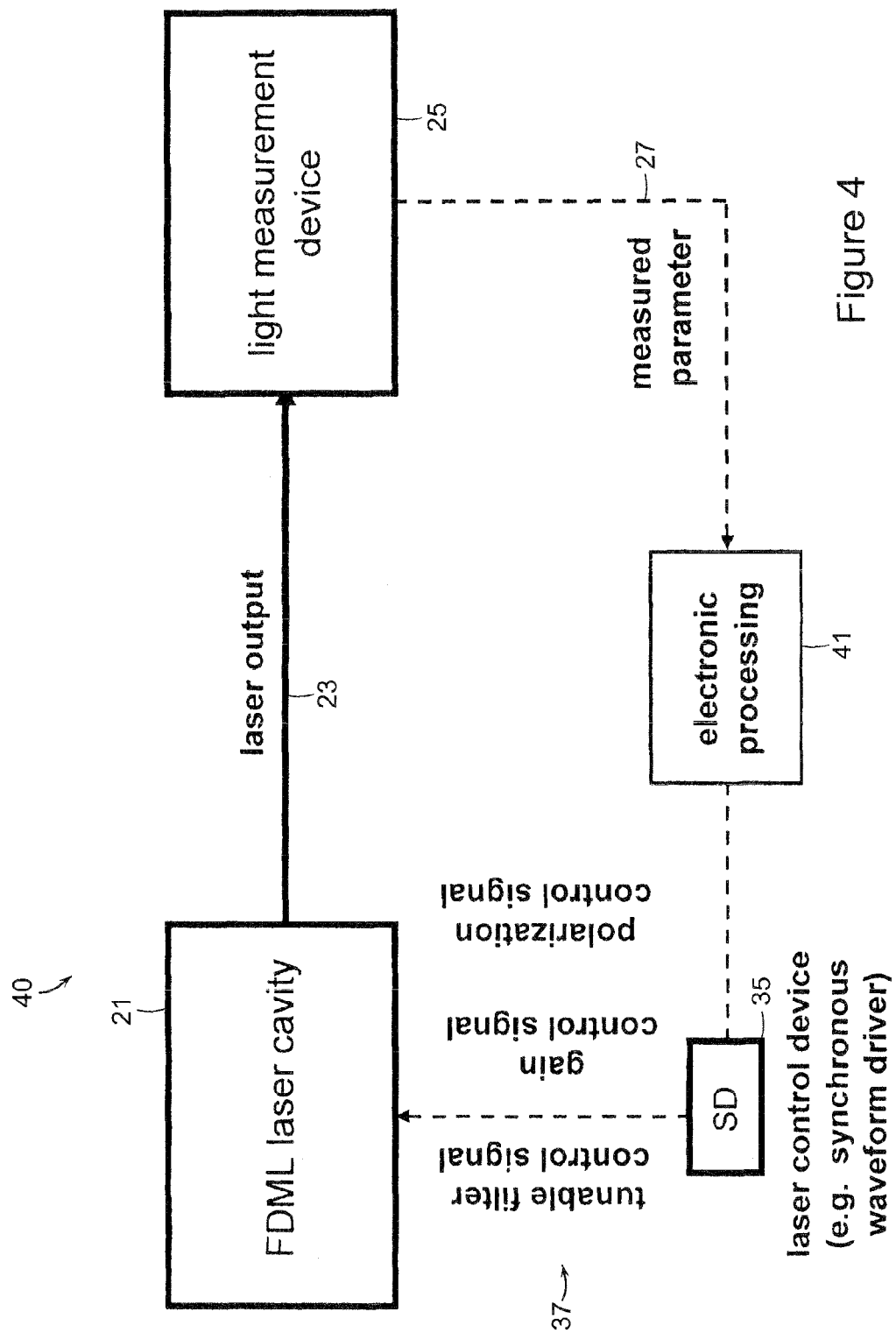
FIG. 4 is a schematic diagram of a control system employing dynamic regenerative optimization according to an example embodiment.

FIG. 4 illustrates another control system 40 utilizing the second class of optimization techniques, which can be called "regenerative techniques." The control system 40 may include a FDML laser cavity 21 where a laser output 23 may be coupled out of the cavity 21 and input into a light measurement device 25. The light measurement device 25 may provide the measurement parameter 27 which may be applied directly to an electronic processing unit 41.

In regenerative techniques, the measured parameter 27 is applied directly to the laser control device 35, which in turn provides a control signal 37, after electronic processing via unit 41. As discussed in relation to FIG. 2, the control signals 37 may be in the form of tunable filter control signals, gain control signals, or polarization control signals, as well as any other FDML parameter that may be adjusted. Thereafter, the control signal 37 may be applied to the tunable filter element within the cavity 21 in order to control the FDML laser operation.

Regenerative optimization techniques have the advantages of simplified control structure and, typically, faster response times to changes in the optimal control signal settings. In this class of optimization techniques, the measured parameter may be appropriately matched to the control signals required by the specific tunable filter element inside the FDML laser cavity. For example, when a Fabry Perot filter is used as the tunable filter element, an AC drive voltage and a DC voltage offset may be used to control the Fabry Perot. The measured parameter may therefore be capable of generating an AC drive voltage and/or a DC voltage offset suitable for controlling the Fabry Perot filter.

In one illustrative example, the light measurement device could be a high-speed photodiode having a bandwidth greater than the frequency corresponding to the roundtrip time of the laser cavity. The measured parameter would be the time-domain radiofrequency (RF) intensity of the FDML laser output. This RF signal may include frequency components corresponding to the roundtrip time of laser cavity, and integer multiples of this frequency. This situation may occur even without FDML lasing operation, for example when no drive signal is applied to the tunable filter element. The electronic processing unit could include an electronic bandpass filter that substantially transmits a range of frequencies centered around the frequency corresponding to the roundtrip time of the laser cavity. The electronic processing unit could further include an amplification stage to ensure that the resulting signal includes sufficient power to drive the tunable filter element. The electronic processing unit could also include the addition of a DC voltage offset in order to specifically drive an Fabry Perot filter. Using this arrangement, variations in the optimal AC drive frequency will be immediately transmitted to the tunable filter element and corrected.

Intelligent Drive Methods for Improving Performance

The tunable filter element and gain medium of an FDML laser can be driven with a variety of waveforms, depending on the specific type of tunable filter element and gain medium. For example, when a Fabry-Perot filter is used as the tunable filter element, one type of drive waveform that may be used is an AC sinusoidal voltage wave with an additional DC voltage offset. When the gain medium is a semiconductor optical amplifier (SOA), a DC current may be used as a drive waveform. It should be noted that other types of drive waveforms can be applied to these elements. Furthermore, waveforms, or modulations of waveforms, may be chosen in order to improve FDML laser performance.

a) Methods for Generating Unidirectional Frequency Sweeps

One undesirable characteristic of some embodiments of FDML lasers is bidirectional wavelength sweeping. Bidirectional sweeping is a consequence of the mode of operation of the tunable filter element. For example, when the tunable filter element is a fiber Fabry-Perot (FFP) filter, the fiber in the filter physically moves forwards and backwards as it is tuned. Consequently, the laser produces wavelength sweeps that alternate in direction from short to long wavelengths ("forward sweeps") followed by long to short wavelengths ("backward sweeps"). As the sweep frequency of an FDML laser is increased, the performance of one sweep direction degrades relative to the other sweep direction. This is also true of previously known conventional swept wavelength laser sources. Thus, in order to prevent the degradation, in example embodiments unidirectional wavelength sweeps may be employed.

Figures 5A, 5B:
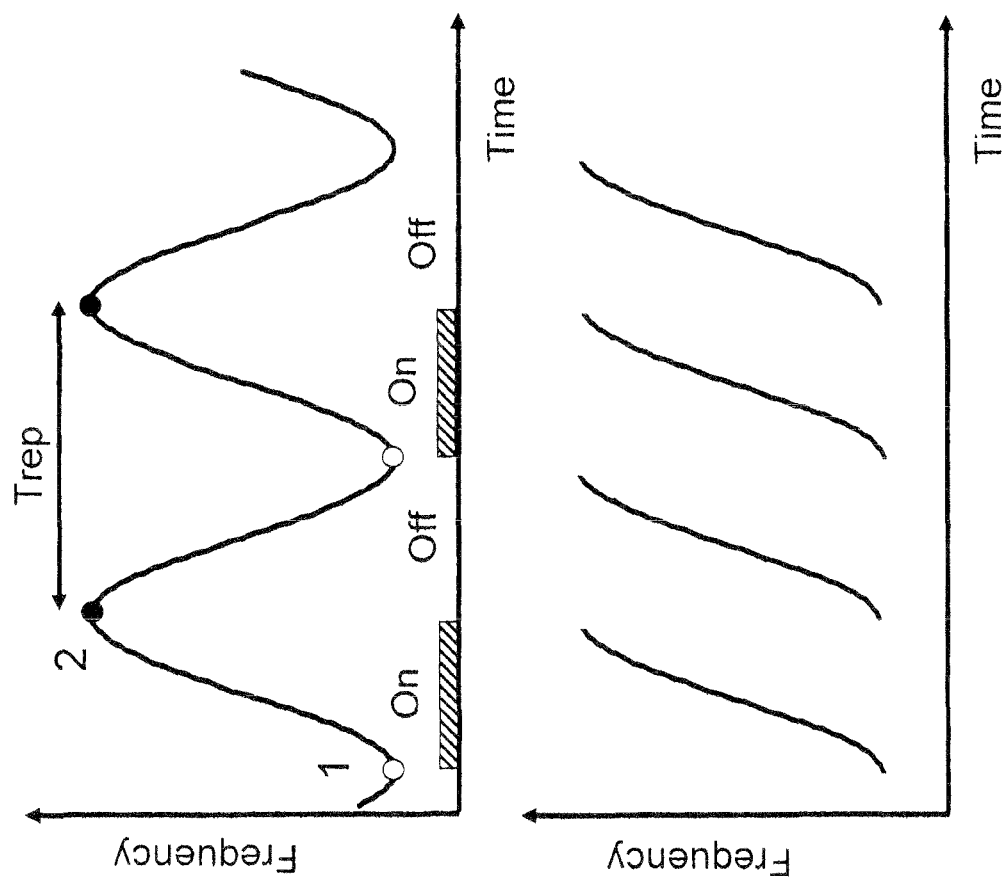
FIGS. 5A and 5B are graphs depicting time multiplexed outputs for a unidirectional system according to example embodiments.

One method for creating unidirectional wavelength sweeps is by breaking the FDML cavity into multiple sections and modulating the gain medium with a rectangular pulse train. As shown in FIG. 5A, a unidirectional frequency sweep can be achieved by time multiplexing, combining the laser output with a delayed version of the laser output and appropriately modulating the gain of the laser. In the example shown, the laser gain is modulated such that output is obtained during the rising edge of the sinusoidal frequency sweep (from point 1 to point 2 on the curve). The laser output is then combined with an output delayed by one half of the laser round trip time ($T_{rep}/2$). This produces the combined output shown in the FIG. 5B in which the frequency sweep occurs at twice the repetition rate of the laser, every $T_{rep}/2$, with the frequency sweep occurring unidirectionally from low to high frequency.

Figure 6:
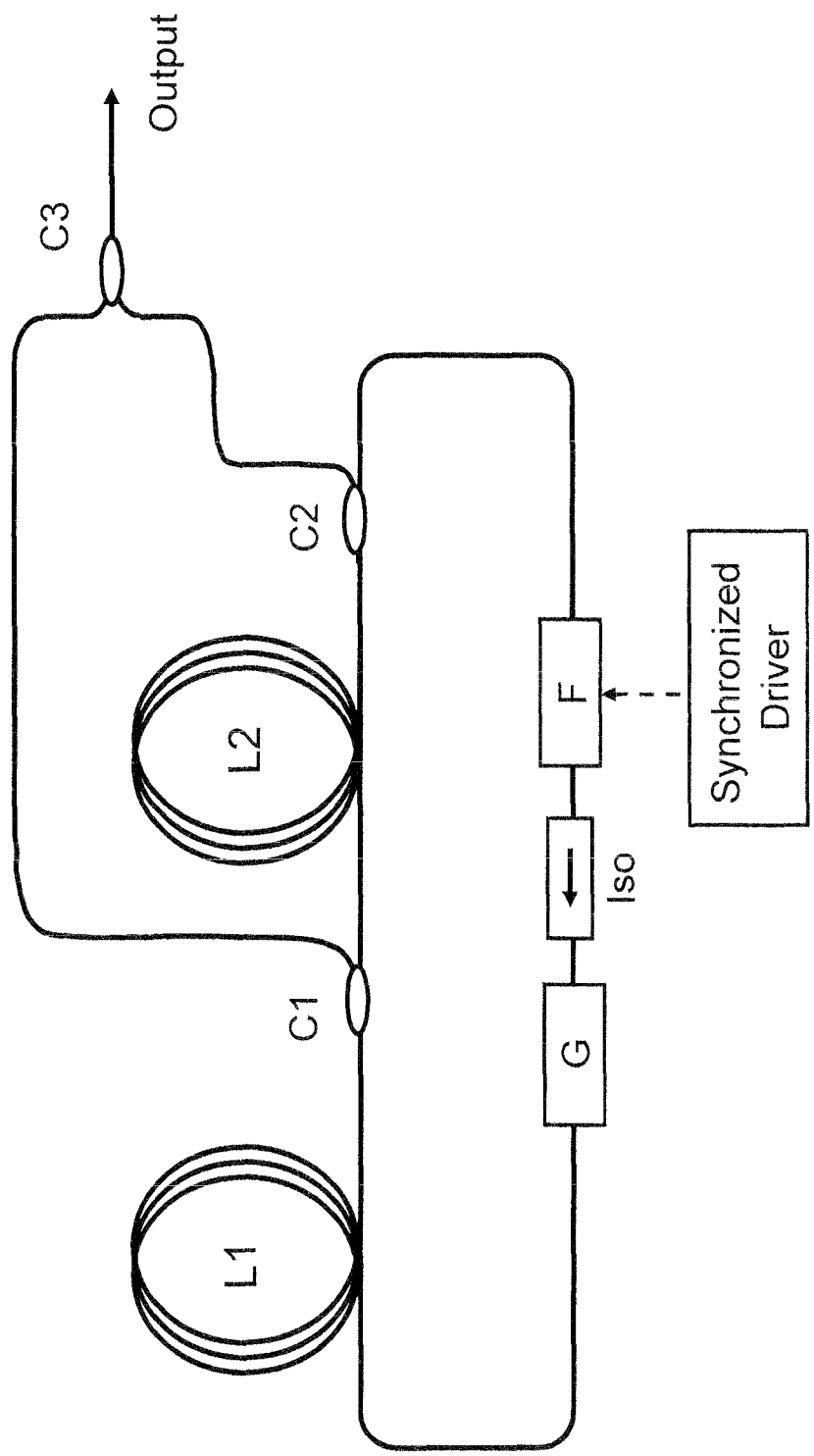
FIG. 6 is a schematic diagram of a ring cavity having time multiplexed outputs according to an example embodiment.

Time multiplexing may be performed by splitting the output of the laser, time delaying one output, and combining them. This action can be performed by devices such as an unbalanced Mach Zehnder interferometer (not shown). However, it is also possible to perform time multiplexing directly from the laser itself. FIG. 6 shows a ring laser configuration which generates two time delayed outputs. The ring laser includes a gain G, filter F, an isolator ISO, with a fiber delay L1, a coupler C1, a second fiber delay L2, a coupler C2, and a combiner C3 which combines the two outputs. This combiner can be a fiber coupler, a polarization beamsplitter, or an active optical switching element, like a Pockels cell with a subsequent polarization beamsplitter assembly. An acousto-optic deflector can also be used for switching between the two ports.

The total round trip delay of the ring is determined by the lengths of the fibers in the two delay lengths L1 and L2, with additional delay from the other components in the ring. The relative delay between the two outputs from couplers C1 and C2 is determined by the length of the fiber delay L2. The coupling ratios of couplers C1 and C2 can be chosen differently in order to equalize the intensities coupled out while accounting for attenuation losses. The coupling ratio of coupler C3 can also be optimized to equalize the intensities combined from the two outputs from couplers C1 and C2. The coupler C3 will have loss of approximately one half when equally combining two outputs. Although this example is shown for two time multiplexed outputs, this cavity configuration can be generalized to time multiplex large numbers of outputs. Polarization controllers (not shown) can be used to ensure that the polarizations of the time multiplexed outputs are included if necessary.

Figure 7:
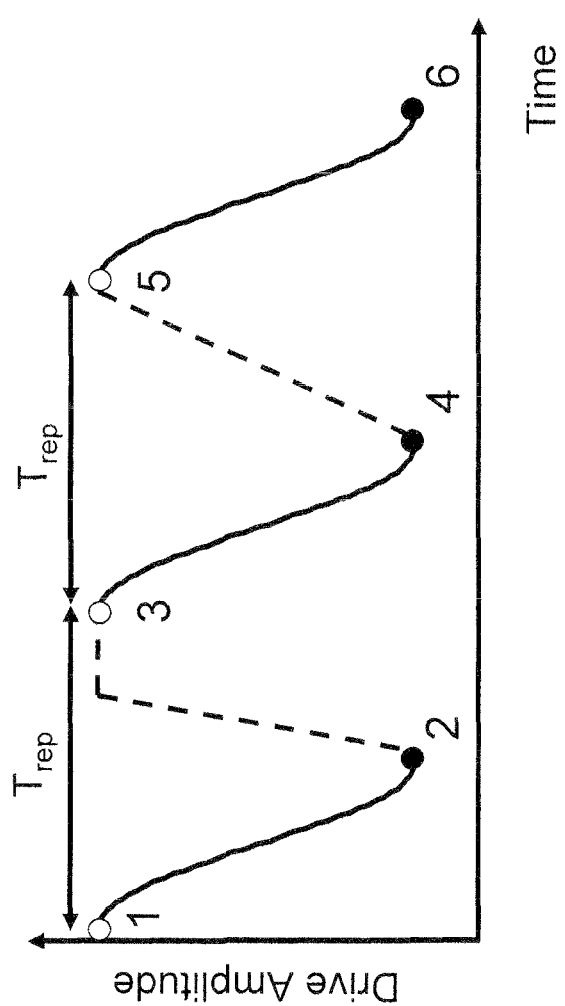
FIG. 7 is a graph illustrating the creation of unidirectional wavelength sweeps with the use of quasi-periodic waveforms according to an example embodiment.

In other example embodiments, as shown in FIG. 7, it is possible to create unidirectional sweeps by applying a quasi-periodic waveform to the tunable filter element. In this arrangement, the portion of the drive waveform responsible for creating the desired sweep direction (such as the first half of a cosine wave) would be applied to the tunable filter element in a periodic manner. In FIG. 7, this is shown by the waveform segments between time points 1-2, 3-4, and 5-6. $T_{rep}$ is the roundtrip time of the FDML laser cavity and the periodic segment of the drive waveform is ½$T_{rep}$ in duration. The portion of the drive waveform responsible for creating the undesired sweep direction (such as the second half of a cosine wave) would be replaced by an aperiodic function. In FIG. 7, this is shown by the waveform segments between time points 2-3 and 4-5. Alternatively, the replacement function could be periodic with a period that is not an integer multiple of the roundtrip time of the cavity. Since FDML lasing operation cannot occur when the tunable filter drive signal is not synchronized to the cavity roundtrip time, lasing will not occur during the time when the replacement function is applied to the tunable filter element.

In contrast to previously known conventional wavelength-swept lasers, the choice of a preferred sweep direction for FDML lasers is non-obvious. In conventional swept lasers the forward sweep direction (sweeping from short wavelengths to long wavelengths) may be preferred since it provides higher output power and lower noise than the backward sweep. This has been consistently observed by numerous groups that are active in the field of work [e.g., Bilenca A et. al., Optics Letters 31, p. 760 (2006); R. Huber et. al., Optics Express, 13(9): p. 3513 (2005)]. However, in example embodiments, with respect to FDML lasers, the backward sweep direction may be preferred since it provides increased phase stability and decreased noise compared to the forward sweep.

b) Methods for Generating a Linear or Arbitrary Optical Frequency Sweep Vs. Time A second undesirable characteristic of some embodiments of FDML lasers is a nonlinear relationship between the instantaneous optical frequency of the laser output and time. For example, when a Fabry Perot filter is used as the tunable filter element and when a sine wave with a DC voltage offset is used as a drive signal, the resulting frequency sweep is also a sine function. In many applications, a nonlinear frequency sweep results in additional signal processing requirement and performance degradation. This occurs because different optical frequencies are present in the laser output for different amounts of time, which can confound time-resolved measurements of the laser output. Data acquisition is also negatively affected since digital sampling time is allocated unevenly to each wavelength.

In interferometric imaging applications such as OCT, a nonlinear frequency sweep makes it necessary to perform an additional processing step to resample the detected interferometric signal onto a grid that has a uniform optical frequency spacing prior to forming an image. For these reasons and others, it is therefore desirable for an FDML laser to create output sweeps where the instantaneous optical frequency is linear with time.

According to example embodiments, there are two classes of techniques that can be used to create a linear frequency sweep with an FDML laser. The first class of linearization techniques can be called "characterization techniques." In characterization techniques, the RF frequency response of the tunable filter element is measured and used to determine a suitable drive waveform for creating a linear frequency sweep. The frequency response can be measured by applying any known electronic test waveform (such as an impulse function or step function) to the filter and then directly or indirectly observing the response of the filter. In the case of a Fabry Perot filter, for example, directly observing the motion of the fiber inside the filter is difficult without disassembling the component. Therefore, in an example embodiment, the filter response could be indirectly observed by passing light with a known spectral shape through the filter and observing the output as a function of time when the test waveform is applied.

Another method to characterize the frequency response of the Fabry Perot filter is to use an RF spectrum analyzer to determine the electronic frequency response of the Piezoelectric Transducer (PZT) or other actuating element of the Fabry Perot filter. Using known theoretical models, the RF amplitude and phase spectrum can be used to predict the mechanical response.

A further way to determine the mechanical response directly, according to yet another example embodiment, would be to couple a broadband light source into the Fabry Perot filter and measure the time averaged transmitted spectral intensity at a given drive frequency with a spectrometer. The width of the transmitted spectrum yields the amplitude response. Using a monochromator and a fast photodiode allows measurement of the mechanical and optical phase response. One possible procedure for this measurement is to set the monochromator to the center position of the Fabry Perot filter without applying an AC drive waveform to the Fabry Perot filter. The Fabry Perot filter is then set to a known spectral offset. The light transmitted through both the Fabry Perot filter and the monochromator is then measured using a time resolved measurement. The measured time shift between the applied electronic drive signal and the detected light intensity yields the phase shift between the electronic drive signal and the optical transmittance or mechanical response of the Fabry Perot filter. Performing the described measurement at different wavelengths would substantially characterize the amplitude and the phase of the mechanical response of the Fabry Perot filter.

Once the frequency response of the tunable filter element is known, the drive waveform required to create a linear optical frequency sweep can be obtained, according to example embodiments, by dividing the frequency transform of the desired sweep by the frequency response of the filter. This drive waveform can then be synthesized by an analog or digital waveform synthesizer. More advanced calculations using the frequency response of the tunable filter element can provide further performance benefits. Some examples of these benefits include compensation of non-linearities in the filter response, compensation of hysteresis effects in the tunable filter, compensation of aging effects in the tunable filter, and compensation of thermal and mechanical drift in the tunable filter.

Figure 8:
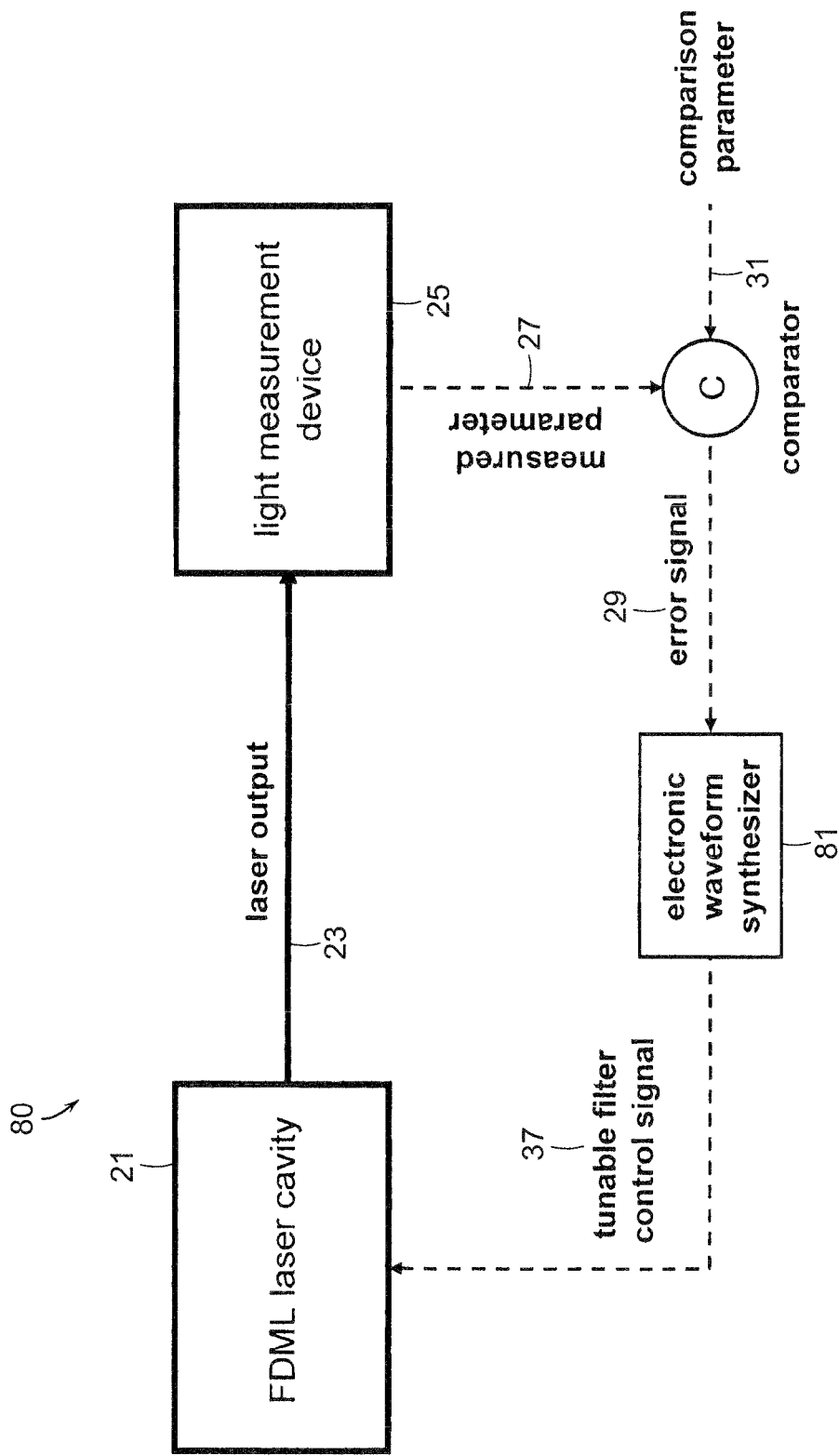
FIG. 8 is a schematic diagram of another control system employing dynamic feedback optimization according to an example embodiment.

In other example embodiments, the second class of linearization techniques may be referred to as "feedback techniques" and is illustrated in the control system 80 of FIG. 8. In the control system 80 of FIG. 8, a laser output 23 may be coupled from a FDML laser cavity 21. The laser output 23 may be input to a light measurement device 25. The light measurement device 25 may be used to produce a measured parameter 27 that may be input to a comparator C. In the feedback techniques, a parameter or combination of parameters of the FDML laser output is measured by a light measurement device 25 in order to characterize the linearity of the sweep.

The parameters 27 may be compared to a known desired parameter or a previously measured parameter, known as the comparison parameter 31, in a comparator C. The comparator may be configured to generate an error signal 29, which is then input into an electronic waveform synthesizer 81. The waveform synthesizer 81 may be configured to create a tunable filter control signal 37. The tunable filter control signal 37 may be input to the FDML laser cavity 21 in order to create a new filter drive waveform based on the error signal 29 and the control signal 37, such that subsequent error signals are reduced and subsequently minimized.

In an illustrative example of a feedback technique for sweep linearization, a portion of the energy coupled out of the laser can be directed to a periodic filter such as a Michelson interferometer or Mach-Zehnder interferometer. The output of the periodic filter may include an oscillating component that encodes the phase evolution of the sweep and therefore the linearity of the sweep. The output of the periodic filter can be detected by a photodiode, and the resulting electronic signal analyzed by a radiofrequency (RF) spectrum analyzer. The light measurement device therefore includes the periodic filter, photodiode, and RF spectrum analyzer. The measured parameter could be the spectral width of the RF spectrum, which decreases as the sweep becomes more linear. In this case, the comparison parameter could be a previously-measured value of the spectral width. The electronic waveform synthesizer could function by combining a series of scaled and phase-shifted signals at a number of electronic frequencies. These signals could form a Taylor series expansion of a higher-order signal, or could be harmonics of the cavity roundtrip time. The amplitude and phase shift of each signal would be optimized in series, such that the parameters for one frequency component would be optimized before proceeding to the next frequency in order to maintain a stale optimization process. By adding these scaled and shifted signals at different frequencies, the error signal can be sequentially reduced and minimized, resulting in a maximally linear optical frequency sweep.

c) Methods for Compensation of Dispersion in the FDML Laser Cavity

A third undesirable characteristic of some embodiments of FDML lasers is reduced performance due to the effects of chromatic dispersion. These effects can include reduced bandwidth, increased noise, and decreased average output power. The main affect of chromatic dispersion in the FDML laser cavity is to cause different wavelength components to propagate at different speeds. For example in the 1060 nm wavelength range, when a standard single mode optical fiber, such as Corning HI-1060, is used in the cavity, the shorter wavelengths propagate more slowly than the longer wavelengths. It is therefore not possible to synchronize the sweep time of the tunable filter element to the propagation times of all wavelengths active in the laser by using a simple drive waveform such as a sine wave. The undesirable effects of chromatic dispersion become worse as the length of the FDML laser cavity is increased, or as the operating wavelength of the laser is moved away from the zero dispersion point of 1310 nm in standard optical fibers. Since it is often desirable to operate FDML lasers at wavelengths significantly distant from 1310 nm, such as the regions around 800 nm, 1060 nm, and 1550 nm, it is necessary to provide techniques for overcoming the limitations of chromatic dispersion.

Figure 9:
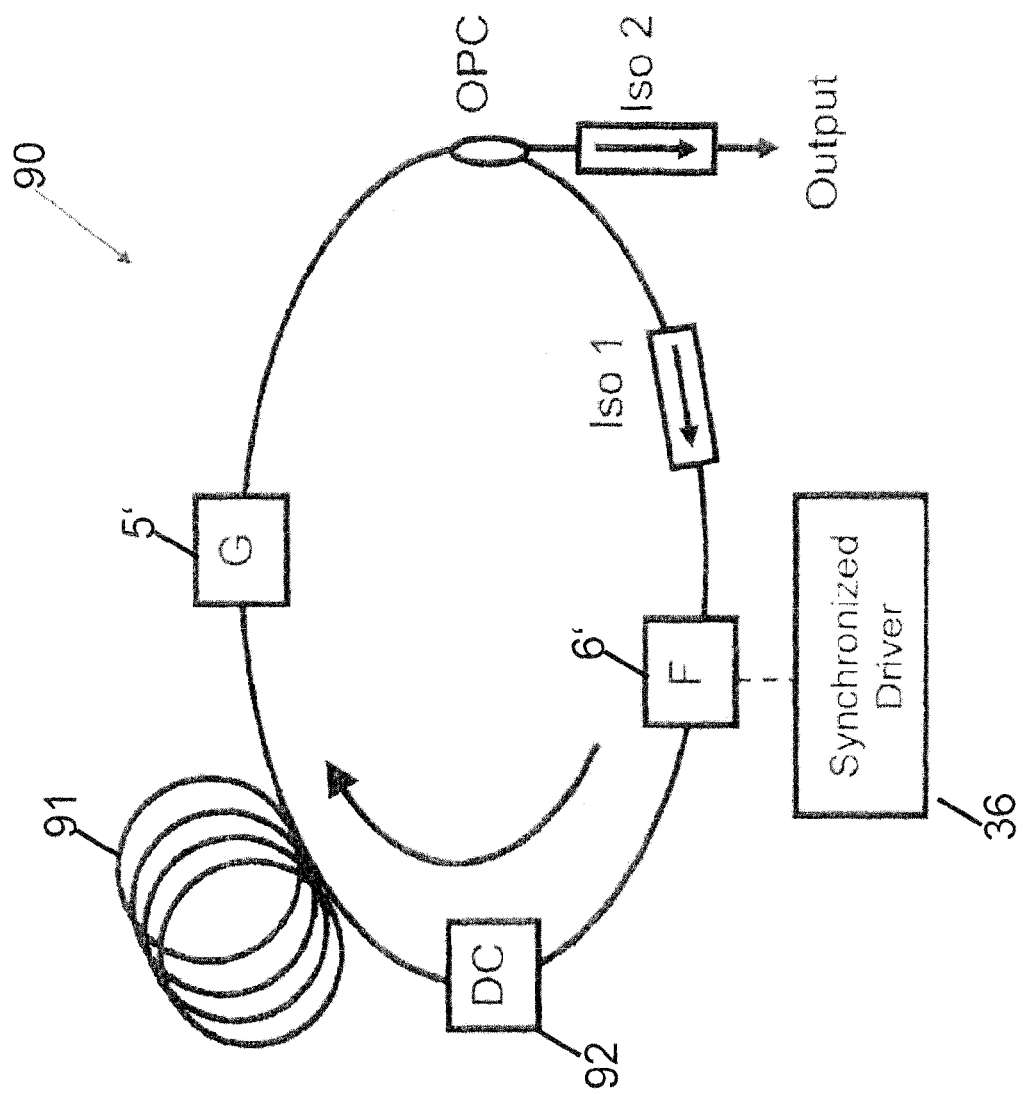
FIG. 9 is a schematic diagram of a laser system featuring a dispersion compensator for dispersion management according to an example embodiment.

It should be noted that it is possible to reduce the effects of chromatic dispersion using optical methods and certain FDML cavity designs as illustrated in FIGS. 8 and 9.

FIG. 9 shows a laser system with dispersion compensation 90. The residual group-velocity dispersion (GVD) causes round trip time mismatch of the different frequency components. Frequency components, which have a round trip time that is different from the interval time of the scanning filter (F) 6' driven by the synchronized waveform driver 36, cannot pass through the filter. Therefore, the residual GVD reduces the optical bandwidth of the swept source. The minimization of the residual GVD in the laser cavity is important to achieve a broad spectrum operation. The GVD of the laser cavity is induced by the employed optical components, such as the optical filter, amplifier/gain (G) 5', and delay line 91. A dispersion compensator (DC) 92, such as the dispersion compensation fiber, chirped fiber Bragg grating, and grating pair, prism compressors, acousto optic or liquid crystal based shaper devices, can reduce the GVD effect, if they are placed in the laser cavity. Multiple DC elements can be used to achieve a defined evolution of the waveform inside the cavity to manage the local intensity.

Figure 10:
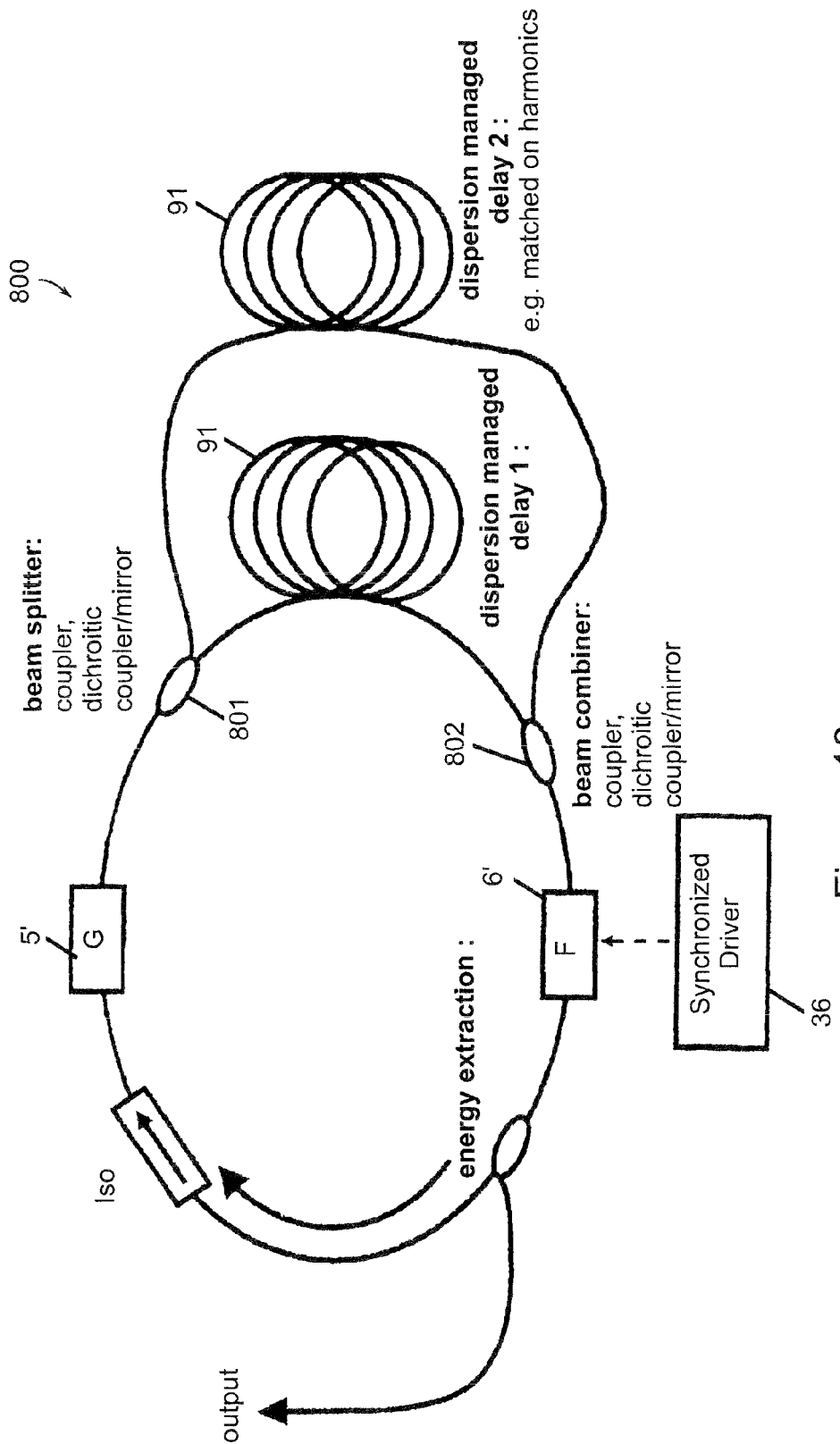
FIG. 10 is a schematic of a laser system featuring multiple delay elements for improved dispersion compensation and/or mixed feedback.

FIG. 10 shows a system 800 having different delays 91 within the cavity. The filter 6' is driven by the synchronized waveform driver 36 in FDML operation mode. Light propagating through the filter is amplified by the gain medium 5'. The light in the cavity is split into two or more separate paths, for example by a dichroic splitter or other coupler 801, and then combined by a beam combiner 802. This approach can be used for better dispersion management, if different wavelengths travel in the different paths whereby the total dispersion in both paths is different. Also, this multiple delay based concept can allow for better compensation of higher order dispersion. Another application of this concept occurs when the roundtrip time in one arm matches the sweep period and the other matches a multiple (e.g. two times) the sweep period. This would result in a mixed feedback from one sweep to the next, as well as to the one after the next. For this reason a better phase stabilization can be expected, as an averaging effect in the feedback is achieved.

Figure 11:
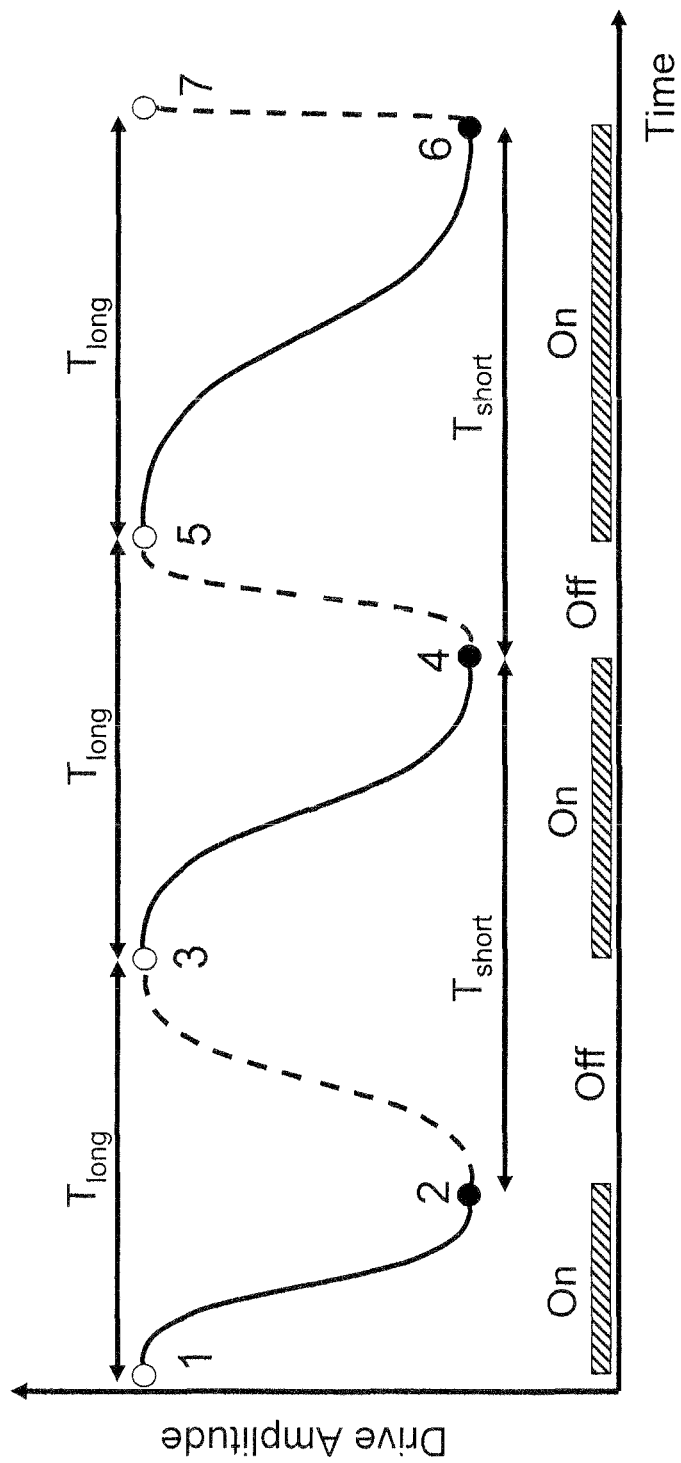
FIGS. 11 and 12 are waveform diagrams graphically illustrate use of drive waveforms where the waveform duration is sequentially altered to compensate for dispersion in the FDML laser cavity according to example embodiments.

In example embodiments, it is also possible to reduce the effects of dispersion by altering the drive waveforms applied to the tunable filter element and gain medium. FIGS. 10 and 11 illustrate the concept of using drive waveforms where the waveform duration is sequentially altered to compensate for dispersion in the FDML cavity.

The tunable filter drive waveform in FIG. 11 is shown as curved line segments. The state of the gain medium (on or off) is shown by dashed boxes. It should be appreciated that a similar method could be applied for bidirectional sweeping. In FIG. 11, $T_{long}$ represents the cavity roundtrip time for the longest wavelength in the sweep. $T_{short}$ represents the cavity roundtrip time for the shortest wavelength in the sweep. FIG. 11 represents the case for an FDML cavity where $T_{short}$ is larger than $T_{long}$ ("normal dispersion") but a similar method could be applied when $T_{long}$ is larger than $T_{short}$ ("anomalous dispersion"). FIG. 11 also represents the case when the longest wavelength in the sweep is generated at the beginning of each drive segment, corresponding to time points 1, 3, 5, and 7. FIG. 11 also represents the case when the gain medium is modulated to create unidirectional sweeps, although this is not necessarily required.

Figure 12:
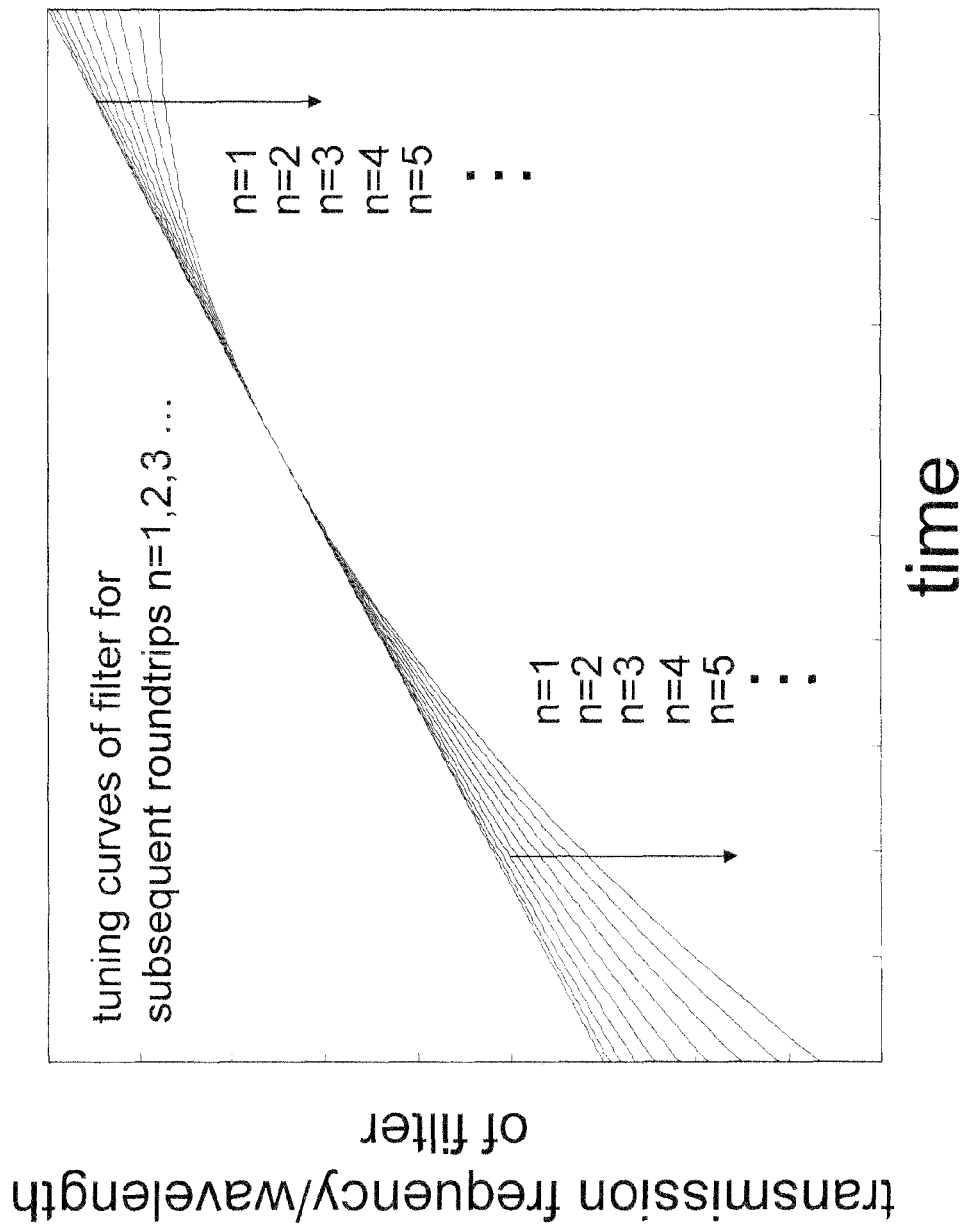

In order to compensate for dispersion in the cavity, the length of the tunable filter drive waveform segments are altered with each successive sweep. The exact manner in which the segments are stretched or compressed depends on the dispersion characteristics of the FDML cavity. For example, if the FDML cavity includes a length of Corning HI-1060 optical fiber and the laser is operating at a center wavelength around 1060 nm, then the laser may operate in the normal dispersion regime. Therefore, in the case of a backward sweep (longer to shorter wavelength) each drive segment needs to be stretched relative to the previous segment, with the exact stretching profile determined by the shape of the dispersion curve. The result is that for a finite number of drive segments, the filter returns to the same position as each wavelength in the sweep reaches the filter input. The filter therefore is synchronized to the cavity roundtrip time for each wavelength, regardless of dispersion, for a finite time period. FIG. 12 is a further visualization of this concept, showing the drive waveform versus time for successive sweeps.

In the case of normal dispersion, the longest wavelength in one sweep eventually arrives at the tunable filter input at the same time as the shortest wavelength from the previous sweep. In FIG. 11, this effect can be seen by the continuous reduction of the time available to move the filter while the gain medium is off (time segments 2-3, 4-5, and 6-7). At this point the drive waveform based dispersion compensation technique reaches a limit, and the waveform must be reset. During a reset event, lasing will temporarily collapse and must build up again over several sweeps. The number of sweeps between reset events depends on the dispersion characteristics of the cavity, but in most cases is sufficiently large for practical use. In optical coherence tomography (OCT) applications, the reset event can be timed during the flyback of the beam scanning galvanometers of the imaging setup. In this manner, no additional time is required for acquiring a series of two dimensional OCT images since OCT image data cannot be collected during the galvanometer flyback.

An equivalent technique is possible when $T_{long}$ is larger than $T_{short}$ and the FDML laser is operating in the anomalous dispersion regime. In this case, each tunable filter drive waveform segment becomes progressively shorter for a backward sweep and vice versa for a forward sweep. A limit is reached when the shortest wavelength from one sweep reaches the tunable filter input at the same time as the longest wavelength from the previous sweep. This situation may also employ a reset of the drive waveform and lasing to build up again in the FDML cavity.

"Polarization Chromaticity" Control

FDML lasers exhibit a very unique and unusual behavior with respect to their polarization properties. Unlike the case in continuous wave (cw)-(fiber)-lasers or pulsed (fiber) lasers, where the main problem with polarization management are thermal drift effects, acoustic vibrations and changing stress in the optical components (fiber), in FDML lasers an inherent and repeatable change of the polarization state depending on the wavelength is observed. So unlike the case in standard lasers, where the entire output polarization changes in time, in FDML the output polarization changes as wavelength or frequency are swept (usually with only minor temporal drift). This effect is herein referred to as polarization chromaticity. Polarization chromaticity may be caused by the unique combination of high order delay between the polarization components after propagation through the delay, and the effect of long instantaneous coherence length. In standard lasers, such as cw-(fiber)-lasers (monochromatic or swept) or pulsed fiber lasers, known devices such as wave plates, fiber squeezers, Faraday elements, etc. can be used to manage these polarization effects. However, in FDML lasers because of the unique effect of high order delays of the orthogonal polarization states, the polarization chromaticity; different methods and apparatus may be needed to manage said effects.

In FDML lasers a defined management or control of the polarization state of the light is highly desired to counteract, cancel or avoid polarization chromaticity. It can be useful to manage or eliminate polarization chromaticity because there are polarization dependent components inside the lasers (such as polarization dependent gain of the laser gain medium [e.g. in an SOA] or polarization dependent transmission or group delay in the other active or passive components of the laser, such as isolators, filters, delay line fiber, couplers etc.). A further reason for controlled polarization chromaticity of the laser can arise from the measurement system in which the FDML laser is used. For example, in OCT setups either a completely polarized or a completely unpolarized output is desired in order to provide insensitivity to fiber bending or to give polarization dependent image contrast or reduced speckle noise.

a) Chromatic Polarization Rotation/States in FDML Lasers

As described above, most known (fiber-)lasers polarization problems are limited to random polarization fluctuations due to temperature fluctuations, changing stress and birefringence in the fiber, or acoustic vibrations, etc. Most often, all wavelength components of a spectrally broad laser (e.g. short pulse laser) are affected in the same way. In FDML lasers, however, a different and very unusual behavior is observed. After propagation through the fiber, the polarization state shows a periodic, wavelength dependent, reproducible modulation. This unique polarization effect, the polarization chromaticity, is most likely caused by an effect which could be described as "chromatic polarization mode dispersion" (chromatic PMD) in the fiber delay. This effect is unique to FDML lasers because of they often use a long intra cavity fiber loop and there is a simultaneously wide spectral range of output wavelength components. Spectrally broad pulsed fiber lasers do not typically have an extremely long fiber of several kilometers length inside the cavity. While standard PMD is well known, the influence of "chromatic PMD" or polarization chromaticity on narrowband tunable lasers, is unique to FDML lasers.

The following methods and apparatus, according to example embodiments, provide ways to manage the polarization inside the laser, especially ways to compensate the observed effect of "polarization chromaticity" and provide a defined output polarization state. A completely un-polarized output could also be desired, and in this case the randomization time scale, usually meaning the time scale on which the polarization state is substantially rotated through the Poincaré sphere, should be shorter than the data acquisition gating interval (measurement time for one data point).

b) Active Methods for Stabilization and Control of Polarization and "Polarization Chromaticity"

Figure 13:
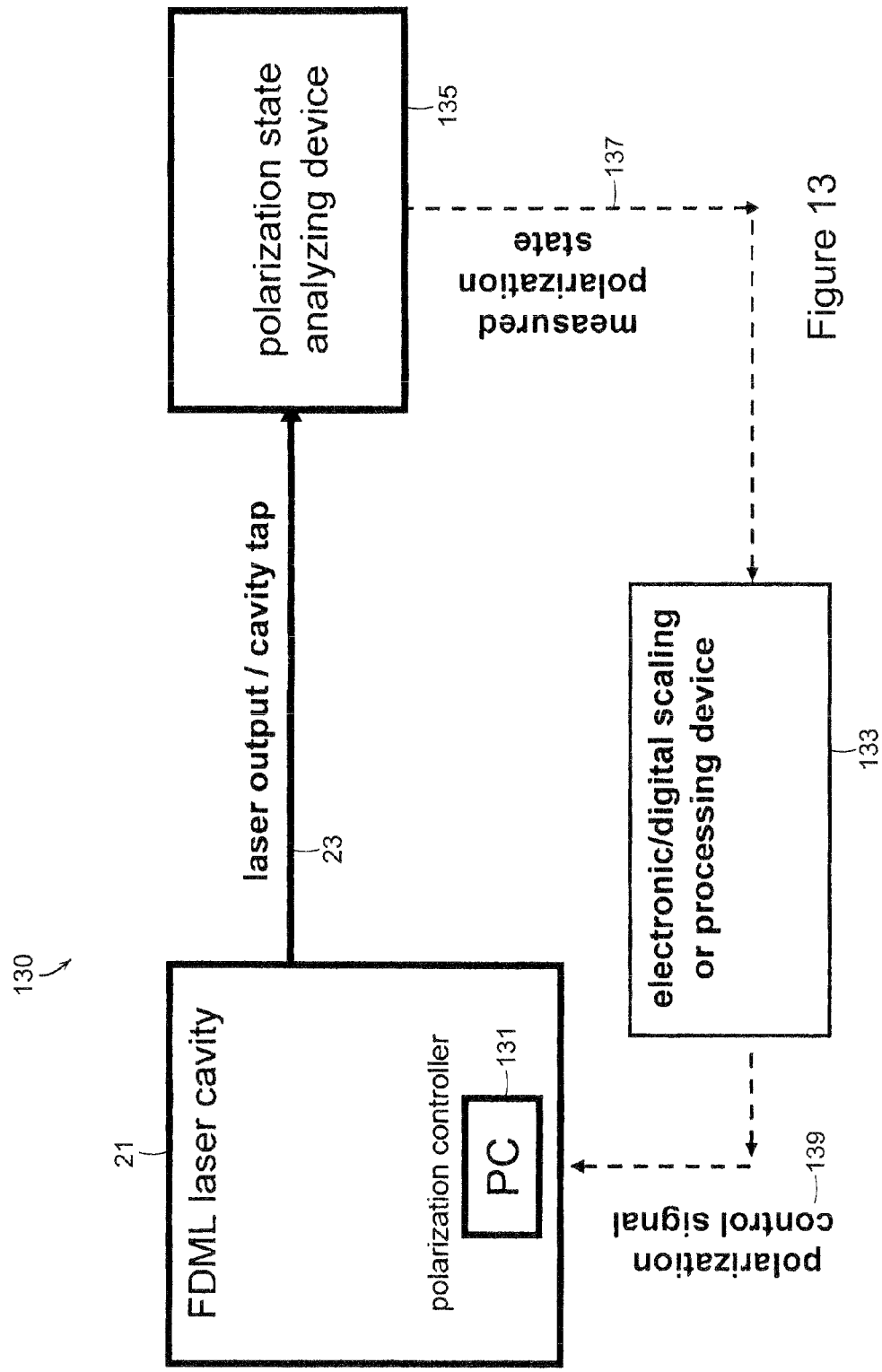
FIG. 13 is a schematic of a control system employing active methods of polarization chromaticity management according to example embodiments.

The first class of methods which provide a defined polarization output would relate to active methods for polarization control. FIG. 13 shows a schematic of a control system 130 utilizing the steps of this method. The control system 130 features a FDML laser cavity 21. The FDML laser cavity 21 may further incorporate an intra- or extra-cavity polarization controller (PC) 131, which can be adjusted over time, usually with an electronic signal. This controller could be, but is not limited to the group including PZT based fiber squeezers, motorized fiber loop paddles to introduce half and quarter wave delays between the two orthogonal polarization states, or electro optic polarization controllers. In general the PC could be any device which can introduce a variable rotation or change of the polarization state of the incident light field.

A laser output or cavity tap 23 may be coupled out of the FDML laser cavity 21. The control system may further incorporate a polarization state analyzing device 135, which can be, but is not limited to a combination of polarizers, waveplates and photodiodes. The analyzing device 135 may receive as an input the laser output or cavity tap 23 and may provide, usually electronic, signals 137 related to the instantaneous polarization state of the light field. The signal is fed into a scaling or processing device 133 which generates a control signal 139 for the polarization controller (PC) 131. Upon receiving the control signal 139, the PC may utilize at least four methods of polarization control, as described below, according to example embodiments.

i) Intra-Sampling Control Method

In the intra-sampling control regime, the time scale on which the polarization control operates, meaning the time scale on which the PC control circuit can generate a substantial change of the polarization state, is shorter than one sampling interval or the inverse detection bandwidth of a measurement system using the FDML laser. Such a mode of operation is may be used in order to generate a quasi depolarized light and the PC must be very fast.

ii) Intra-Sweep Control Method

In the intra-sweep control regime, the time scale on which the polarization control operates, meaning the time scale on which the PC control circuit can generate a substantial change of the polarization state, is longer than one sampling interval or the inverse detection bandwidth of a measurement system using the FDML laser but is shorter than the sweep duration.

This method may be used to compensate the "polarization chromaticity" typical for FDML lasers, referring to the variation in the polarization state as a function of wavelength or frequency over one sweep.

iii) Inter-Sweep Control Method

In the inter-sweep control regime, the time scale on which the polarization control operates, meaning the time scale on which the PC control circuit can generate a substantial change of the polarization state, is longer than one sampling interval or the inverse detection bandwidth of a measurement system using the FDML laser and does not act on the sweep itself, but on the next sweep. The bandwidth of the PC can be comparable to the one in the case of the "intra-sweep method," however a delay in the circuit enables that the signal from the polarization analyzer from one sweep acts on the PC for the next or a later sweep. The feedback is not in between the sweeps, but between one sweep and a later one.

iv) Long Term Control Method

In the long term control regime, the time scale on which the polarization control operates, meaning the time scale on which the PC control circuit can generate a substantial change of the polarization state, is longer than one sweep period. Such a system would be used in the case where long term thermal drift effect should be compensated. Typically the controller would act on an averaged signal of many sweeps and adjust the degree of polarization rotation slowly.

c) Passive Methods for Stabilization, Control, and Management of Polarization and "Polarization Chromaticity"

Figure 14:
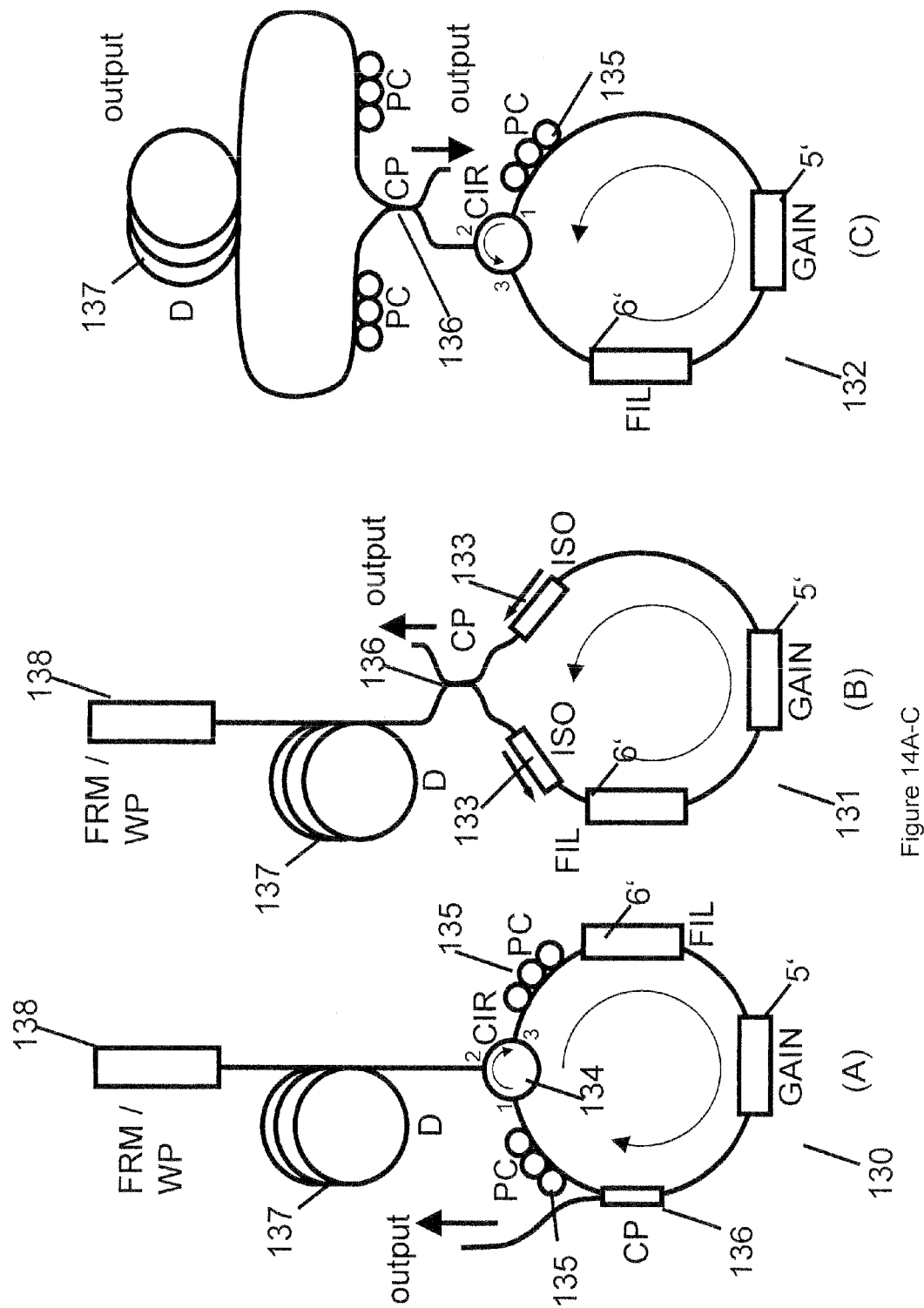
FIGS. 14A-14C are schematic diagrams of laser cavity designs used for the passive minimization of polarization chromaticity according to example embodiments.

The second class of methods in order to provide a defined polarization output relates to passive methods for polarization control. A special choice, design and network of the optical components in the laser are used to achieve the desired effect. The following methods are used to minimize the unique polarization problems of an FDML laser, the polarization chromaticity. The measures for polarization management differ from standard polarization management methods, because the FDML laser is neither a short pulse laser, with a short instantaneous coherence length, nor a monochromatic cw-laser. It is well know that polarization dependent optical components such as depolarizers work either with cw light or with broad band light sources. The following methods are appropriate and used to mange the polarization with passive devices or with special design methods.

i) Special Cavity Designs:

The first class of methods which minimize the polarization chromaticity is depicted in FIGS. 14(A)-14(C). Three exemplary systems 130, 131, and 132 are shown. The special cavity designs provide a reduction of polarization chromaticity. The cavity designs incorporate at least one gain medium (GAIN) 5', at least one optical filter (FIL) 6', optional isolators (ISO) 133 or an optical circulator (CIR) 134, optional polarization controllers (PC) 135, a beam-splitter/coupler element (CP) 136, a delay element (D) 137, an optional Faraday mirror FRM or a wave-plate (WP) 138.

The design of FIG. 14(A) shows an example embodiment of an FDML laser in the form of a "sigma ring" cavity. In a specific example embodiment, the filter (FIL) 6' may be a Fabry Perot filter, the gain medium a semiconductor optical amplifier or a doped fiber. The fiber type may be a single mode fiber, to prevent walk off and mode dispersion in the cavity. However, one or more short lengths of multi mode fiber can help to create an effect of polarization scrambling and generate quasi-non polarized light. The laser is operated as described with a high degree of synchronization between the optical roundtrip time and the filter drive period. The Faraday mirror or waveplate 138 at the end of the linear delay switches the two orthogonal polarization states and provides a compensation of the polarization chromaticity when the light propagates in the backward direction.

The design illustrated in FIG. 14(B) shows a setup to compensate for additional polarization problems that may be caused by the circulator (CIR) 134. Even in the case of polarization independent circulators, a wavelength dependent delay between the two orthogonally polarized light fields through the circulator is possible. The design shows a technique to realize a sigma ring setup without a circulator 134, optimized to prevent polarization chromaticity effects in the FDML laser.

The design illustrated in FIG. 14(C) shows a concept where the light field propagates through the delay (D) 137 in opposite directions. In such a Sagnac configuration, both counter-propagating waves experience the same polarization chromaticity. Optional polarization controllers 135 help to prepare a suitable polarization state.

In all the described designs the sequence and positions of the individual components can be altered as long as FDML operation is still possible. The gain element 5' can be placed in the linear part (D) 137, to achieve double pass gain. The output coupler 136 can be placed at most parts of the cavity. The Faraday mirror 138 can also act as an output coupler. Multiple PCs 135 can be placed at virtually every point in the cavity. Depending on the gain of the gain medium 5' and the back reflecting intensity of the filter, one or no isolators 133 is needed. The ring can include a polarization maintaining fiber.

ii) Methods and Designs to Reduce Polarization Chromaticity and Rotation in the Fiber Spool:

The second class of methods and designs to minimize the polarization chromaticity is to reduce polarizing effects in the delay part in the case of a fiber spool as delay (DL). The designs discussed in the following are either methods to reduce the polarization chromaticity in the fiber spool or to compensate and cancel it.

Because reduced birefringence will positively affect polarization chromaticity, one method to minimize polarization chromaticity is to maximize the loop diameter in the fiber spool. A design should be chosen where the diameter of the fiber spool approaches the chassis size of the laser. Typically the minimum bending radius would be 20% or more of the minimum chassis dimension. A loosely wrapped air spool will further help to reduce polarization chromaticity caused by stress. Fiber coating other than standard acrylic coating helps to reduce polarization chromaticity to prevent excessive friction and long term adhesion of the fibers to each other. Another method to minimize polarization chromaticity is to use fibers with a smaller diameter. In an example embodiment, a 80 um cladding fiber, a single mode fiber with standard core (depending on the wavelength) may be used, however with reduced cladding diameter. For FDML operation near center wavelengths of 1300 nm or 1500 nm, standard optical fibers such as Corning SMF28 or equivalent fiber may be replaced by with a fiber including a 9 um core and 80 um cladding. The fiber spool can also be split into several parts, where the rotation/spindle axes may be orientated in a non-parallel manner. The multiple parts can have different numbers of convolutions/turns and different radii. If multiple spools are oriented parallel, polarization controllers in between can be used to change the polarization state. A series of smaller adjustable spools (paddles) with smaller numbers of turns can be used to introduce high order delay between the orthogonal polarization states. It should be pointed out that this technique does not refer to polarization controller paddles embodying half or quarter waveplates, but to sequences with higher order delay. The number of turns would be such that a high order delay, more than one wavelength is generated between the different orthogonal polarization states. In an example embodiment, a series with a binary number of turns (1, 2, 4, 8, 16 . . . ) on these loops/paddles may be employed.

The fiber can be wound in a non-circular symmetry where the local bending radius vector substantially changes over one loop or that the loop does not lie in one plane (three-dimensional winding). In example embodiments, toroidal winding or figure-8 winding with 90° tilted spindle axes may be used.

iii) Methods and Designs to Prepare a Polarization State that is Robust to Polarization Chromaticity Before the Light Enters the Delay, or Compensate the State after it Exits the Delay.

Optical elements can be used to prepare a wavelength independent polarization state of the light before it enters the cavity delay. Example states include linear, parallel to the slow axis of the spool, linear, parallel to the fast axis of the spool, or circular. To reduce chromaticity of the polarization controller, a bulk optic polarizer can be employed.

A depolarizer in form of a depolarizing plate or an active depolarizer (polarization modulator) can be used to prepare a virtually non-polarized state of the light before it enters or after it exits the delay. One or more lengths of multi-mode fiber can be used to depolarize the light. A non-linear or non-planar configuration of this length of multimode fiber can be used.

Figure 15:
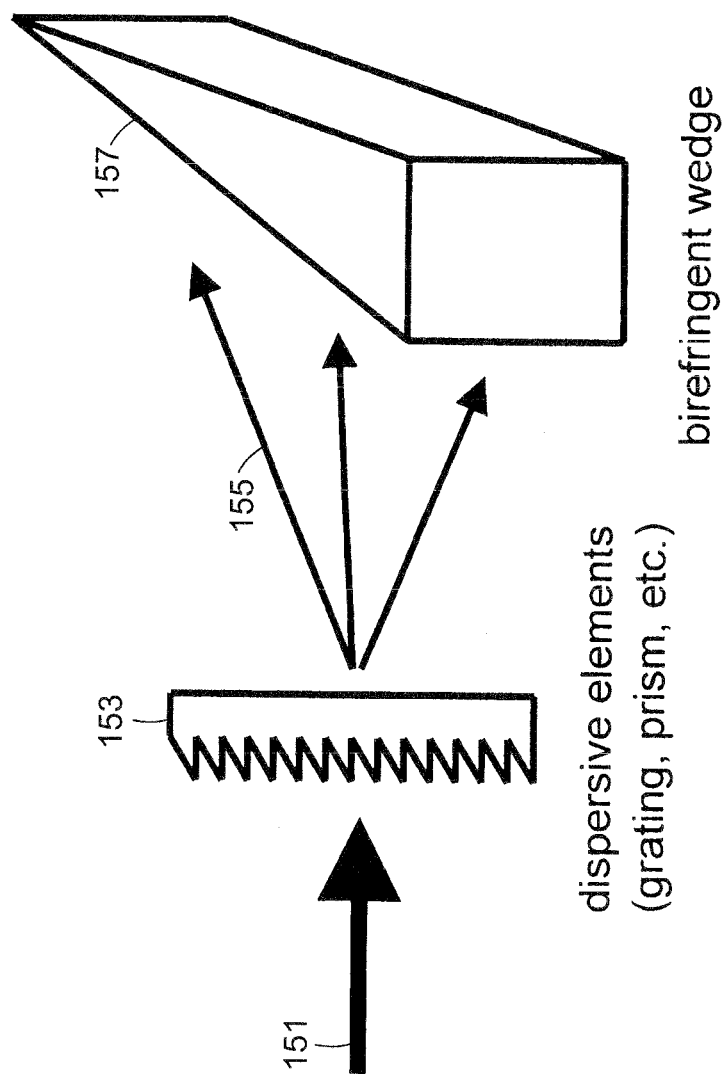
FIG. 15 is an illustration of an optical element that may be used for direct compensation of polarization chromaticity according to example embodiments.

FIG. 15 shows a schematic of an element which can directly compensate the polarization chromaticity. It provides different polarization rotation for different wavelengths. The light 151 is coupled in a dispersive element 153 like a prism, a grating etc., and the spatially dispersed light 155 propagates through a wedge of birefringent material 157, or any element that has spatially dependent phase retardation. The different wavelength components experience different differential phase retardation of their orthogonal polarization states. A lens to collimate the beam after the grating and a lens and grating to recombine are not drawn. A dual pass configuration enables one set of grating and lens.

Figure 16A:
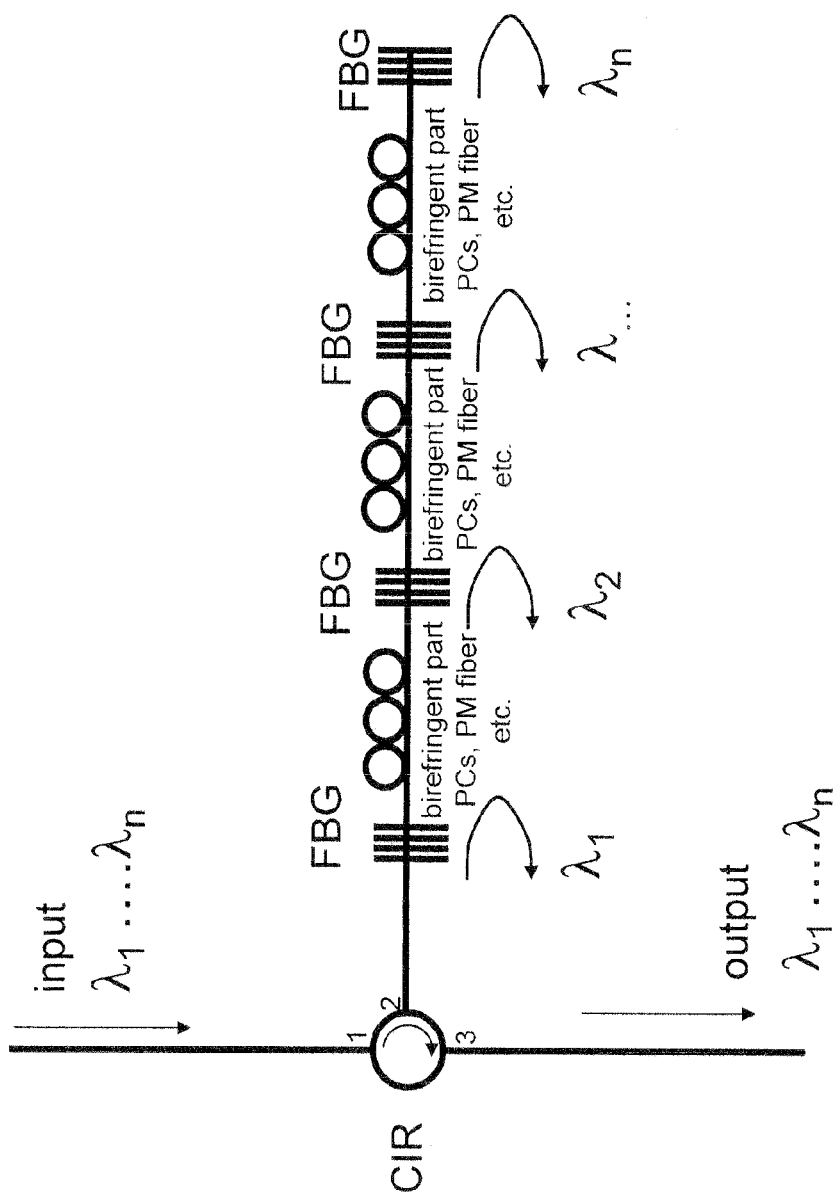
FIGS. 16A-16B are schematic diagrams of optical based dual pass control systems used for polarization chromaticity management according to example embodiments.

FIG. 16A depicts a fiber optic equivalent. The light (input) is coupled into a section with substantial birefringence. In this case the coupling is achieved through a circulator (CIR) but other designs are equivalent. The birefringent part could be a series of fiber loops, a length of PM fiber or comparable fiber or any component with different group velocities for the two orthogonal polarization states. A series of reflectors (here fiber Bragg gratings (FBG), but other wavelength selective reflectors are possible) reflect back different parts of the spectrum at different positions, corresponding to different delays. In this manner the different wavelength components experience different birefringence and the desired effect of polarization chromaticity can be achieved or cancelled. It should be appreciated that such a series of reflectors can simultaneously be used to compensate dispersion, because it provides different optical cavity lengths for different wavelengths. The described examples are special cases of the general polarization chromaticity compensation method which include the steps of spatially or temporally separating the different wavelength components and introducing various amounts of birefringence in the separated part.

Figure 16B:
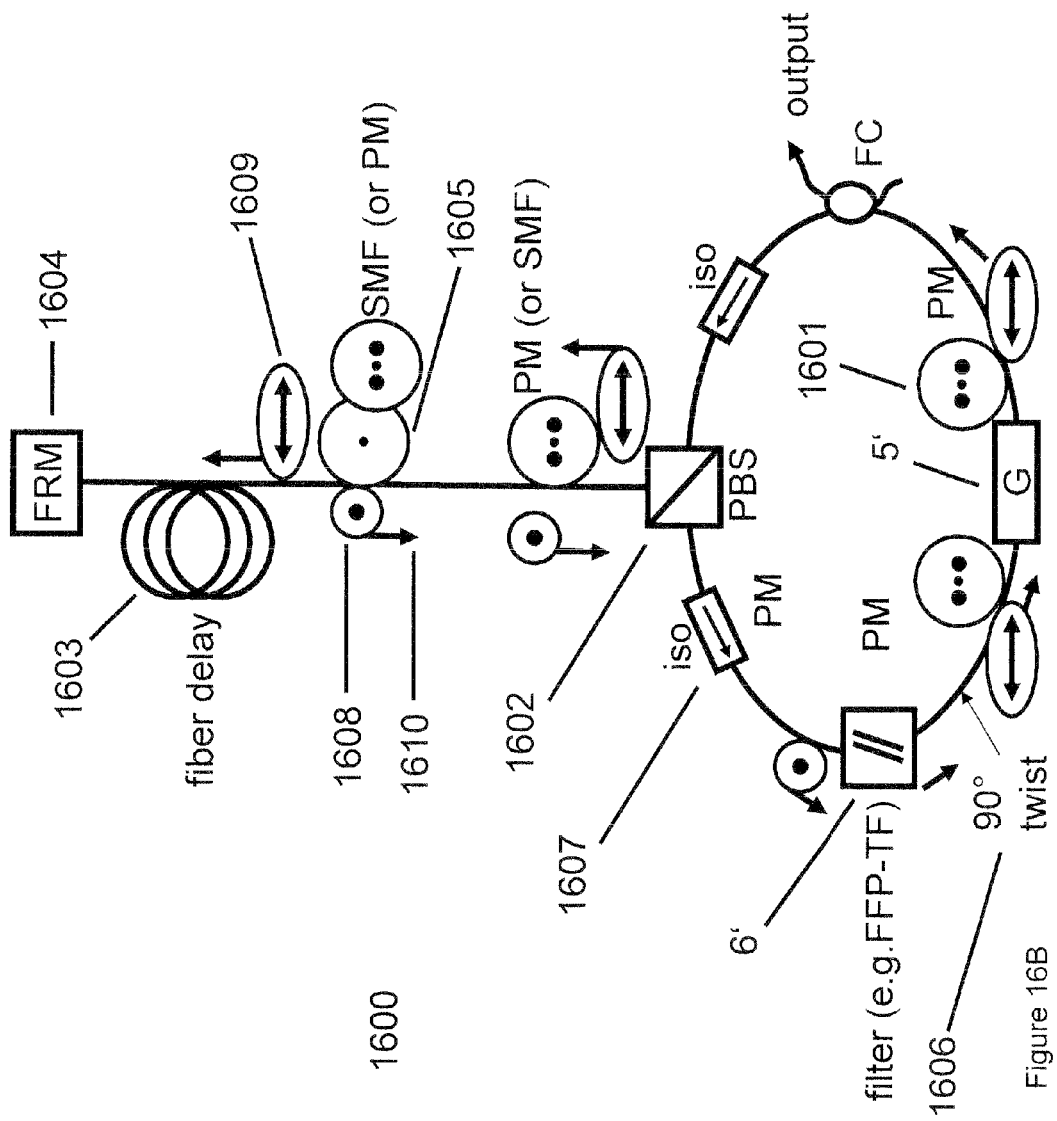

FIG. 16B illustrates another FDML laser configuration 1600 that is robust to polarization chromaticity. In this configuration, polarization maintaining fiber (PM) 1601 is used in the circular portion of the cavity to maintain a controlled polarization state. A polarization beamsplitter (PBS) 1602 is used to direct light into the linear portion of the cavity. The fiber delay 1603 can be conventional optical fiber that does not maintain a fixed polarization state, since the Faraday rotator mirror (FRM) 1604 will rotate the polarization of the incident light by 90 degrees prior to passing through the fiber delay 1603 a second time. This allows the cost of the fiber to be kept low, since conventional fiber (SMF) 1605 is much less expensive than polarization maintaining fiber. Since the light returning to the circular portion of the cavity is rotated by 90 degrees compared to the light that entered the linear portion of the cavity, a 90 degree twist in the fiber 1606 may be employed prior to the laser gain medium (G) 5' in order to align the polarization state of the light to the gain medium's preferred polarization axis. This 90 degree twist 1606 could also be located prior to the tunable filter 6', prior to the isolator 1607 following the PBS 1602, or inside the PBS itself. The orientation of the polarization state of light in the cavity is represented as being either perpendicular to the plane of the page 1608 or parallel to the plane of the page 1609. The direction of light propagation in the cavity is represented by arrows 1610.

Figure 17:
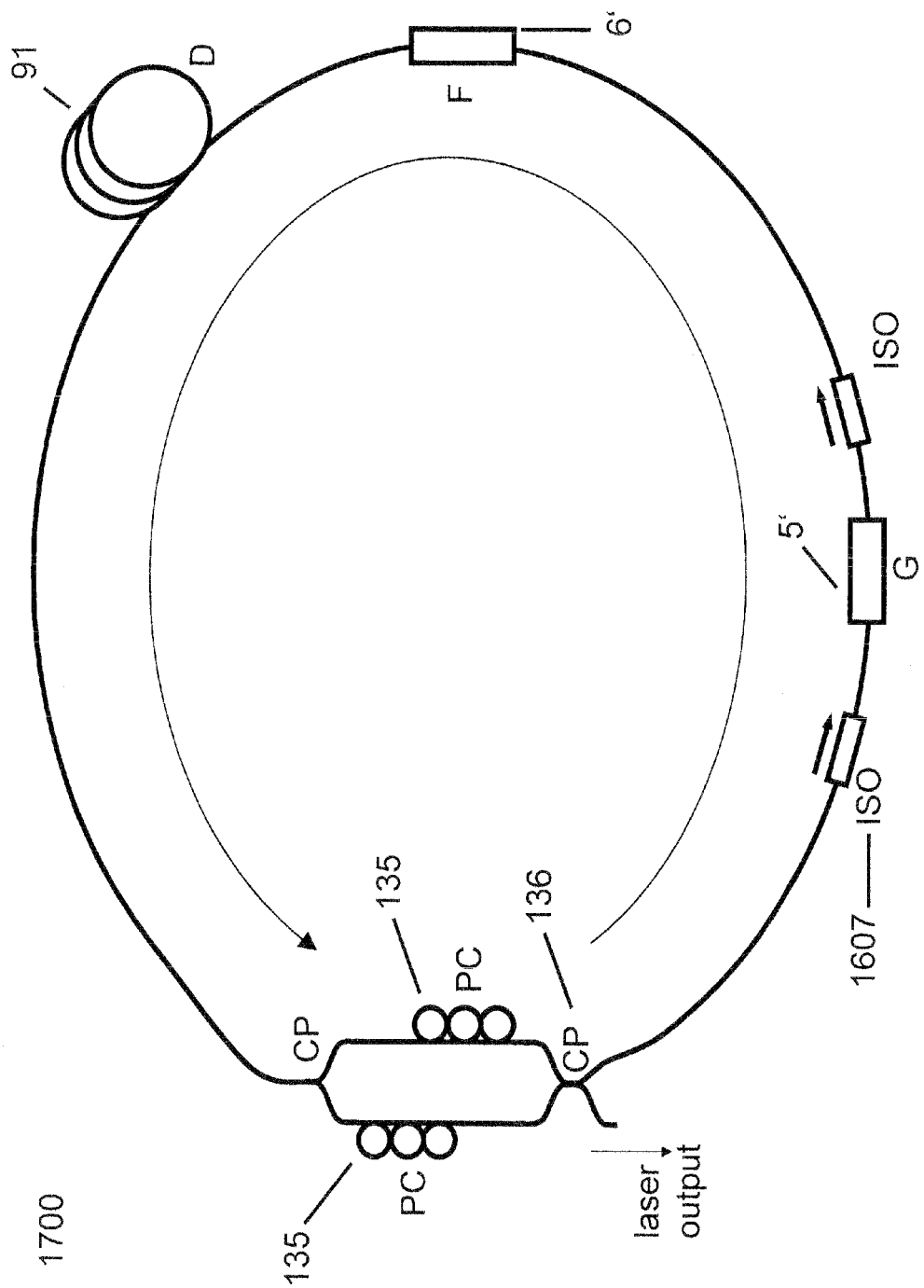
FIG. 17 is a schematic diagram of an intra-cavity Mach-Zehnder interferometer (MZI) used for polarization chromaticity management according to example embodiments.

FIG. 17 shows an FDML laser 1700 with intra cavity Mach-Zehnder interferometer (MZI). Because the polarization chromaticity usually shows regular spectral modulations, it is possible to split the light and introduce a Mach Zehnder interferometer with two separate polarization controllers (PC) 135. The polarization controllers can be set independently and the severity of the spectral modulations can be reduced. One port of the Mach-Zehnder interferometer output can be used as the laser output coupler (CP) 136, and the other port can be used to return light to the cavity. To avoid spectral modulations, an example embodiment includes matching the arm lengths of the Mach Zehnder better than a wavelength, or introducing a mismatch larger than the instantaneous coherence length. The gain element (G) 5', isolators (ISO) 1607, tunable filter element (F) 6', and fiber delay (D) 91 are arranged in a similar manner to other embodiments of FDML lasers.

Additional Intra-Cavity or Extra-Cavity Active or Passive Elements to Improve Performance Depending on the application, additional optical elements inside or outside the cavity can improve the performance of the FDML laser.

a) Mach Zehnder Interferometers

A special class of elements are Mach Zehnder Interferometers (MZI). It is understood that other forms of couplers may be used besides 1×2 couplers to construct an MZI and, in fact, all described methods below can be extended to 1×n couplers. The MZIs can be used inside the FDML cavity as sketched in FIG. 17. It should be noted at this point that the described features, designs and methods can also be achieved by any other type of interferometer which splits the light field into a finite number of optical paths and recombines them again. Typically, the main concept is to insert two different optical elements in the two branches/arms of the MZI or to adjust the lengths in a defined way to achieve the desired performance improvements. Insertion of identical elements can be used, for example, to increase power performance.

Figure 18:
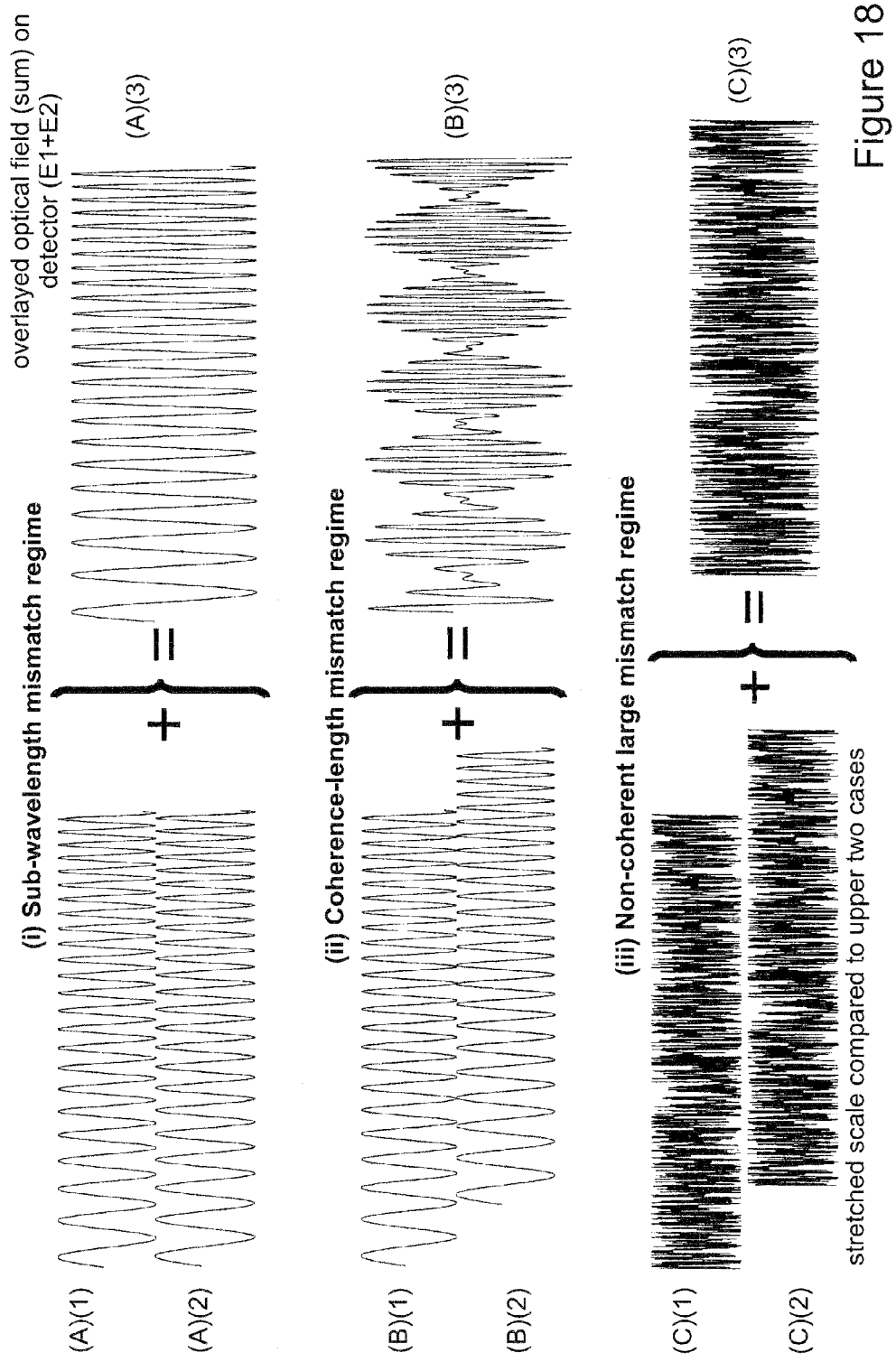
FIG. 18 is an illustrative example of three operational regimes of the MZI of FIG. 17 employing three respective design criteria of the MZI according to example embodiments.

Because of the spectral transmission characteristics and the spectral modulation of such MZIs, a special design is employed if it is intended to use them in an FDML laser. The difference compared to other lasers is that the characteristic spectral modulations of such MZIs, which are inherently linked to the generation of a delayed waveform, can hamper effective synchronization of the filter drive period with the roundtrip time in FDML lasers. Therefore, it may be beneficial to apply special designs. There are generally three methods and designs for such a MZI inside an FDML laser (see sketches in FIG. 18):

(i) Sub-Wavelength Mismatch Regime:

The two arm lengths of the MZI (represented by optical fields (A)(1) and (A)(2)) are matched to a length on the order of or smaller than one wavelength. In this regime the MZI has no prominent spectral transmission characteristic over the sweep range. The two optical fields are combined coherently, resulting in optical field (A)(3). In this operation regime it is very important to stabilize the arm lengths to values better than a wavelength if no intentional averaging is desired. Usually no excessive fiber lengths can be used, unless intentional averaging of the optical fields is desired. This regime can be ideal for multiplexing of gain elements. In this case, each arm would have a separate gain element. The arms could have different gain wavelengths to widen the sweep range.

(ii) Coherence-Length Mismatch Regime:

The two arm lengths of the MZI have an intentional mismatch greater than one wavelength, but smaller than the instantaneous coherence length, as illustrated by optical field (B)(1) and (B)(2). In this regime the MZI has a prominent spectral transmission characteristic over the sweep range. The two optical fields are combined coherently but strong modulations are observed, as shown by optical field (B)(3). In optical coherence tomography (OCT) applications this generates echoes within the imaging range. Because of the coherent summation in this operation regime it is important to stabilize the arm length to values better than a wavelength if no intentional averaging is desired. Usually no excessive fiber lengths can be used in both arms, unless intentional averaging of the optical fields is desired.

(iii) Non-Coherent Large Mismatch Regime:

The two arm lengths of the MZI have an intentional mismatch greater than the instantaneous coherence length of the laser, as illustrated by optical fields (C)(1) and (C)(2). In this regime the MZI has no spectral transmission characteristic over the sweep range because the two waveforms are added incoherently, resulting in an optical field (C)(3), and the two arms act like independent sources coupled into the second coupler of the MZI.

There are various applications for MZIs inside the cavity of an FDML laser and depending on the application, different mismatch regimes are used. Example embodiments (a)-(f) are described below:

(a) As described in the previous section the two arms can have two independent polarization controller units (PC) to reduce the fringe contrast and output spectrum modulations caused by the polarization chromaticity (FIG. 17). Usually this would be performed in the sub-wavelength mismatch regime (i) or the non-coherent large mismatch regime (iii) in order to avoid spectral modulations. However, it is also possible that in the coherence-length mismatch regime (ii) the mismatch is set to a value which exactly counteracts the fringes and modulation.

(b) The asymmetry in the two branches can be set to a value such that the dispersion of the system is compensated. The total roundtrip time through the cavity is different for both arms. For example, it is possible to match the roundtrip time for the longer wavelength range one to the shorter wavelength range. This can be achieved with wavelength dependent splitters or regular couplers. Usually this would be performed in the non-coherent large mismatch regime (iii) in order to avoid spectral modulations and because larger offsets are needed.

(c) In OCT applications, intentional echoes can be generated with a delay set by the arm length mismatch. Usually this would be done in the non-coherent large mismatch regime (iii). It replicates the measurement range on swept source OCT applications (ss-OCT) and increase the coherence length. This can help to minimize the effort to find the initial match in the arm length of the Michelson interferometer of an OCT setup, because usually OCT has a limited ranging depth of only several millimeters.

(d) A polarization dependent MZI can be used to cancel polarization dependent gain of the gain medium. Such a MZI would have a polarization beam splitter instead of unpolarized beamsplitters or couplers. Additional polarization controllers or polarization maintaining fiber are used to ensure the appropriate polarization state for the two polarization dependent gain chips in both arms. All three mismatch regimes can be used.

(e) Gain elements in both arms can be used to increase the power or broaden the sweep range. Usually this is performed in the sub-wavelength mismatch regime (i) or the non-coherent large mismatch regime (iii) in order to avoid spectral modulations.

Figure 19A:
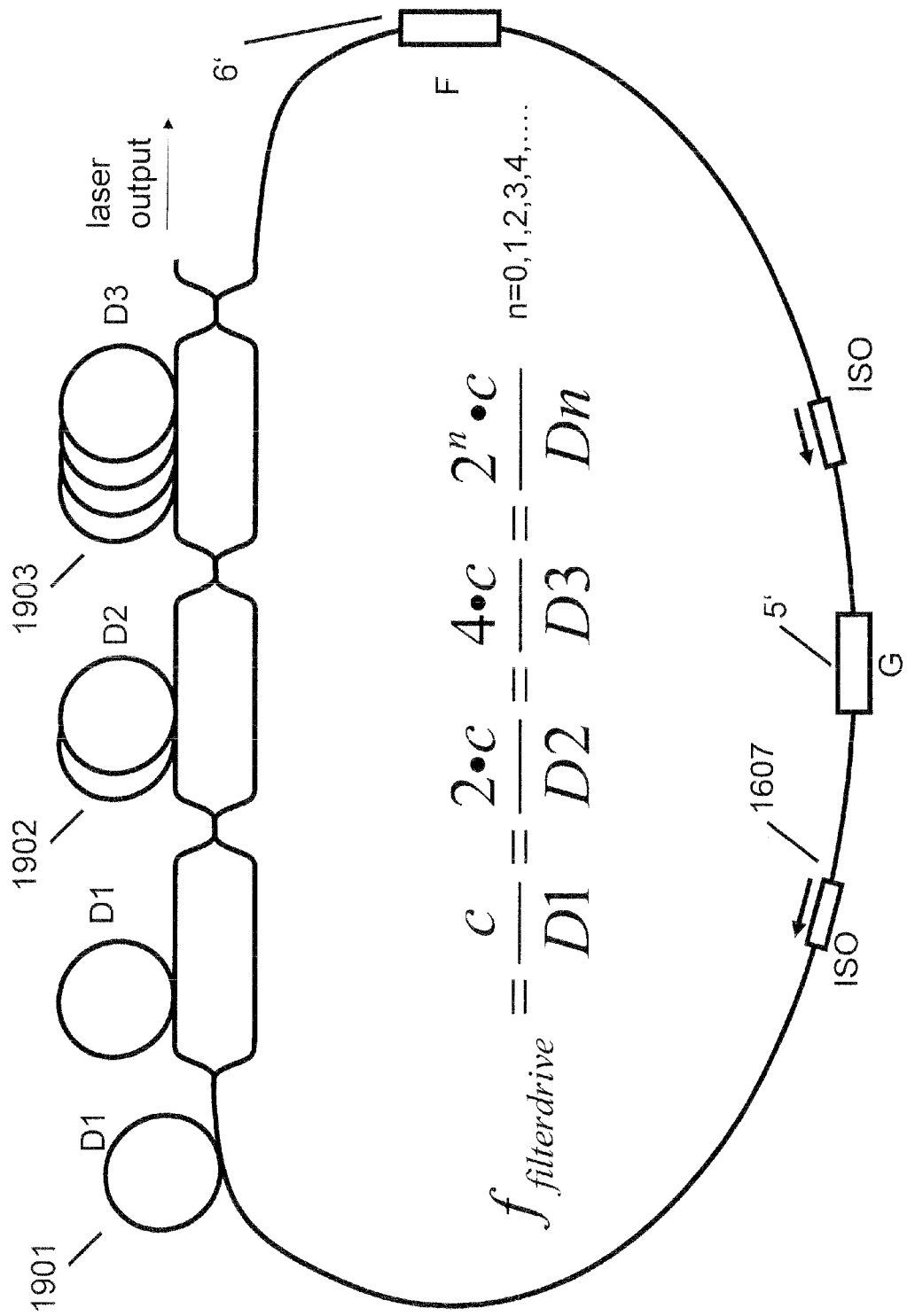
FIGS. 19A-19B are schematic diagram of intra-cavity and extra-cavity MZI sequences used to multiply the laser sweep rate according to example embodiments.

(f) One of the arms/branches can have a fiber delay which is matched to the filter sweep time. The extremely large mismatch corresponds to the non-coherent large mismatch regime (iii) shown in FIG. 18. This design has the effect of optically averaging the waveforms and increases the stability of the laser. A series of MZIs in series with binary length can be applied to increase the averaging effect. Such a MZI sequence can also be used inside the cavity to multiply the sweep rate. FIG. 19A shows an FDML laser with a series of MZIs in series with fiber delays 1901, 1902, and 1903 increasing as a power of 2. The fiber delays act as arm length mismatches in each MZI. The advantage of multiple MZI in series is that there is no power loss in the case of an intra cavity MZI (if the second coupler is used as output) and there is only a 3 dB power loss in the case of the external sequence, independent to what factor the sweep rate is multiplied. The gain element (G) 5', isolators (ISO) 1607, tunable filter element (F) 6', and fiber delay (D) 91 are arranged in a similar manner to other embodiments of FDML lasers.

Figure 19B:
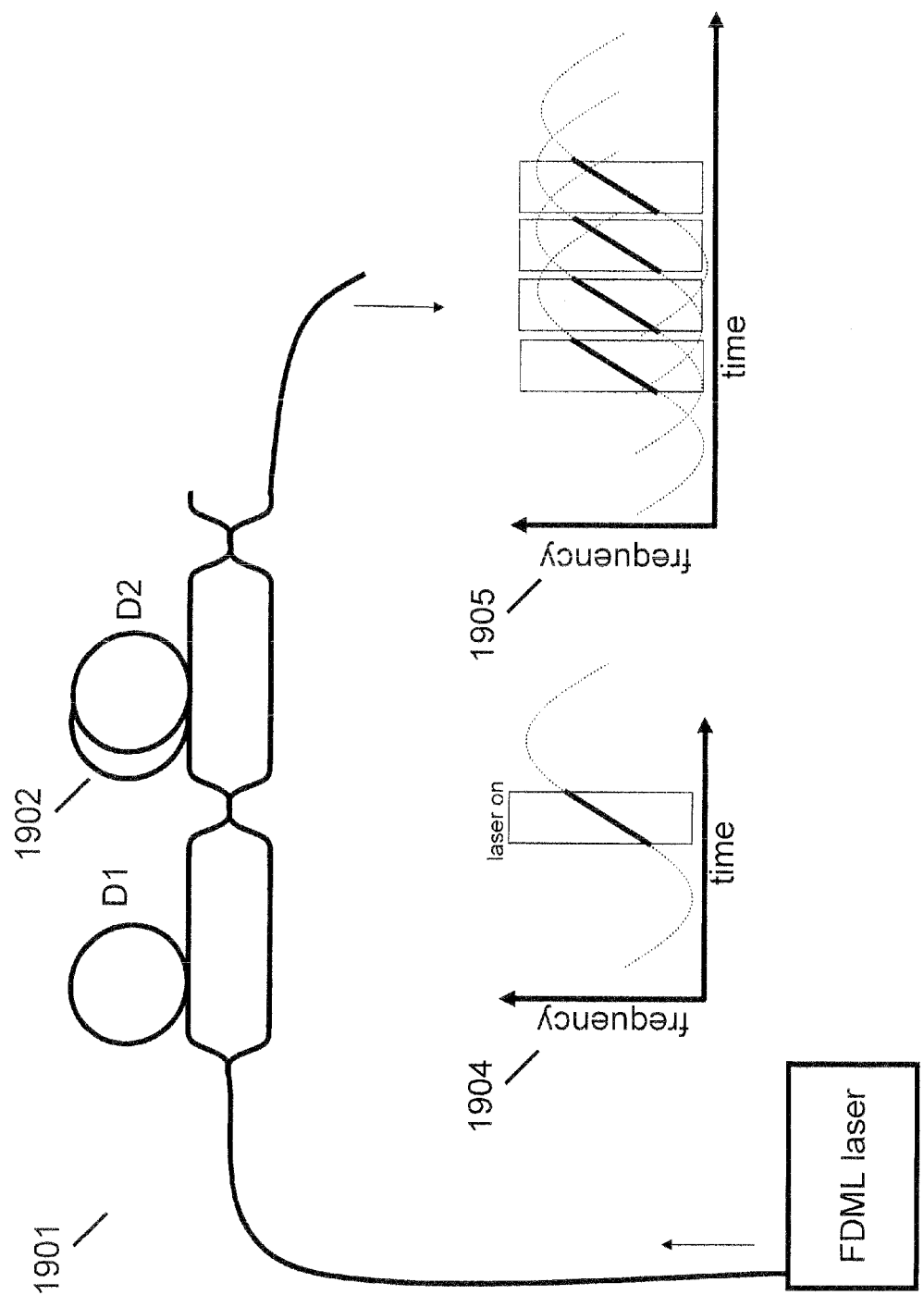

A series of MZIs can also be used outside of the FDML laser cavity to multiply the sweep rate. FIG. 19B shows an FDML laser with a series of external MZIs with fiber delays 1901 and 1902 increasing as a power of 2. At each MZI stage the FDML optical frequency sweep is copied, one copy is time-delayed by a time corresponding to the fiber delay, and then recombined. To prevent the copied frequency sweeps from overlapping in time, the laser is enabled during a correspondingly shorter period of time. This can be achieved by modulating the gain medium inside the FDML laser. In this way the sweep rate is multiplied in a similar manner to that which occurs using a series of intra-cavity MZIs. This principle is shown in the first frequency versus time plot 1904 and the second frequency versus time plot 1905. The first plot 1904 shows the portion of the tunable filter element drive period (dotted lines) where the laser gain medium is enabled (solid line). The second plot 1905 shows the output after the second MZI with delay D2 1902, where 4 non-overlapping copies of the sweep have been produced. Such a high order sweep frequency multiplication can be the prerequisite for a linear sweep in frequency, because it is possible to use only a very small part of the sinusoidal drive waveform where the sinusoid is increasingly linear. In an example embodiment, the arm length mismatch of each interferometer in the series of interferometers may be substantially equal a fraction of a power of 2 (e.g., ½, ¼, ⅛) of the total cavity length inside the FDML laser.

b) Fiber Bragg Gratings (FBGs) in FDML Lasers

A series of fiber Bragg gratings can be used to compensate the cavity dispersion and match the roundtrip time for the different wavelength components. A setup similar to the one in FIG. 16A may be used, however not necessarily with additional lengths of fibers or polarizing elements in between each FBG. In a setup as shown in FIG. 16A and in the case of FDML operation in the normal dispersion regime (e.g. in the 1050 nm wavelength range), the FBGs closer to the circulator/cavity would reflect shorter wavelength components. The FBGs further away from the ring/circulator would reflect longer wavelength components. It should be pointed out that either one chirped FBG (a chirped FBG has a continuously changing period) can be used which covers the whole wavelength range of the FDML laser, or several chirped or non-chirped FBGs can be used in a sequence. It is important to note that in FDML lasers, unlike short pulse lasers, the FBGs do not necessarily have to be phase matched.

c) Optical Switch

An optical switch can be used in order to select certain wavelengths and reroute them into different paths through the cavity. This can be used to apply dispersion compensation schemes with different path lengths or to pick certain wavelengths and couple them out of the cavity. An additional external Fabry Perot or other resonator can then be used to provided continuous wave (cw) output, again with the condition l<c/b, with the optical cavity length l, the speed of light c and the optical frequency bandwidth of the additional filter b.

d) Phase Modulator

FDML lasers can have slightly discontinuous tuning characteristic or mode-hops in their operation. In discontinuous or mode-hopping operation, the output light stays at one frequency for a finite time and then rapidly changes. This is in contrast to continuous tuning, where the frequency of the output light changes in a smooth and continuous manner. In terms of the spectral output of the FDML laser, discontinuous operation results in a very narrow spectral line which jumps rapidly from time to time. This can be a problem for wavelength resolved measurement applications since certain wavelength values will be missing from the output spectrum, or will occur at unpredictable time points. A phase modulator inside or outside the cavity can be used to broaden the spectral line. The phase modulator should be driven with electronic frequencies on the order of the instantaneous optical bandwidth of the laser to achieve the desired effect. It should be appreciated that line broadening can also be achieved with an amplitude modulator.

Intracavity Filters and Stepwise Tuning

In many applications, it is beneficial to operate an FDML laser in a swept mode where the generated swept waveform includes a series of discrete optical frequencies or wavelengths that are stepped in a successive fashion. Discrete, stepwise tuning can be beneficial for many applications such as optical coherence tomography, spectroscopy, and metrology. Swept tuning with discrete steps may provide narrower instantaneous laser linewidths, improved coherence properties and improved noise. These properties can improve imaging performance in swept source optical coherence tomography and interferometry applications. The generation of a series of discrete frequency or wavelength steps also has advantages for measuring the laser output and providing improved control of laser parameters.

Figure 20:
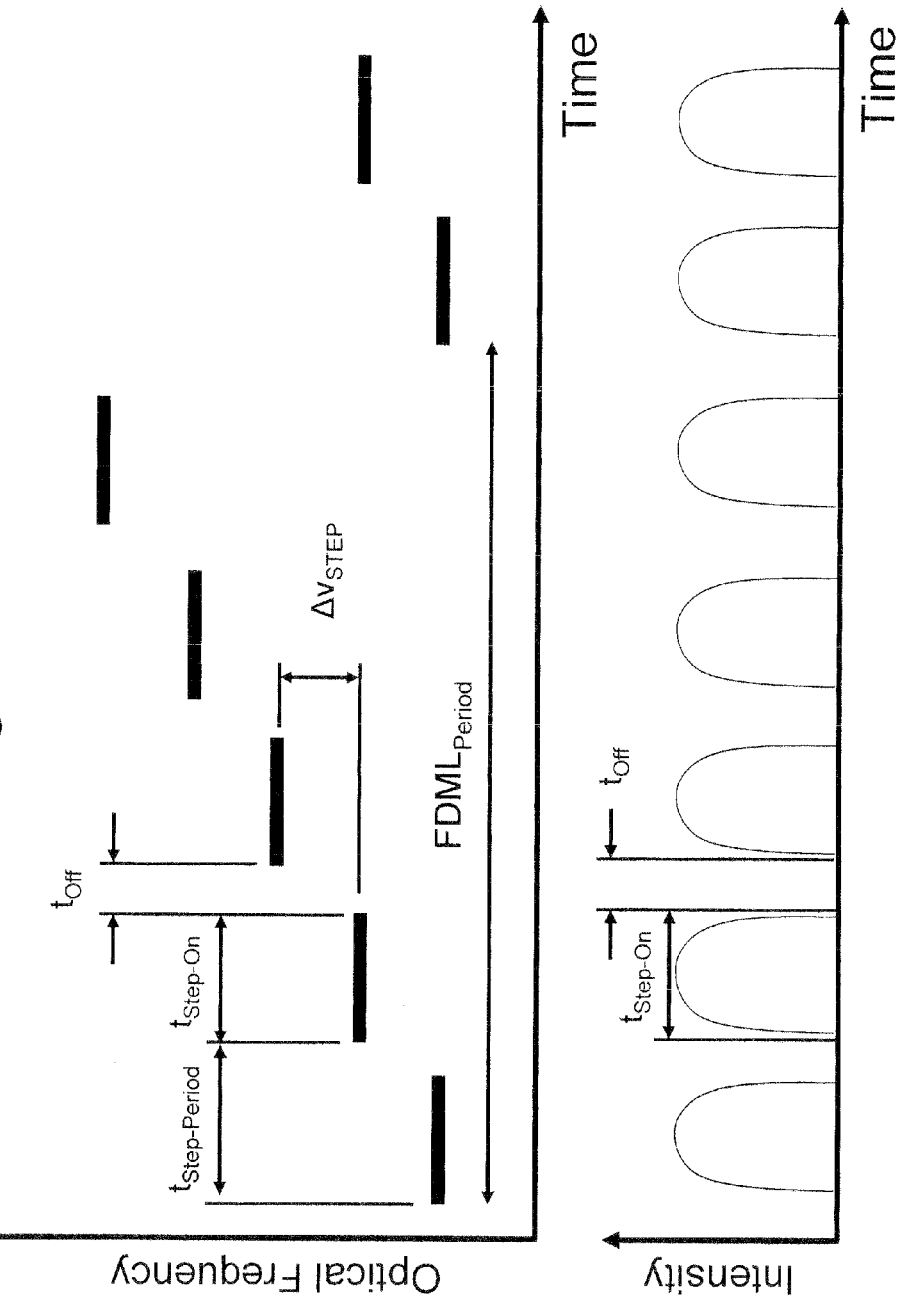
FIG. 20 is a graph depicting stepwise tuning of an FDML laser according to example embodiments.

FIG. 20 illustrates an example of swept stepwise FDML operation. The FDML laser emits light of a certain optical frequency or wavelength for a time duration of $t_{STEP-ON}$ and then switches the output frequency or wavelength to the next value. This process of generating steps in frequency or wavelength is repeated across the entire desired tuning range of the swept laser output. In some cases, the system may be configured so that there is a time between the steps when there is no laser output, $t_{OFF}$. However, depending on the system parameters, the FDML laser may generate an output with nearly continuous intensity or an output with a modulation in intensity between steps. For some applications it is desired that the difference between each step has a constant value in optical frequency $\Delta v_{STEP}$ and that the steps occur at a constant rate, with a constant time spacing $t_{STEP-PERIOD}$. After a series of steps, the entire swept stepwise output will be repeated with a repetition rate obeying the FDML condition such that the periodic time $FDML_{PERIOD}$ fulfills the FDML condition, where $FDML_{PERIOD}$ is equal to the cavity optical roundtrip time or harmonics thereof.

Figure 21:
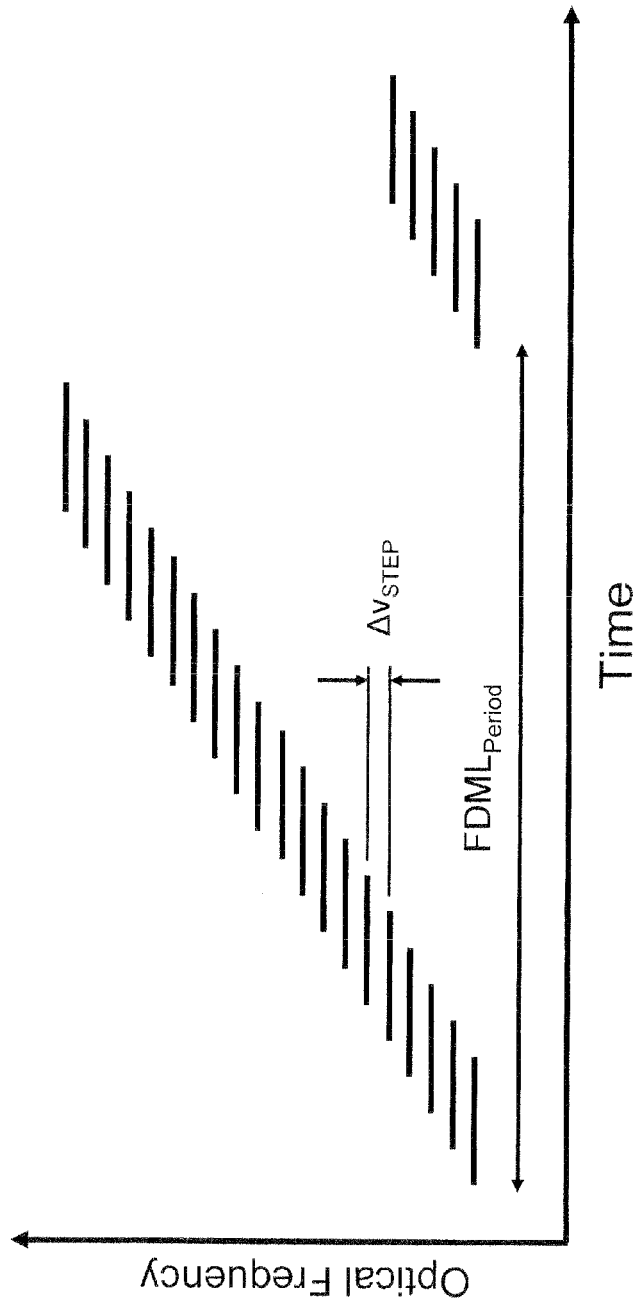
FIG. 21 is a graph depicting stepwise tuning of an FDML laser according to other example embodiments.

Another example of swept stepwise FDML operation is shown in FIG. 21. The FDML laser emits light which includes a step pattern with a distribution or comb of optical frequencies or wavelengths, with multiple discrete frequencies or wavelengths being generated at a time. The center or average frequency of this distribution or comb changes in time as the laser is swept, however, the individual frequencies in the comb remain fixed. After sweeping across the desired range of frequencies, the entire swept stepwise output will be repeated at the repetition rate of the FDML laser. The examples in the figures describe unidirectional sweeps, however it is understood that the same concept applies to bidirectional sweeping.

Figure 22:
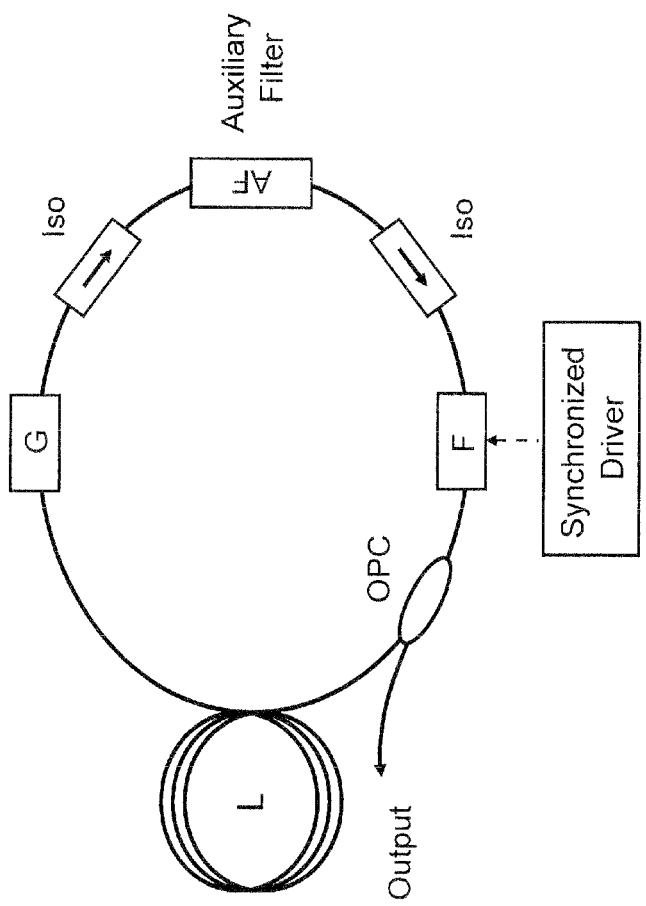
FIG. 22 is a schematic diagram showing an illustrative example of an FDML laser configured to produce a stepwise tunable output according to example embodiments.

FIG. 22 shows an example of a configuration for obtaining swept stepwise tuning from an FDML laser. Stepwise FDML tuning may involve the use of two filters in the laser: the adjustably tunable filter used for FDML operation, herein referred to as the "tunable FDML filter," and the additional auxiliary filter with multiple narrowband frequency or wavelength maxima, herein referred to as the "auxiliary filter." In the schematic shown in FIG. 22, the laser gain medium G, the isolators Iso, the auxiliary filter AF, the tunable FDML filter F, the output coupler OPC, and the fiber delay L form the FDML laser cavity. It should be appreciated that the auxiliary filter may be either fixed or adjustable on a time scale larger than one sweep period to alter the characteristics of the laser output. The FDML laser output could also be filtered by an auxiliary filter outside of the cavity, however placing the auxiliary filter inside the cavity may be desirable if higher output power and narrower linewidth are required. Although this example is shown for a simple ring cavity embodiment of the FDML laser, is recognized that equivalent methods can be applied to other embodiments of the FDML laser, including, but not limited to those involving linear cavities, sigma rings, and any cavity design enabling FDML operation.

The additional auxiliary filter should have multiple, narrow bandwidth, transmission maxima within the gain bandwidth of the laser gain medium. The bandwidth of the auxiliary filter should be less than the bandwidth of the tunable FDML filter. Examples of auxiliary filters include, but are not limited to, an etalon filter or Fabry Perot type filter, a series of Fiber Bragg gratings in combination with elements such as circulators, or a series of narrowband dielectric or waveguide filters, configured to provide multiple, narrowband, filtering at the desired output frequencies or wavelengths. In some applications the transmission characteristics of the additional auxiliary filter will be fixed such that it transmits or reflects a predetermined set of wavelengths or frequencies with desired bandwidths. However in other applications, the auxiliary filter characteristics may be adjusted and stabilized using control systems. For example, a configuration with an adjustable auxiliary filter which is locked or stabilized with respect to an external frequency of wavelength reference can be used when it is desired that the FDML laser generate a swept stepwise output where the frequencies or wavelengths are precisely determined. An alternate method is to measure the output of the FDML laser at a particular time, when it is generating a particular frequency step, and to adjust the auxiliary filter such that the laser output frequency is locked or stabilized with respect to an external reference. Since the transmission characteristics and maximum transmission frequencies of many types of filters exhibit wavelength dependence, the auxiliary or tunable FDML filters may be stabilized by controlling their temperatures using electronic circuitry.

To facilitate locking of the stepwise tuned FDML laser output to an external reference frequency, the auxiliary filter can be measured by introducing a separate narrow linewidth light source at a precisely known optical frequency into the cavity. This narrow linewidth source would be measured after transmission through the auxiliary filter by using a wavelength selective filter and photodetector located after the auxiliary filter. The auxiliary filter could then be adjusted such that the narrow-linewidth source is transmitted at a precisely known time, thereby locking the FDML output to the precisely known optical frequency of the narrow linewidth source.

Figure 23:
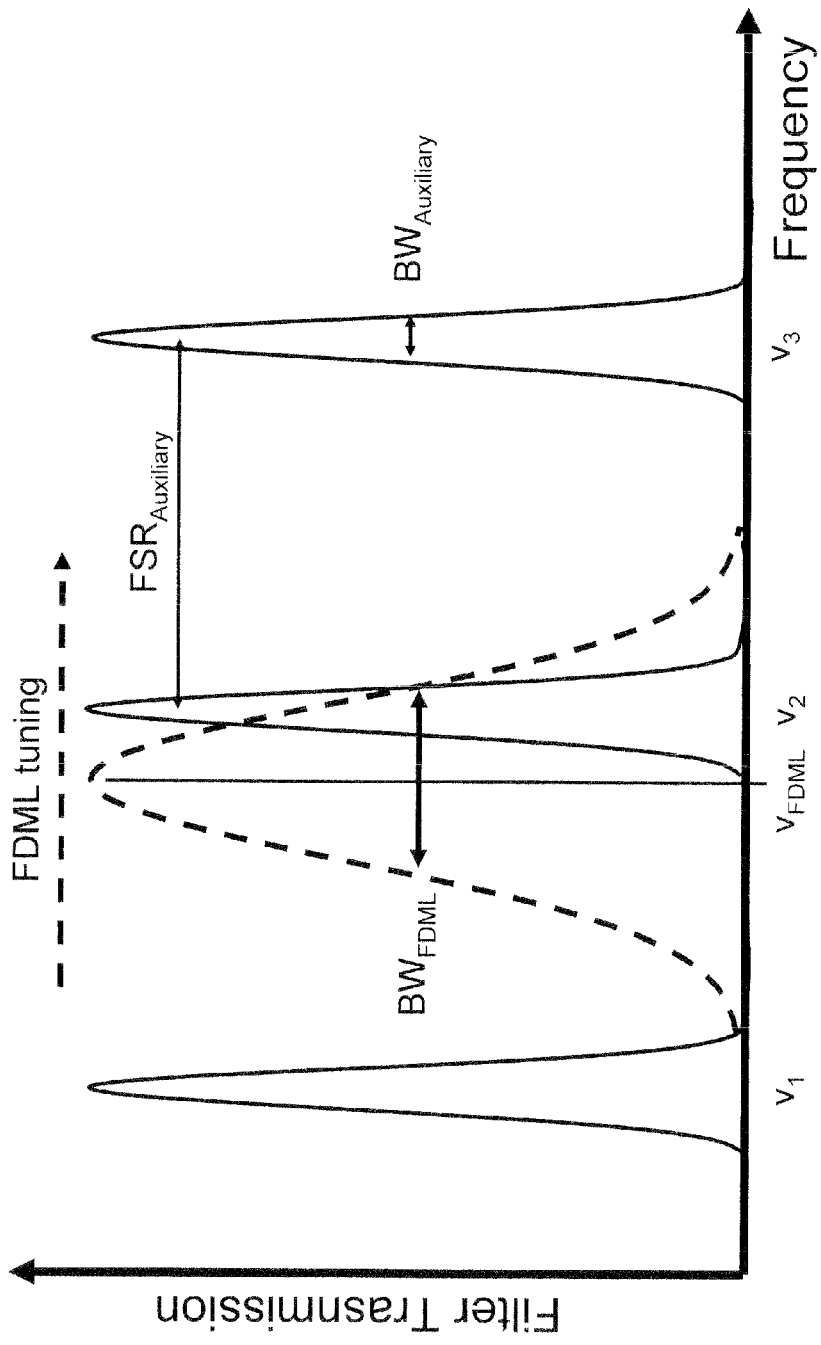
FIG. 23 is a graph depicting the filter characteristics of a stepwise tuned FDML laser according to example embodiments.
Figure 24:
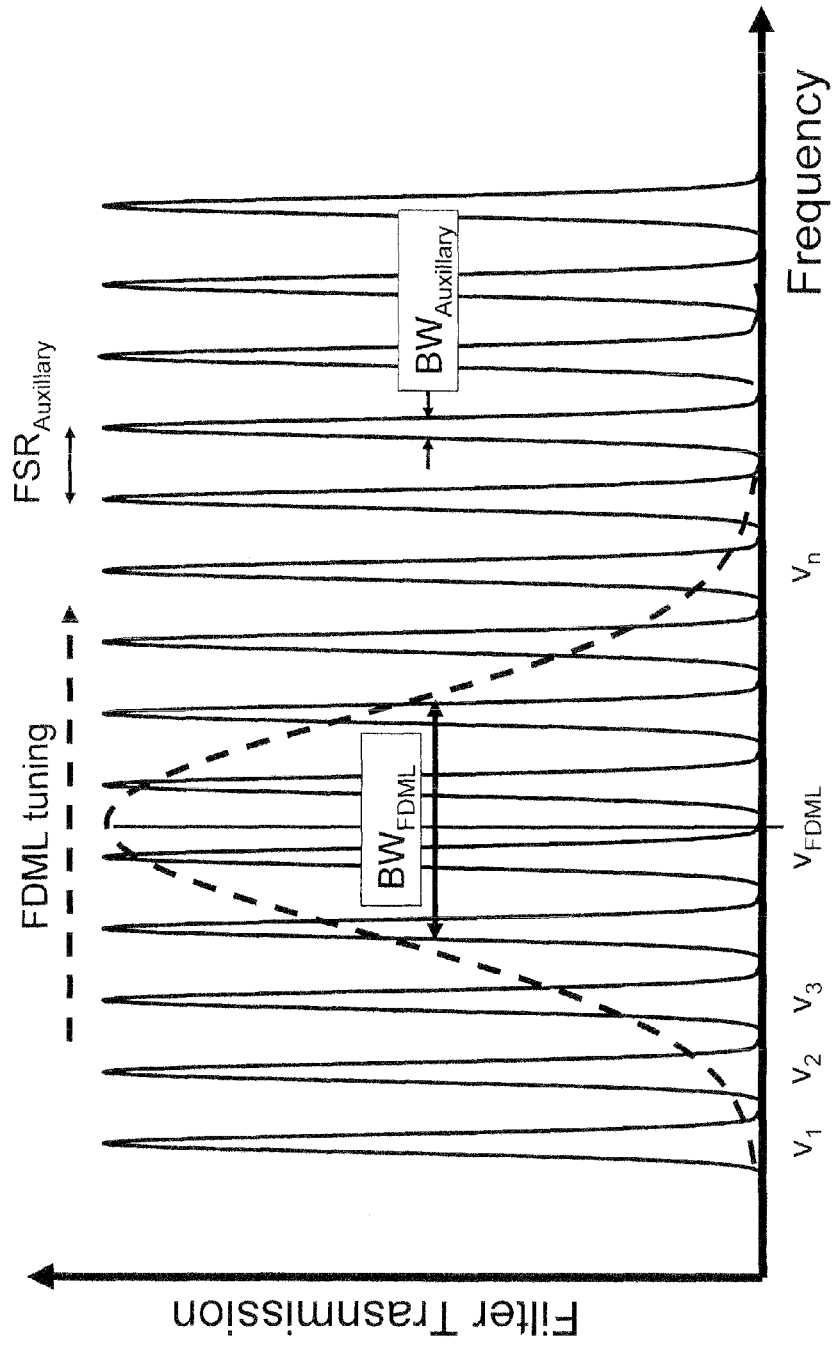
FIG. 24 is a graph depicting the filter characteristics of a stepwise tuned FDML laser according to other example embodiments.

Swept stepwise operation of FDML lasers may employ designing the characteristics of the tunable FDML filter and the auxiliary filter according to specific criteria depending upon the operation desired. FIGS. 23 and 24 show schematics describing the characteristics of the tunable FDML filter and the auxiliary filter for different regimes of operation. The auxiliary filter is characterized by a set of transmission maxima at transmission maximum frequencies $\nu_1$, $\nu_2$, $\nu_3$, etc., having transmission bandwidth $BW_{Auxiliary}$. In the case where the auxiliary filter is a Fabry Perot filter, the transmission frequencies are uniformly spaced and characterized by a free spectral range $FSR_{Auxiliary}$ which describes the frequency step $\Delta\nu$ between the transmission frequencies. The tunable FDML filter is characterized by a bandwidth $BW_{FDML}$ and a transmission maximum frequency $\nu_{FDML}$ which is adjustable as a function of time. The bandwidth of the auxiliary filter $BW_{Auxiliary}$ is narrower than the FDML filter $BW_{FDML}$ and therefore the auxiliary filter causes the FDML laser to produce narrower linewidth output than is possible with the FDML filter alone.

Without loss of generality, these criteria may be described using an example where the tunable FDML filter is a Fabry Perot filter and the auxiliary filter is a second Fabry Perot filter. However, it is recognized that other filters can be used and design criteria can be constructed for these embodiments. In the example, the tunable FDML filter is adjusted by sweeping its transmission maximum frequency $\nu_{FDML}$ across a range of frequencies. The tunable FDML filter is driven synchronously to the effective roundtrip time of light in the cavity or a harmonic thereof. For the case where the tunable FDML filter is a Fabry Perot filter, the transmission maximum frequency $\nu_{FDML}$ is tuned by varying the Fabry Perot mirror separation and therefore the transmission maximum frequency scans continuously across different frequency values.

It should be noted that if other types of filters are used as the auxiliary filter, the spacings of the transmission maxima may not be equidistant although in many cases an example embodiment is to generate evenly spaced transmission maxima. The use of a Fabry Perot filter as the auxiliary filter has the advantage that the Fabry Perot filter produces large numbers of transmission maxima which are equally spaced in frequency and can have very narrow bandwidths or linewidths. The main advantage of generating FDML-based frequency combs using an intra-cavity auxiliary Fabry Perot filter with multiple transmission peaks is that obtaining a wide range of optical frequency spacings is relatively straightforward. Very small to very large frequency spacings can be generated since Fabry-Perot filters with FSR's from several MHz to many THz are available. The filter can have a very narrow linewidth to frequency spacing ratio, or high finesse. Additionally, the positions of the auxiliary filter maxima do not have to be stationary and can be adjustable so that they are locked to an external frequency or wavelength reference. However it should be noted that the filter characteristics of the auxiliary filter are not typically tuned synchronously to the roundtrip time of light in the cavity.

There are different operating regimes for swept stepwise operation of an FDML laser that can be distinguished:

(i) $BW_{FDML} < FSR_{Auxiliary}$: This operating regime is shown in FIG. 23 and has an output as shown in FIG. 20. This configuration is used when it is desirable to obtain an FDML laser output including a series of isolated frequency steps. The laser will sweep stepwise across the transmission maximum frequencies of the auxiliary filter, generating a laser output at an optical frequency for a time $t_{STEP-ON}$ during which the tunable FDML filter maximum $\nu_{FDML}$ overlaps the transmission maxima of the auxiliary filter. This output is followed by a time $t_{OFF}$ when the laser output intensity decreases substantially and may approach zero intensity, occurring when the tunable FDML filter transmission maximum frequency $\nu_{FDML}$ is between two transmission maximum frequencies of the auxiliary filter. Afterwards, as the FDML filter continues to sweep, the laser will switch to a new optical frequency at the next transmission maximum frequency of the auxiliary filter.

This mode of operation has the advantage that the FDML laser generates a modulated intensity, or a series of pulses, where each pulse corresponds to a different step in optical frequency. In the case where the auxiliary filter is a Fabry Perot filter, the frequency steps are equidistantly spaced. The intensity output of the FDML laser can therefore be used to generate an optical frequency or "k-space" trigger signal directly from the laser since every time the laser steps to a subsequent optical frequency, a change in the output intensity occurs.

Furthermore, the time durations of the optical frequency steps will give information about the dispersion and synchronization properties of the FDML laser. By measuring the timing of each $t_{STEP-ON}$, a feedback signal can be generated to control the AC drive frequency of the FDML filter and the intracavity dispersion.

This operating regime is useful for swept source optical coherence tomography imaging because it can have narrower linewidth and improved performance. It can also be used to generate short pulses with changing frequencies for applications such as coherent anti-Stokes Raman scattering (CARS) microscopy. To generate short pulses, the condition $BW_{FDML} \ll FSR_{auxiliary}$ is desired.

(ii) $BW_{FDML} > FSR_{auxiliary}$: In this case the FDML laser will operate on several modes or transmission maxima of the auxiliary filter at one time, where the group of transmission maxima are selected by the FDML filter. This operating regime is shown in FIG. 24 and has an output as shown in FIG. 21. As the FDML filter is synchronously tuned, the FDML laser will generate a swept stepwise pattern with a distribution or comb of wavelengths or optical frequencies, selected by the auxiliary filter. The center or average frequency or wavelength is selected by the transmission maximum frequency of the FDML filter. The center frequency changes in time as the laser is swept, however the individual frequencies in the comb remain fixed. In this configuration the FDML laser generates a quasi-continuous output intensity without significant modulation, since the combined filtering effect of the FDML filter and the auxiliary filter always allow a set of frequencies to lase.

This mode of operation has the advantage that although the FDML laser generates multiple frequencies at one time, the individual frequencies have narrower linewidths than if the FDML filter is used alone. For many applications such as swept source OCT, interferometric measurement, or metrology, the narrow linewidth improves measurement range or measurement accuracy. The multiple frequency output can produce aliasing effects in OCT imaging or interferometry measurements. Therefore, the spacing of the frequencies determined by the $FSR_{auxiliary}$ must be chosen consistently with the intended application.

(iii) For certain applications, it is also desirable to operate the laser in the regime where $BW_{tuning} \approx FSR_{Auxiliary}$. In this case, the FDML laser will operate predominantly on one or a small number of frequencies corresponding to the auxiliary filter. Different frequencies are output as the FDML filter is synchronously tuned. This regime of operation can be used to improve the coherence properties of the FDML laser. In this case, the intensity output is neither quasi constant, nor is it fully modulated as in the previous cases.

Considering typical gain bandwidths of semiconductor optical amplifiers of approximately 10 THz, an example embodiment would incorporate an auxiliary filter with a free spectral range of less than 1 THz. The adjustably tunable FDML filter would have a free spectral range of more than 1 THz. This embodiment gives an FDML laser output with 10 or more frequency steps, which may be preferred for many applications such as optical coherence tomography and metrology. It should be understood that in some cases, an auxiliary filter may be used where the frequency spacing between consecutive transmission maxima is not equidistant. In this case, the frequency spacing between consecutive transmission maxima would be less than 1 THz for this example embodiment.

The configuration where the FDML laser generates a series of isolated frequency steps, shown in FIGS. 20 and 23, provides new methods to characterize the laser operation and control the FDML laser parameters. In order to achieve optimum FDML laser operation, the drive repetition rate or drive frequency of the tunable FDML filter should be synchronized so that it is substantially equal to the effective roundtrip time of the waveform in the cavity, or a harmonic thereof. Detuning or mismatch results in the waveform returning to the FDML filter and the auxiliary filter at an earlier or later time than desired, when the combination of the FDML filter and the auxiliary filter are not tuned to transmit the incident optical frequency. When the FDML laser is configured to generate steps in frequency, as shown in FIG. 20, the effect of this detuning or mismatch is to cause the frequency steps to become narrower in time, such that the time $t_{STEP-ON}$ becomes shorter, and the output pulses become shorter. The integrated output power over a given time interval also becomes lower. Therefore the drive frequency and other parameters of the FDML filter may be controlled and optimized by measuring either the pulse duration of the output pulses or the output power over a given time interval. One method to control the drive frequency of the FDML filter would be to adjust the drive frequency such that the pulse duration or integrated output power is maximized.

Since each output pulse corresponds to a given optical frequency step in the case where the frequency steps are constant, the output frequency of the FDML laser can be determined by counting the steps in the frequency sweep. A reference signal which indicates when to start counting can be obtained by measuring the FDML laser output with a narrowband filter and photodetector in order to determine when the laser sweeps through a particular reference frequency. For applications such as swept source optical coherence tomography, this feature is particularly important since the pulsed output can be used to trigger data acquisition when the laser is swept stepwise thorough a well defined series of frequencies.

The drive waveform for the tunable FDML filter can also be measured and controlled to obtain a desired swept stepwise output. For some applications it is desirable to generate frequency steps that are equally spaced in time at a constant rate. In this case, the auxiliary filter is chosen to have equally spaced transmission maxima in frequency and the bandwidth of the tunable FDML filter is less than the frequency spacing. If the laser is configured to generate isolated frequency steps, then the timing of each output pulse is a measure of the rate at which the tunable FDML filter is tuned. The drive waveform for the tunable FDML filter can adjusted, generated or synthesized by measuring the timing of the FDML laser output pulses corresponding to the frequency steps and adjusting the drive waveform such that the pulses are generated equally spaced in time. This process of measuring the timing of the output pulses and adjusting the drive waveform of the tunable FDML filter may be performed iteratively. For the case where the tunable FDML filter is a Fabry Perot filter, the drive waveform controls the spacing of the mirrors in the Fabry Perot filter and thereby changes the transmission maximum wavelength of the filter. However, since frequency is inversely proportional to wavelength, scanning the FDML Fabry Perot filter such that the maximum frequency changes at a constant rate may employ correction of the drive waveform.

Dispersion in the FDML cavity causes a change in the group velocity of the light as a function of frequency or wavelength. This causes the round trip time of the optical waveform in the cavity to vary as a function of frequency or wavelength so that only a subset of frequencies or wavelengths are synchronized to the drive waveform of the FDML filter. The effect of dispersion is shown schematically in FIG. 25. The solid lines show a set of frequency steps generated by the FDML laser and corresponding to the combined tuning action of the tunable FDML filter and the auxiliary filter. When the optical waveform including these frequency steps travels around the FDML laser cavity, dispersion causes the different frequency components of the optical waveform to arrive at different times as shown by the dashed lines. The solid and dashed lines are slightly offset so that they can be seen clearly, however it is understood that they are at the same frequencies.

Figure 25:
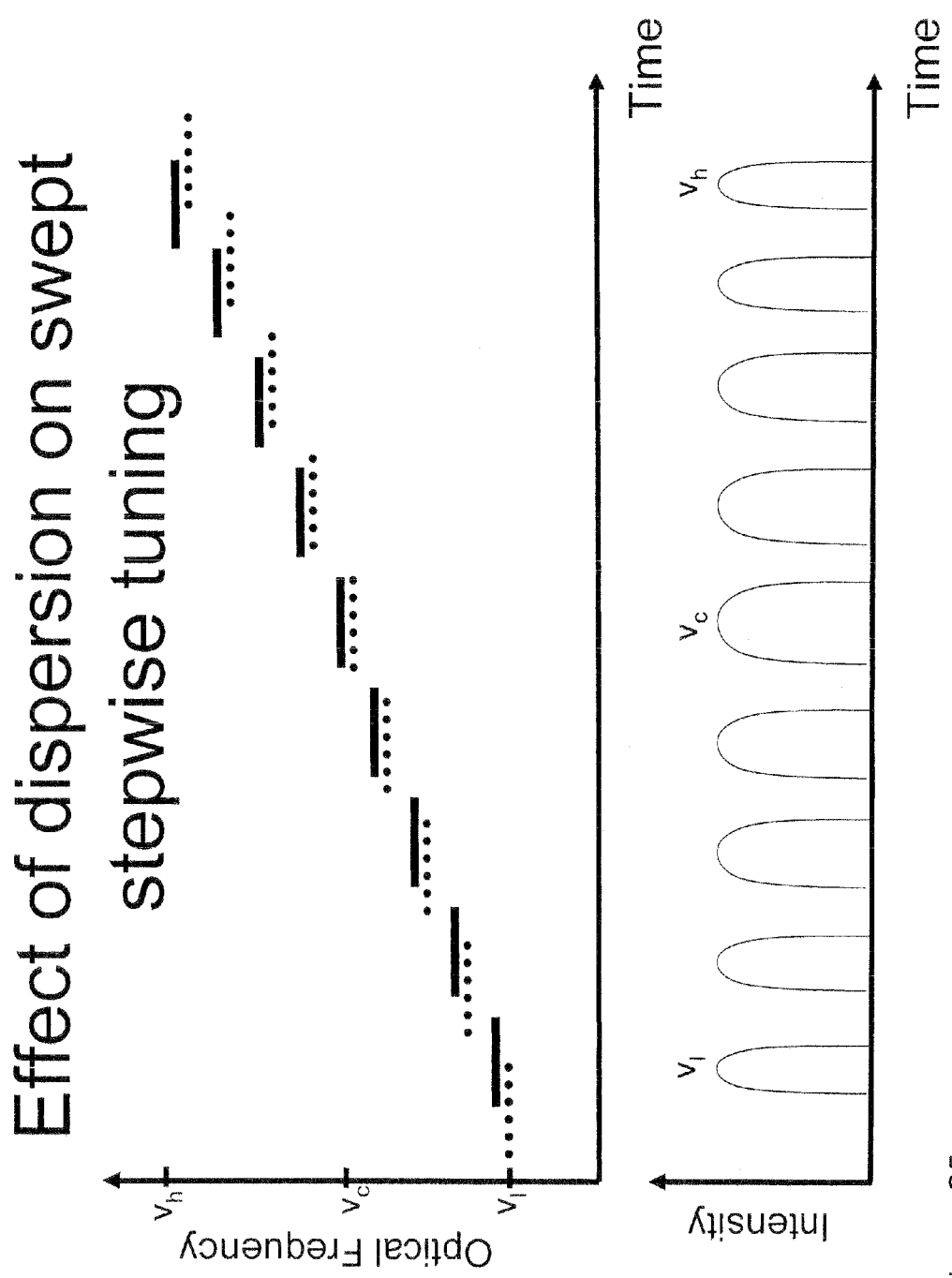
FIG. 25 is a graph depicting the effects of dispersion on a stepwise tuned FDML laser.

FIG. 25 shows the case where the tunable FDML filter period is adjusted such that a central frequency $v_c$ in the optical waveform arrives synchronously with the combined filtering action of the tunable FDML filter and the auxiliary filter. However, the effects of dispersion cause other frequency components, such as low frequencies $v_l$ or high frequencies $v_h$ in the optical waveform to arrive too early or too late with respect to the tuning of the FDML filter. This desynchronization causes a decrease in the output pulse duration of the FDML laser at these frequencies. The swept stepwise FDML laser is less sensitive to dispersion than standard FDML lasers because frequencies within the majority of the step time $T_{ON}$ are still synchronized with the combined filtering of the FDML filter and the auxiliary filter. Finally, it should be noted that measuring the variation in the pulse duration of the output pulses in the swept stepwise FDML laser across the sweep enables a measurement of dispersion.

Figure 26:
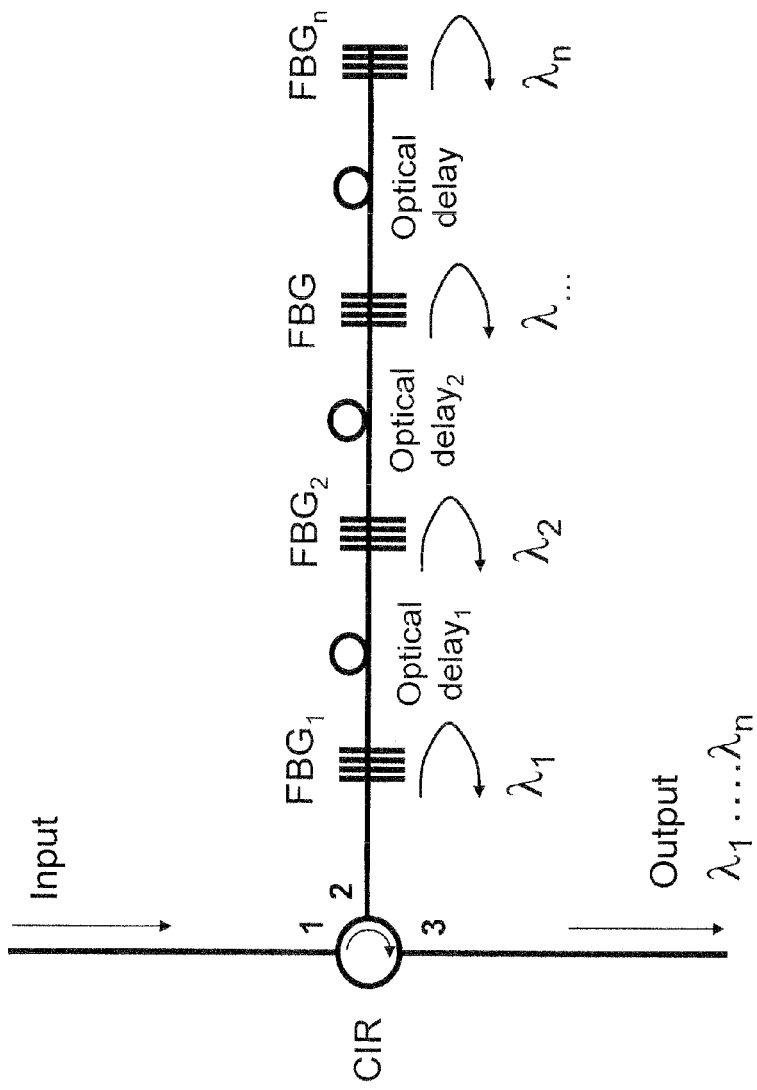
FIG. 26 is a schematic diagram of an auxiliary filter that can be used for a stepwise tuned FDML laser and also to compensate for dispersion according to example embodiments.

As described previously, there are different embodiments possible for the auxiliary filter which provide multiple, narrow bandwidth, transmission maxima within the gain bandwidth of the laser gain medium. Some embodiments of the auxiliary filter enable compensation of dispersion. FIG. 26 shows an example of a filter constructed using a circulator and a series of fiber Bragg gratings (FBG) which have narrow-band reflection maxima at different wavelengths $\lambda_1$, $\lambda_2$, $\lambda_3$, etc. A circulator (CIR) directs input light into the series of fiber Bragg grating filters, which retro-reflect the desired wavelengths of light back to the circulator, where the filtered light is directed to the output. This produces a series of narrow bandwidth transmission maxima at specific wavelengths selected by the fiber Bragg gratings. This configuration enables the FDML laser to generate outputs including different wavelengths or frequencies which are selected by the choice of fiber Bragg grating parameters.

This configuration can also be used to compensate for dispersion in the FDML laser cavity. Dispersion in the laser cavity causes different frequency or wavelength components in the swept optical waveform to have different group velocities or roundtrip times around the laser cavity. This means that the tuned FDML filter cannot be precisely synchronized to the roundtrip time of light in the cavity for all of the frequencies or wavelengths in the swept waveform. However, if optical delays are introduced between the successive fiber Bragg gratings in the filter, and these optical delays are set so that they compensate for differences in the cavity round trip times of the different frequency or wavelength components in the swept waveform, then the FDML filter synchronization condition can be satisfied for multiple frequencies or wavelengths across the sweep bandwidth, thereby compensating dispersion. Compensating dispersion improves the power, tuning bandwidth, and linewidth performance of the FDML laser.

Figure 27:
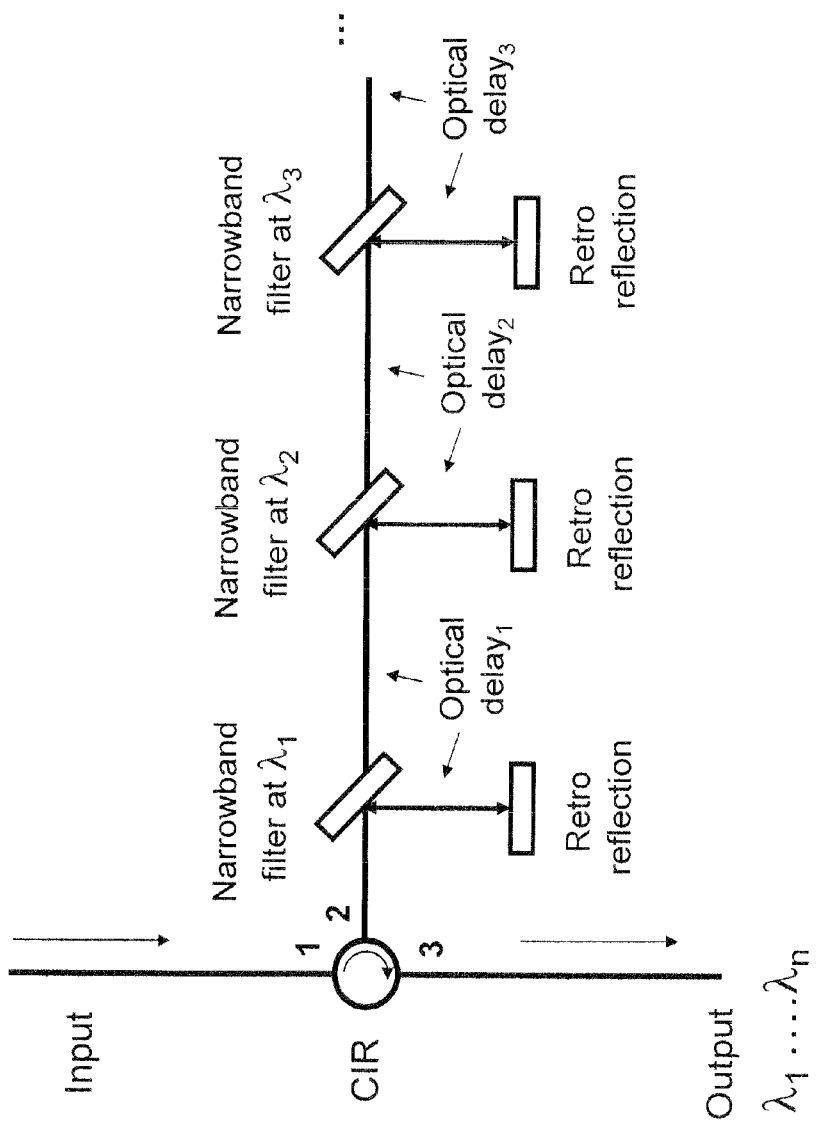
FIG. 27 is a second schematic diagram of an auxiliary filter that can be used for a stepwise tuned FDML laser and also to compensate for dispersion according to example embodiments.

FIG. 27 shows another embodiment where the auxiliary filter is constructed using a circulator and a series of filters which have narrowband reflection maxima at different wavelengths $\lambda_1$, $\lambda_2$, $\lambda_3$, etc. used with retro-reflectors. The filters may be dielectric filters, integrated optical filters, or other known filters which select a narrow bandwidth about a specified wavelength. The different wavelengths are retro-reflected where they pass the filters again and propagate back to the circulator to the output of the auxiliary filter. The particular embodiment shown uses each filter in a double pass configuration, although it is understood that there are also embodiments having the property that they produce a series of transmission maxima at the desired wavelengths or frequencies of operation. Optical delays can be used between the different filter elements in order to compensate dispersion in the FDML laser cavity.

Figure 28:
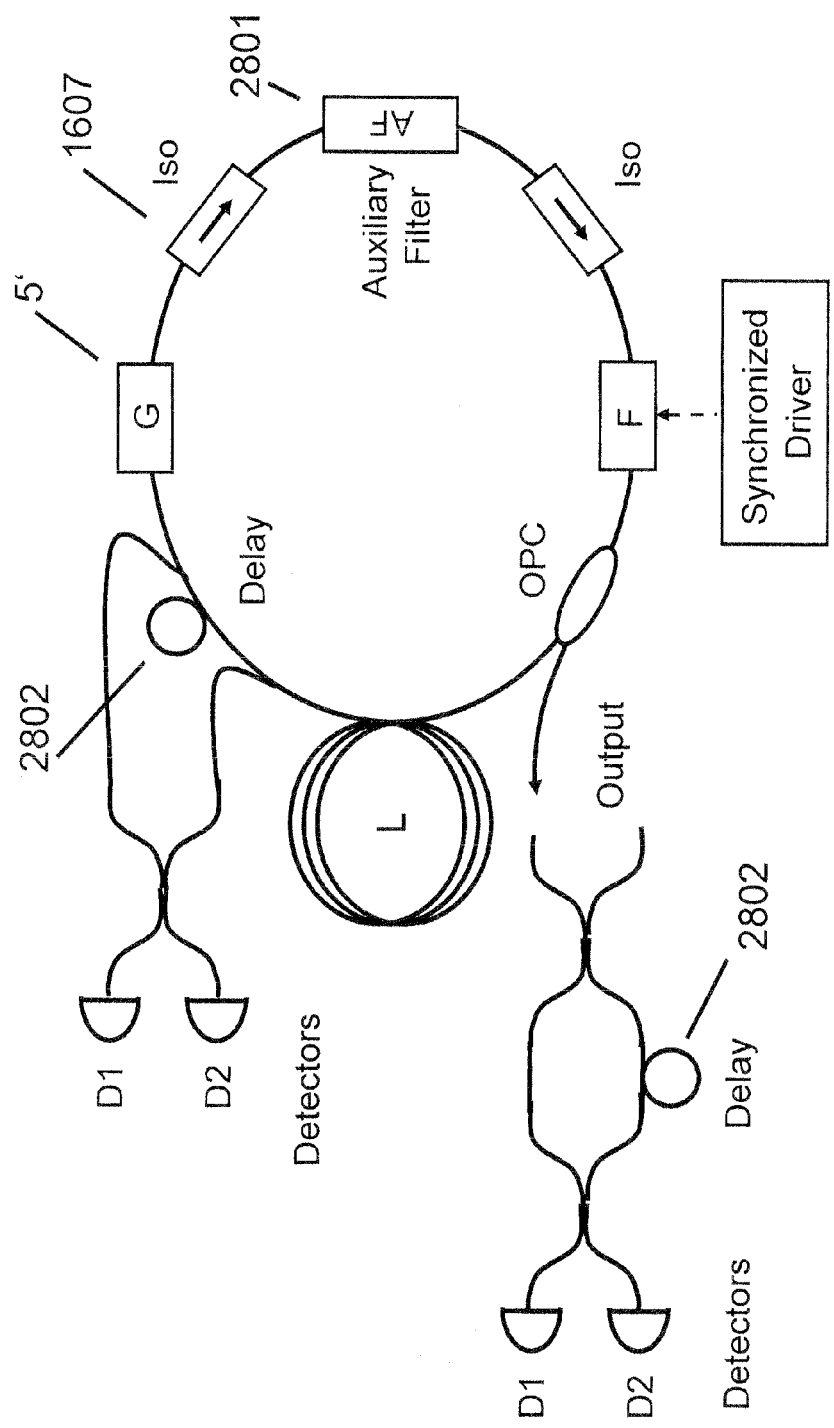
FIG. 28 is a schematic diagram illustrating a setup for measuring the size of optical frequency steps generated by a stepwise tuned FDML laser according to example embodiments.

It is often desirable to measure the optical frequency spacing of step-tuned or swept stepwise laser sources in order to conduct OCT imaging or other measurements. To measure the optical frequency spacing of a swept stepwise FDML laser, two outputs from the laser that are coupled out from different positions in the cavity can be combined interferometrically and the resulting optical signal can be detected with a photodetector. It is also possible to use an external Mach-Zehnder or other analogous interferometer configuration which interferometrically combines a portion of the laser output with a time delayed copy of itself, with the resulting interference signal detected by a photodetector. These configurations are shown schematically in FIG. 28. An auxiliary filter (AF) 2801 is placed inside the laser cavity to generate a stepwise tuned output. While these configurations are shown with a ring FDML laser cavity configuration, it is understood that they may be applied to any other FDML laser cavity. These configurations work for swept stepwise FDML laser configurations where the frequency spacing between steps is small enough so that it can be detected with high speed photodiodes D1 and D2, which can be located either inside or outside the cavity, and electronics. The frequency of the electronic beat signal produced by the photodetectors D1 and D2 will be directly related to the difference in optical frequency between the two outputs from the laser. It is possible to use dual detector configurations where the output of two detectors D1 and D2 are subtracted in order to cancel background intensity variations and add the beat signal. If the delay time between the arrival of the two outputs is adjusted such that it equals one step period $t_{STEP-PERIOD}$, the optical frequency of each individual step can be measured by the electronic beat frequency. The delay time can be adjusted using a fiber delay 2802, which can be either inside or outside the cavity as shown in FIG. 28. Accurate measurement of the optical frequency spacing further enables control and adjustment of the optical frequency spacing using well-known control methods. In this manner the optical frequency spacing between each individual laser step frequency can be measured as an electronic beat frequency. It is therefore possible to measure absolute optical frequency differences with extremely high accuracy.

Figure 29:
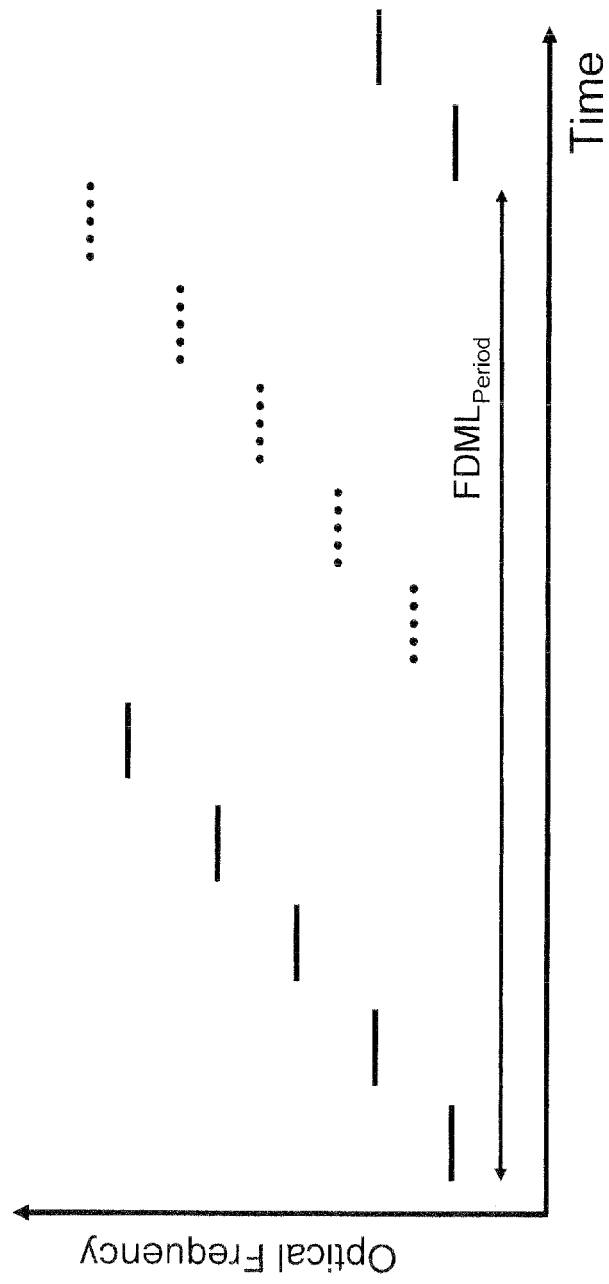
FIG. 29 is a graph showing a stepwise tuned FDML laser where the frequency step characteristics are altered from one sweep to another.

There are situations where the frequency step characteristics of the stepwise tuned FDML laser are desired to vary from sweep to sweep. This situation is illustrated in FIG. 29. For such a situation, the auxiliary filter would change its transmission pattern synchronously to the optical roundtrip time of light in the FDML laser. In one example embodiment, the FDML filter would be tuned synchronously to one harmonic of the optical roundtrip time of light in the laser cavity. The auxiliary filter would be tuned at a lower harmonic of the optical roundtrip time of light in the laser cavity. For example, the FDML filter could be tuned at the second harmonic of the roundtrip time and the auxiliary filter could be tuned at the first harmonic. In this way, every second stepwise tuned output would have a different frequency step pattern.

Alternative Tunable Filters for Stepwise or Discontinuous Tuning

It is possible to achieve stepwise tuning of an FDML laser by using a single tunable filter inside the laser cavity. This may be desirable since it reduces the number of components in the system and thereby reduces complexity. Using a single tunable filter, it is also possible to construct an FDML laser that outputs arbitrarily addressable optical frequencies. This is desirable since it improves the flexibility of the FDML laser output. To obtain stepwise tuning and arbitrarily addressable optical frequencies, the tunable filter should have two characteristics. First, it should filter light into one or more discrete narrow bands, where the center frequencies of the discrete narrow bands can be tuned over time in a periodic manner that enables FDML operation. Second, the center frequencies of the discrete narrow bands should be capable of being set to arbitrary, discrete setpoints.

There are several types of filters that fulfill the requirements for stepwise or discontinuous tuning in FDML. One type of filter is typically referred to as a dynamic gain equalizer (DGE), dynamic channel equalizer, variable wavelength blocker, wavelength selective switch, variable wavelength attenuator, or variable optical attenuator. These filters are commonly used in telecommunications to selectively attenuate or block narrow discrete wavelength bands from a wavelength division multiplexing system. An optical fiber carrying a broad range of wavelengths is typically an input into such a filter. The input light is broken into several discrete wavelength bands using an arrayed waveguide grating (AWG), ring resonators, echelle grating, or other diffractive component. Each discrete wavelength band can then be partially attenuated or fully blocked using attenuating components such as a thermo-optic switch, electro-optic switch, variable optical attenuator, or other type of attenuating component. The discrete wavelength bands are then recombined using a second AWG, ring resonator, echelle grating, or other diffractive component. The filtered light is transmitted out of the filter on a second optical fiber. In this way the filter can be configured to transit one or more discrete wavelength bands.

The center wavelength of the transmitted discrete wavelength band can be tuned in a periodic manner that is synchronized to the roundtrip time of light in an FDML laser cavity, enabling FDML operation. Discontinuous tuning will occur because the filter can be configured only to pass discrete wavelength bands. Since any group of wavelength bands can be blocked at any time by the attenuating components in the filter, the transmitted wavelength band can be set arbitrarily. The discrete wavelength outputs of the FDML laser therefore do not need to be produced in monotonically increasing or decreasing wavelength, and the output wavelength can be arbitrarily addressed.

Vernier Tuned FDML Lasers

It is also possible to realize a stepwise tuned FDML output by incorporating a tunable filter that uses the Vernier effect as the FDML filter. Such a Vernier tunable filter can include a stationary Fabry Perot filter and a tunable Fabry Perot filter with substantially equal bandwidths and slightly different free spectral ranges. While the tunable Fabry Perot filter is tuned, different pairs of transmission maxima overlap, resulting in a stepwise tuning behavior. For FDML operation, the tunable Fabry Perot filter would be tuned synchronously to the roundtrip time of the cavity. It is understood that any other type of optical filter that produces multiple transmission maxima can be used instead of a Fabry Perot filter. It is also understood that the combination of the stationary Fabry Perot filter and the tunable Fabry Perot filter can be considered as one stepwise tuned filter, or one Vernier tunable filter.

Novel Applications for FDML Lasers

The improved performance of FDML lasers compared to previously known conventional wavelength-swept lasers provides novel measurement systems that were not previously possible. The advantages of FDML lasers primarily relate to dramatically increased sweep speed, dramatically decreased amplitude noise, and dramatically decreased phase noise. Therefore, it is possible to make amplitude-based measurements and phase-based measurements with previously unattainable speeds and sensitivities. When an FDML laser is incorporated into a previously known measurement system, the measurement system can become capable of performing measurements that were previously impossible.

In one specific example, the previously known measurement system can be based on low coherence interferometry. This can include optical coherence tomography, optical frequency domain imaging, spectral radar, low coherence backscattering spectroscopy, optical coherence microscopy, or any other variation of low coherence interferometry. In this case, the FDML laser enables interferometric measurements to be performed at previously unattainable speeds and sensitivities. Therefore, samples or targets that are characterized by any of the following properties, or any combination thereof, may be investigated: rapid transient events; rapid motion; high absorption; weak reflection; weak backscattering; weak transmission; and weak generation of a measurement signal. Additionally, the FDML laser enables novel methods for visualizing the low coherence interferometry data. The data can be visualized in a 1D, 2D, 3D, or 4D (3D+time) manner that is different from the manner in which the data is acquired. Using a fixed rectangular coordinate system of three orthogonal axes (X, Y, and Z), for example, the data may be acquired as a successive series of XZ planes over a finite Y dimension, but may be displayed as an XY "en face" image. This geometry is illustrated in FIG. 30.

In a second example, the previously known measurement system can be an optical coherence tomography system that analyzes the amplitude of an interference fringe. This includes ophthalmic OCT imaging systems, endoscope-compatible OCT imaging systems, and microscope-compatible OCT imaging systems. In this case, the FDML laser provides OCT measurements to be performed at previously unattainable speeds and sensitivities. This allows for three-dimensional data sets to be acquired in living subjects with high spatial sampling densities at speeds that significantly reduce the effects of motion artifacts. Motion artifacts associated with living subjects have previously made such high-density 3D imaging impossible. Motion artifacts may be caused by involuntary motion of the organ (such as the eye), tissue motility (such as in the colon, stomach, and esophagus), by the motion of nearby organs, or by motion associated with other processes (such as respiration and the cardiac cycle). The addition of an FDML laser to an OCT imaging system substantially reduces and, in some cases, substantially eliminates these motion artifacts. This is possible because the sweep speed of the FDML laser is several orders of magnitude higher than the characteristic time associated with the tissue motion.

The reduction of motion artifacts in OCT imaging by the inclusion of an FDML laser provides previously impossible OCT image visualization methods. For example, if the sample is oriented as shown in FIG. 30, it may be desirable to display an OCT image oriented in the XY plane. These XY images, which can be referred to as "en face" images, are desirable for registering the OCT data that includes a Z component ("cross sectional images") against data that does not include a Z component. A further advantage of en face images is that en face images are very familiar to human observers. Therefore, en face images enhance the value of the cross-sectional images and allow the cross-sectional images to be more accurately interpreted by a human observer.

Using previously known lasers for OCT imaging, en face images could not be displayed with a high pixel density and a high imaging rate. For analyzing samples where motion artifacts are present, a detailed en face view that is updated at a rate substantially greater than the time associated with the sample motion is necessary. FDML lasers enable high pixel density en face OCT imaging at video data rates, such that the negative effects of motion artifacts are negligible. This substantially improves the ability of a human observer to interpret the OCT data as it is acquired, compared to OCT systems using previously described lasers.

In a third specific example, the previously known measurement system can be an optical coherence tomography system that analyzes the phase of an interference fringe or a combination of the amplitude and phase of an interference fringe. This includes Doppler flow OCT imaging systems, OCT phase microscopy systems, and profilometers based on phase sensitive low coherence interferometry. FDML lasers provide a significant benefit to these systems, since FDML lasers provide extremely low phase noise and extremely high sweep speeds. This allows more sensitive phase measurements to be made at increased speeds.

Doppler flow OCT imaging systems analyze the change in the phase of consecutive interference fringes to detect fluid flow in a sample. It is desirable for a Doppler OCT system to possess a wide flow dynamic range, such that very small and very large flows can be observed simultaneously in the same sample. When wavelength-swept lasers are used in Doppler OCT systems, the lowest detectable flow rate is limited by the phase noise of the laser. The highest detectable flow rate is limited by the sweep speed of the laser. FDML lasers provide phase noise that is significantly lower than previously known swept lasers, and sweep speeds that are significantly higher than previously known swept lasers. Therefore the dynamic range of a Doppler OCT system incorporating an FDML laser is significantly expanded. This allows samples in humans and other living organisms including regions of turbid flow, such as blood vessels and cardiac tissue, to be analyzed. The analysis of turbid flow is not possible with previously known Doppler OCT systems due to the limited flow dynamic range of these systems.

OCT phase microscopy systems and phase-sensitive low coherence profilometers analyze the quantitative phase of interference fringes in order to provide optical path measurements. The resolution of the optical path measurement is determined by the phase noise of the laser, as opposed to the tuning bandwidth of the laser in the case of amplitude-sensitive OCT systems. In an OCT phase microscopy system, multiple axial layers may be analyzed. In a phase-sensitive low coherence profilometer, only one surface layer is analyzed. In both cases, it is desirable for the system to incorporate a laser with low phase noise in order to improve the axial resolution and allow the analysis of samples with increasingly small features. It is also desirable for the laser to have a high sweep speed in order to decrease the data acquisition time and enable the detection of fast transient events. FDML lasers provide both significantly decreased phase noise and significantly increased sweep speed compared to previously known swept lasers. These improvements enable nanometer-scale optical path lengths to be resolved over microsecond-scale time periods. Some applications include the analysis of rapidly-moving mechanical parts such as piezoelectric transducers, micro-electromechanical systems (MEMS), and resonant oscillators.

In the case of phase-sensitive low coherence profilometers, an additional benefit from FDML lasers is gained from the long coherence length of the laser output. Since only one surface is analyzed with a profilometer, the maximum path length that can be measured is determined by the coherence length of the laser. The minimum path length that can be measured is determined by the phase noise of the laser. Since the coherence length of an FDML laser is typically approximately several millimeters, and the phase noise of an FDML laser is typically approximately several tens of picometers, the dynamic range of a profilometer incorporating an FDML laser is typically 8 orders of magnitude. This is a significant advantage over other low coherence profilometers, and allows the analysis of samples with spatial features spanning approximately 8 orders of magnitude. Some applications include examining nanometer-scale surface features of biological cells that have micron-scale or millimeter-scale curvatures, and examining nanometer-scale deformations in MEMS devices as they are actuated over micron-scale or millimeter-scale distances. Investigation of samples such as these is not possible using previously known phase sensitive interferometer systems using previously known wavelength-swept lasers.

In addition to measuring the topography of a surface, thickness measurements using FDML based interferometers have significant advantages. In such systems the interference between the back reflected light intensity form two (e.g. front and back surface) or more surfaces interferes with each other and no reference arm or additional interferometer is needed. Applications could be thickness measurements of transparent media like glass, plastic foil, measuring the thickness of wafers etc.

It should be understood that certain processes, disclosed herein, may be implemented in hardware, firmware, or software. If implemented in software, the software may be stored on any form of computer readable medium, such as random access memory (RAM), read only memory (ROM), compact disk read only memory (CD-ROM), and so forth. In operation, a general purpose or application specific processor loads and executes the software in a manner well understood in the art.

While this invention has been particularly shown and described with references to example embodiments thereof, it will be understood by those skilled in the art that various changes in form and details may be made therein without departing from the scope of the invention encompassed by the appended claims.

The invention claimed is:

1. A tunable laser, comprising:
   a. a swept light source that amplifies light by stimulated emission of radiation, the swept light source including a tunable optical wavelength selective filter, the tunable optical wavelength selective filter configured to adjust an optical wavelength of the swept light source as a function of time in response to a non-sinusoidal selective filter control signal;
   b. a light measurement device, coupled to the swept light source, the light measurement device configured to receive the optical wavelength of the swept light source as an input and to determine a measured parameter as an output; and
   c. an electronic processing device coupled to the light measuring device, the electronic processing device configured to receive the measured parameter as an input and to generate the non-sinusoidal selective filter control signal as an output,
   wherein the swept light source is a Fourier Domain Mode Locking (FDML) laser.

2. The system of claim 1, wherein the optical wavelength of the swept light source as a function of time is piecewise linear.

3. The system of claim 1, wherein the optical wavelength of the swept light source as a function of time is periodic.

4. The system of claim 1, wherein the swept light source has a sweep rate of at least 1 THz per microsecond.

5. The system of claim 1, wherein the tunable optical wavelength selective filter is a Fabry Perot filter.

6. A tunable laser, comprising:
   a. a light measurement device;
   b. an electronic processing device coupled to the light measuring device, the electronic processing device configured to receive a measured parameter as an input and to generate a DC offset control signal as an output; and
   c. a swept light source that amplifies light by stimulated emission of radiation, the swept light source including a tunable optical wavelength-selective filter, the tunable optical wavelength-selective filter having a center wavelength, the tunable optical wavelength-selective filter configured to adjust the center wavelength in response to the DC offset control signal,
   wherein the light measurement device is coupled to the swept light source, the light measurement device configured to receive an optical wavelength of the swept light source as an input and to determine the measured parameter as an output,
   wherein the swept light source is a Fourier Domain Mode Locking (FDML) laser.

7. The system of claim 6, wherein the DC offset control signal is a DC voltage offset control signal.

8. The system of claim 6 wherein the swept light source has a sweep rate of at least 1 THz per microsecond.

9. The system of claim 6, wherein the light measurement device comprises a Fiber Bragg Grating filter.

10. The system of claim 6, wherein the tunable optical wavelength selective filter is a Fabry Perot filter.

11. An optical coherence tomography system comprising the system of claim 6.

12. A tunable laser, comprising:
   a. a light measurement device;
   b. an electronic processing device coupled to the light measuring device, the electronic processing device configured to receive a measured parameter as an input and to generate a DC offset control signal as an output; and
   c. a swept light source that amplifies light by stimulated emission of radiation, the swept light source including a tunable optical wavelength-selective filter, the tunable optical wavelength-selective filter having a center wavelength, the tunable optical wavelength-selective filter configured to adjust the center wavelength in response to the DC offset control signal,
   wherein the light measurement device is coupled to the swept light source, the light measurement device configured to receive an optical wavelength of the swept light source as an input and to determine the measured parameter as an output,
   wherein the light measurement device comprises a Fiber Bragg Grating filter.

13. The system of claim 12, wherein the DC offset control signal is a DC voltage offset control signal.

14. The system of claim 12, wherein the swept light source is a Fourier Domain Mode Locking (FDML) laser.

15. The system of claim 12, wherein the swept light source has a sweep rate of at least 1 THz per microsecond.

16. The system of claim 12, wherein the light measurement device comprises a Fiber Bragg Grating filter.

17. The system of claim 12, wherein the tunable optical wavelength selective filter is a Fabry Perot filter.

18. An optical coherence tomography system comprising the system of claim 12.

* * * * *

UNITED STATES PATENT AND TRADEMARK OFFICE
CERTIFICATE OF CORRECTION

| | | |
|---|---|---|
| PATENT NO. | : 8,923,349 B2 | Page 1 of 1 |
| APPLICATION NO. | : 13/860995 | |
| DATED | : December 30, 2014 | |
| INVENTOR(S) | : Robert A. Huber, James G. Fujimoto and Desmond C. Adler | |

It is certified that error appears in the above-identified patent and that said Letters Patent is hereby corrected as shown below:

On the title page, item (71), delete "Massachuetts Institute of Technology" and insert
-- Massachusetts Institute of Technology --.

On the title page, item (73), delete "Massachusettes Institute of Technology" and insert
-- Massachusetts Institute of Technology --.

Signed and Sealed this
Thirty-first Day of March, 2015

Michelle K. Lee
*Director of the United States Patent and Trademark Office*